United States Patent
Guo et al.

(10) Patent No.: US 11,242,532 B2
(45) Date of Patent: Feb. 8, 2022

(54) SELF-ASSEMBLED 3D RNA CAGE NANOPARTICLES

(71) Applicants: Ohio State Innovation Foundation, Columbus, OH (US); Ball State University, Muncie, IN (US)

(72) Inventors: Peixuan Guo, Dublin, OH (US); Daniel Jasinski, Columbus, OH (US); Hui Li, San Francisco, CA (US); Emil Khisamutdinov, Muncie, IN (US)

(73) Assignees: Ohio State Innovation Foundation, Columbus, OH (US); Ball State University, Muncie, IN (US)

(*) Notice: Subject to any disclaimer, the term of this patent is extended or adjusted under 35 U.S.C. 154(b) by 0 days.

(21) Appl. No.: 16/091,747

(22) PCT Filed: May 10, 2017

(86) PCT No.: PCT/US2017/032001
§ 371 (c)(1),
(2) Date: Oct. 5, 2018

(87) PCT Pub. No.: WO2017/197009
PCT Pub. Date: Nov. 16, 2017

(65) Prior Publication Data
US 2019/0127739 A1    May 2, 2019

Related U.S. Application Data

(60) Provisional application No. 62/333,890, filed on May 10, 2016, provisional application No. 62/380,238, filed on Aug. 26, 2016.

(51) Int. Cl.
| | |
|---|---|
| *C12N 15/115* | (2010.01) |
| *C12N 15/113* | (2010.01) |
| *C12N 15/10* | (2006.01) |
| *A61P 37/04* | (2006.01) |
| *C12N 15/11* | (2006.01) |
| *C12N 15/117* | (2010.01) |
| *A61K 48/00* | (2006.01) |

(52) U.S. Cl.
CPC ............ *C12N 15/115* (2013.01); *A61P 37/04* (2018.01); *C12N 15/10* (2013.01); *C12N 15/11* (2013.01); *C12N 15/113* (2013.01); *C12N 15/117* (2013.01); *A61K 48/005* (2013.01); *C12N 2310/16* (2013.01); *C12N 2310/17* (2013.01); *C12N 2310/341* (2013.01); *C12N 2320/32* (2013.01)

(58) Field of Classification Search
CPC ......... A61P 37/04; C12N 15/10; C12N 15/11; C12N 15/113; C12N 15/115; C12N 15/117; C12N 2310/16; C12N 2310/17; C12N 2310/341; C12N 2320/32; A61K 51/06; A61K 51/12

USPC ....... 435/6.1, 91.1, 91.31, 455, 458; 514/44; 536/23.1, 24.5
See application file for complete search history.

(56) References Cited

U.S. PATENT DOCUMENTS

2012/0263648 A1* 10/2012 Shapiro .................... A61P 9/10
424/9.1
2016/0237439 A1* 8/2016 Liang ................. C12N 15/1137

FOREIGN PATENT DOCUMENTS

WO    2015057511 A1    4/2015

OTHER PUBLICATIONS

Binzel et al, Biochemistry, vol. vol. 53, pp. 2221-2231. (Year: 2014).*
Sadowski et al., ACS Nano., vol. 8, No. 4, pp. 3251-3259 (Year: 2014).*
Lee et al., Nat. Nanotechnol., vol. 7, No. 6, pp. 389-393 (Year: 2012).*
Li et al., Nano Today, vol. 10, No. 5, pp. 631-655 (Year: 2015).*
Severcan et al., Nano. Lett., vol. 9, No. 3, pp. 1270-1277 (Year: 2009).*
Guo, P., Nature Nanotechnology, vol. 5, pp. 833-842 (Year: 2010).*
International Search Report issued for PCT/US2017/032001, dated Aug. 10, 2017.
Binzel et al., Entropy-Driven One-Step Formation of Phi29 pRNA 3WJ from Three RNA Fragments, Biochemistry 53, 2221-2231, 2014.
Li et al., Controllable Self-Assembly of RNA Tetrahedrons with Precise Shape and Size for Cancer Targeting, Adv. Mater. 1-7, 2016.
Phua et al., Messenger RNA (mRNA) Nanoparticle Tumour Vaccination, Nanoscale 6(14): 7715-7729, 2014.
Afonin et al., Multifunctional RNA Nanoparticles, Nano Lett. 2014, 14, 5662.
Baugh et al., 2.8 A Crystal Structure of the Malachite Green Aptamer, J Mol. Biol. 2000, 301, 117-128.
Binzel et al., Ellropy-Driven One-Step Formation of Phi29 pRNA 3WJ from Three RNA Fragments, Biochemistry 2014 53, 2221.

(Continued)

*Primary Examiner* — Jane J Zara
(74) *Attorney, Agent, or Firm* — Thomas|Horstemeyer LLP

(57) ABSTRACT

Disclosed herein are three-dimensional cage molecules, wherein the cage molecule is composed of RNA. Also disclosed is a composition including the three-dimensional cage molecule, as well as a pharmaceutical composition containing the three-dimensional cage molecule. Also disclosed herein are methods of administering a cage molecule, composition, or formulation thereof to a subject in need thereof.

20 Claims, 63 Drawing Sheets
Specification includes a Sequence Listing.

(56) References Cited

OTHER PUBLICATIONS

Chen et al., Inhibition of heregulin signaling by an aptamer that preferentially binds to the oligomeric form of human epidermal growth factor receptor-3, PNAS, vol. 100, No. 16, 9226-9231, 2003.
Chworos et al., Jaeger, Building Programmable Jigsaw Puzzles with RNA, Science 2004, 306, 2068.
Dibrov et al., Self-assembling RNA square, PNAS USA 2011, vol. 108, 6405-6408.
Esposito et al., A Neutralizing RNA Aptamer against EGFR Causes Selective Apoptotic Cell Death, PLoS. One. 2011, 6, e24071.
Flinders et al., Recognition of Planar and Nonplanar Ligands in the Malachite Green—RNA Aptamer Complex, Chembiochem 2004, 5, 62-72.
Garmann et al., Visualizing the global secondary structure of a viral RNA genome with cryo-electron microscopy, RNA 2015, 21, 877.
Grabow et al., Self-Assembling RNA Nanorings Based on RNAI/II Inverse Kissing Complexes, Nano Lett. 2011, 11, 878.
Zhang et al., Crystal structure of 3WJ core revealing divalent ion-promoted thermostability and assembly of the Phi29 hexameric motor pRNA, RNA 2013, 19, 1226.
Guo et al., A small viral RNA is required for in vitro packaging of bacteriophage phi 29 DN, Science 1987, 236, 690.
Guo et al., Inter-RNA Interaction of Phage 29 pRNA to Form a Hexameric Complex for Viral DNA Transportatio, Cell. 1998, 2, 149.
Guo, The emerging field of RNA nanotechnology, Nature Nanotechnology 2010, 5, 833.
Hao et al., Construction of RNA nanocages by re-engineering the packaging RNA of Phi29 bacteriophage, Nat. Commun. 2014, 5, 3890.
Haque et al., Ultrastable synergistic tetravalent RNA nanoparticles for targeting to cancers, Nano Today,16, 2012, 7, 245.
Hoeprich et al., Bacterial virus phi29 pRNA as a hammerhead ribozyme escort to destroy hepatitis B virus, Gene Ther. 2003, 10, 1258-1267.
Hynes et al., ERBB receptors and cancer: the complexity of targeted inhibitors, Nat Rev. Cancer 2005, 5, 341.
Jasinski et al., Hydrophobic Effect from Conjugated Chemicals or Drugs on In Vivo Biodistribution of RNA Nanoparticles, ACS Nano 2014, 8, 7620.
Jones et al., Programmable materials and the nature of the DNA bond, Science 2015, 347, 1260901.
Khisamutdinov et al., RNA as a Boiling-Resistant Anionic Polymer Material To Build Robust Structures with Defined Shape and Stoichiometry, ACS Nano. 2014, 8, 4771.
Khisamutdinov et al., Simple Method for Constructing RNA Triangle, Square, Pentagon by Tuning Interior Rna 3WJ Angle from 60° to 90° or 108°, Methods Mal Biol 2015, 1316, 181.
Kim et al., In Vitro Selection of RNA Aptamer and Specific Targeting of ErbB2 in Breast Cancer Cells, Nucleic Acid Ther. 2011, 21, 173.
Lee et al., Molecularly Self-Assembled Nucleic Acid Nanoparticles for Targeted In Vivo siRNADelivery, Nat. Nano technol. 2012, 7(6), 389-393.
Leontis et al., Analysis of RNA motifs, Curr. Opin. Struct. Biol. 2003, 13, 300.
Li et al., RNA as a stable polymer to build controllable and defined nanostructures for material and biomedical applications, Nano Today 2015, 10, 631.
Li et al., A Replicable Tetrahedral Nanostructure Self-Assembled from a Single DNA StrandJ Am. Chem. Soc. 2009, 131(36), 13093-13098.
Lyubchenko et al., Imaging of nucleic acids with atomic force microscopy, Methods 2011, 54(2), 274-283.
Nasalean et al., Controlling RNA self-assembly to form filaments, Nucleic Acids Res. 2006, 34, 1381.
Paige et al., Fluorescence Imaging of Cellular Metabolites with RNA, Science 2012, 335, 1194.
Pettersen et al., UCSF Chimera—A Visualization System for Exploratory Research and Analysis, Journal of Computational Chemistry 2004, 25, 1605.
Zhang et al., Structural DNA Nanotechnology: State of the Art and Future Perspective, J. Am. Chem. Soc. 2014, 136, 11198.
Sadowski et al., Developmental Self-Assembly of a DNA Tetrahedron, ACS Nano 2014, 8, 3251.
Shu et al., Stable RNA nanoparticles as potential new generation drugs for cancer therapy, Adv. Drug Deliv. Rev. 2014, 66C, 74.
Seeman, Nanomaterials based on DNA, Annu. Rev. Biochem. 2010, 79, 65.
Severcan et al., Square-Shaped RNA Particles From Different RNA Folds, Lett. 2009, 9, 1270-1277.
Severcan et al., A polyhedron made of tRNAs, Nat. Chem. 2010, 2, 772-9.
Shu et al., Bottom-up Assembly of RNA Arrays and Superstructures as Potential Parts in Nanotechnology, Nano Lett. 2004, 4, 1717-1723.
Shu et al., New approach to develop ultra-high inhibitory drug using the power function of the stoichiometry of the targeted nanomachine or biocomplex, RNA 2013, 19, 8, 766.
Shu et al., Fabrication of pRNA nanoparticles to deliver therapeutic RNAs and bioactive compounds into tumor cells, Nat Protoc. 2013, 8, 1635.
Shu et al., Thermodynamically stable RNA three-way junction for constructing multifunctional nanoparticles for delivery of therapeutics, Nature Nanotechnology 2011, 6, 658-667.
Shu et al., Systemic Delivery of Anti-miRNA for Suppression of Triple Negative Breast Cancer Utilizing RNA Nanotechnology, ACS Nano 2015, 9, 9731.
Srisawat et al., Streptavidin aptamers: Affinity tags for the study of RNAs and ribonucleoproteins, RNA. 2001, 7, 632.
Sugimoto et al., Thermodynamic Parameters To Predict Stability of RNA/DNA Hybrid Duplexes, Biochemistry 1995, 34, 11211.
Thiel et al., Delivery of chemo-sensitizing siRNAs to HER2+-breast cancer cells using RNA aptamers, Nucleic Acids Res. 2012, 40, 6319-6337.
Office Action issued by the Chinese Patent Office for application 201780029100.9, dated May 6, 2021.

\* cited by examiner

RNA Pyramid

FIG. 22A     FIG. 22B

|  | Image Pair |
|---|---|
| Total Particle Pairs | 50 |
| Particle Pairs in Cluster | 24 |
| Fraction in Cluster | 48% |
| Mean Tilt Angle | 14.8 |
| RMSD Tilt Angle | 5.73 |
| Mean Tilt Axis | -168.8 |
| RMSD Tilt Axis | 50.33 |
| Tilt Angle via Microscope | 15 |

FIG. 28

| | |
|---|---|
| MG Aptamer | 5'- GGAUCCCGACUGGCGAGAGCCAGGUAACGAAUGGAUCC -3' (SEQ ID NO:25) |
| Spinach Aptamer | 5'- GGACGCAACUGAAUGAAAUGGUGAAGGACGGGUCCAGGUGUGGCUGCUUCGGCAGUGCAGCUUGUUGAGUAGAGUGUGAGCUCCGUAACUAGUCGCGUCC -3' (SEQ ID NO:26) |
| HBV Ribozyme | 5'- GGGACGAAAAAAACAAAUUCUUUACUGAUGAGUCCGUGAGGACGAAACGGGUCAAAAAAACGUCCC -3' (SEQ ID NO:27) |
| Streptavidin Aptamer | 5'- GGAUGCGGCCGCCGACCAGAAUCAUGCAAGUGCGUAAGAUAGUCGCGGGUCGGCGGCCGCAUCC -3' (SEQ ID NO:28) |
| EGFR Aptamer | 5'- GCCUUAGUAACGUGCUUUGAUGUCGAUUCGACAGGAGGC -3' (SEQ ID NO:29) |
| Luciferase siRNA Sense Strand | 5'- AACUUACGCUGAGUACUUCGAUU -3' (SEQ ID NO:30) |
| Luciferase siRNA Antisense Strand | 5'- UCGAAGUACUCAGCGUAAGUU -3' (SEQ ID NO:19) |

FIG. 29

SEQUENCE LISTING

```
<160> NUMBER OF SEQ ID NOS: 30

<210> SEQ ID NO 1
<211> LENGTH: 120
<212> TYPE: RNA
<213> ORGANISM: Artificial Sequence
<220> FEATURE:
<223> OTHER INFORMATION: A sequence for a strand of an RNA nanocage

<400> SEQUENCE: 1 gcaauggguac gguacuucca uugucaugug uauguugggg auuaaacccu gauugaguuc    60
agcccacaua cuuuguugau ugguugucaa ucauggcaaa agugcacgcu acuccgcuaa   120

<210> SEQ ID NO 2
<211> LENGTH: 88
<212> TYPE: RNA
<213> ORGANISM: Artificial Sequence
<220> FEATURE:
<223> OTHER INFORMATION: RNA strand 1 from Fig 1B & Fig 29

<400> SEQUENCE: 2
ggacugauac gaaucaucgu guagcaccag cuguaaucga uguguacggg aagagccuau    60
gcccauccua cuuuguucua cuauggcg                                       88

<210> SEQ ID NO 3
<211> LENGTH: 88
<212> TYPE: RNA
<213> ORGANISM: Artificial Sequence
<220> FEATURE:
<223> OTHER INFORMATION: RNA strand 2 from Fig 1B & Fig 29

<400> SEQUENCE: 3
ggugcuacac gauguguagc cagacuuagc ggaauguucg uacuuuguuc augcgaggcc    60
guccaauacc gaaucaucga uuacagcu                                       88

<210> SEQ ID NO 4
<211> LENGTH: 88
<212> TYPE: RNA
<213> ORGANISM: Artificial Sequence
<220> FEATURE:
<223> OTHER INFORMATION: RNA strand 3 from Fig 1B & Fig 29

<400> SEQUENCE: 4
gggcaguuga gauguguacg aacauuccgc uaagucuggc uacuuuguuc guaucaguco    60 cgccauagua gaaucaucgu aucaccau                                       88

<210> SEQ ID NO 5
<211> LENGTH: 88
<212> TYPE: RNA
<213> ORGANISM: Artificial Sequence
<220> FEATURE:
```

<223> OTHER INFORMATION: RNA strand 4 from Fig 1B & Fig 29

<400> SEQUENCE: 5 ggcucgcau gaaucaucuc aacugcccau ggugauacga uguguaggau gggcauaggc    60
ucuucccgua cuuuguucgg uauuggac                                     88

<210> SEQ ID NO 6
<211> LENGTH: 61
<212> TYPE: RNA
<213> ORGANISM: Artificial Sequence
<220> FEATURE:
<223> OTHER INFORMATION: a3WJ/EGFR aptamer from Fig 12A

<400> SEQUENCE: 6
uugccaugug uauguggggc cuuaguaacg ugcuuugaug ucgauucgac aggaggcccc    60
a                                                                   61

<210> SEQ ID NO 7
<211> LENGTH: 16
<212> TYPE: RNA
<213> ORGANISM: Artificial Sequence
<220> FEATURE:
<223> OTHER INFORMATION: b3WJ from Fig 12A

<400> SEQUENCE: 7
cauacuuugu ugaucc                                                   16

<210> SEQ ID NO 8
<211> LENGTH: 16
<212> TYPE: RNA
<213> ORGANISM: Artificial Sequence
<220> FEATURE:
<223> OTHER INFORMATION: c3WJ from Fig 12A and 13A

<400> SEQUENCE: 8
ggaucaauca uggcaa                                                   16

<210> SEQ ID NO 9
<211> LENGTH: 38
<212> TYPE: RNA
<213> ORGANISM: Artificial Sequence
<220> FEATURE:
<223> OTHER INFORMATION: a3WJ/CD133 aptamer from Fig 13A

<400> SEQUENCE: 9
uuggccaugu guauguggc ccuccuacau agggccca                            38

<210> SEQ ID NO 10
<211> LENGTH: 35
<212> TYPE: RNA
<213> ORGANISM: Artificial Sequence
<220> FEATURE:
<223> OTHER INFORMATION: b3WJ/CD133 aptamer from Fig 13A

<400> SEQUENCE: 10
cauacuuugu ugaucccaga acguauacua uucug                              35

<210> SEQ ID NO 11
<211> LENGTH: 187
<212> TYPE: RNA
<213> ORGANISM: Artificial Sequence
<220> FEATURE:
<223> OTHER INFORMATION: RNA strand 1 from Fig 23 & Fig 30

<400> SEQUENCE: 11

```
ggaugacagg ugucaaugca cugauacgaa ucaucgugua gcagauucga uuguacucgu    60
ccucagguuc uacagacgag cuguaaucga uguuacggg aagagaguca cuugcguggc    120
```

```
ggaugacagg ugucaaugca cugauacgaa ucaucgugua gcagauucga uuguacucgu    60
ccucagguuc uacagacgag cuguaaucga uguguacggg aagagaguca cuugcguggc   120
uccccucuac ugcaguagug uaugcccauc cuacuuuguu cuacuauggc ggcaaguaug   180
auccaug                                                             187
```

<210> SEQ ID NO 12
<211> LENGTH: 187
<212> TYPE: RNA
<213> ORGANISM: Artificial Sequence
<220> FEATURE:
<223> OTHER INFORMATION: strand 2 from Fig 23 & Fig 30

<400> SEQUENCE: 12

```
ggacgaguac aaucgaaucu gcuacacgau guguagccag acuuaguguc gugaccguac    60
gaccgacucg agucgacgac ggaauguucg uacuuuguuc augcgagggc gauagcgccu   120
agcugccucu gacuggaccu aguguccaau accgaaucau cgauuacagc ucgucuguag   180
aaccuga                                                             187
```

<210> SEQ ID NO 13
<211> LENGTH: 187
<212> TYPE: RNA
<213> ORGANISM: Artificial Sequence
<220> FEATURE:
<223> OTHER INFORMATION: RNA strand 3 from Fig 23 & Fig 30

<400> SEQUENCE: 13

```
ggagagcgua guccuguacg caguugagau guguacgaac auuccgucgu cgacucgagu    60
cggucguacg gucacgacac uaagucuggc uacuuuguuc guaucagugc auugacaccu   120
gucaucccau ggaucauacu ugccgccaua guagaaucau cguaucacca ugaacaucau   180
cacagac                                                             187
```

<210> SEQ ID NO 14
<211> LENGTH: 187
<212> TYPE: RNA
<213> ORGANISM: Artificial Sequence
<220> FEATURE:
<223> OTHER INFORMATION: RNA strand 4 from Fig 23 & Fig 30

<400> SEQUENCE: 14

```
ggcagcuagg cgcuaucgcc cucgcaugaa ucaucucaac ugcguacagg acuacgcucu    60
ccgucuguga ugauguucau ggugauacga ugugguaggau gggcauacac uacugcagua   120
gaggggagcc acgcaaguga cucucuuccc guacuuuguu cgguauugga cacuaggucc   180
agucaga                                                             187
```

<210> SEQ ID NO 15
<211> LENGTH: 111
<212> TYPE: RNA
<213> ORGANISM: Artificial Sequence
<220> FEATURE:
<223> OTHER INFORMATION: RNA strand 1 from Fig 26

<400> SEQUENCE: 15

```
ggacugauac gaaucaucgu guagcaccag cuguaaucga uguguacggg aagagccuau    60
gcccauccua cuuuguucua cuauggcgaa cuuacgcuga guacuucgau u           111
```

<210> SEQ ID NO 16

```
<211> LENGTH: 111
<212> TYPE: RNA
<213> ORGANISM: Artificial Sequence
<220> FEATURE:
<223> OTHER INFORMATION: RNA strand 2 from Fig 26

<400> SEQUENCE: 16
ggugcuacac gauguguagc cagacuuagc ggaauguucg uacuuuguuc augcgaggcc      60
guccaauacc gaaucaucga uuacagcuaa cuuacgcuga guacuucgau u              111

<210> SEQ ID NO 17
<211> LENGTH: 111
<212> TYPE: RNA
<213> ORGANISM: Artificial Sequence
<220> FEATURE:
<223> OTHER INFORMATION: RNA strand 3  from Fig 26

<400> SEQUENCE: 17
gggcaguuga gauguguacg aacauuccgc uaagucuggc uacuuuguuc guaucagucc      60
cgccauagua gaaucaucgu aucaccauaa cuuacgcuga guacuucgau u              111

<210> SEQ ID NO 18
<211> LENGTH: 111
<212> TYPE: RNA
<213> ORGANISM: Artificial Sequence
<220> FEATURE:
<223> OTHER INFORMATION: RNA strand 4 from Fig 26

<400> SEQUENCE: 18
ggccucgcau gaaucaucuc aacugcccau ggugauacga uguguaggau gggcauaggc      60
ucuucccgua cuuuguucgg uauuggacaa cuuacgcuga guacuucgau u              111

<210> SEQ ID NO 19
<211> LENGTH: 21
<212> TYPE: RNA
<213> ORGANISM: Artificial Sequence
<220> FEATURE:
<223> OTHER INFORMATION: Luc siRNA antisense from Figs 26 and 31

<400> SEQUENCE: 19
ucgaaguacu cagcguaagu u                                                21

<210> SEQ ID NO 20
<211> LENGTH: 127
<212> TYPE: RNA
<213> ORGANISM: Artificial Sequence
<220> FEATURE:
<223> OTHER INFORMATION: RNA strand 1 from Fig 27

<400> SEQUENCE: 20
ggacugauac gaaucaucgu guagcaccag cguaaucga uguguacggg aagagccuau       60
gcccauccua cuuuguucua cuauggcggc cuuaguaacg ugcuuugaug ucgauucgac     120
aggaggc                                                               127

<210> SEQ ID NO 21
<211> LENGTH: 127
<212> TYPE: RNA
<213> ORGANISM: Artificial Sequence
<220> FEATURE:
<223> OTHER INFORMATION: RNA strand 2 from Fig 27

<400> SEQUENCE: 21
ggugcuacac gauguguagc cagacuuagc ggaauguucg uacuuuguuc augcgaggcc      60
```

```
guccaauacc gaaucaucga uuacagcugc cuuaguaacg ugcuuugaug ucgauucgac    120
aggaggc                                                              127

<210> SEQ ID NO 22
<211> LENGTH: 104
<212> TYPE: RNA
<213> ORGANISM: Artificial Sequence
<220> FEATURE:
<223> OTHER INFORMATION: RNA strand 3  from Fig 27

<400> SEQUENCE: 22
gggcaguuga gauguguacg aacauuccgc uaagucuggc acuuuguuc guaucagucc      60 cgccauagua gaaucaucgu ucaccauuu gccaugauug aucc                      104

<210> SEQ ID NO 23
<211> LENGTH: 127
<212> TYPE: RNA
<213> ORGANISM: Artificial Sequence
<220> FEATURE:
<223> OTHER INFORMATION: RNA strand 4 from Fig 27

<400> SEQUENCE: 23
ggccucgcau gaaucaucuc aacugcccau ggugaaucga uguguaggau gggcauaggc    60
ucuucccgua cuuuguucgg uauuggacgc cuuaguaacg ugcuuugaug ucgauucgac   120
aggaggc                                                              127

<210> SEQ ID NO 24
<211> LENGTH: 16
<212> TYPE: RNA
<213> ORGANISM: Artificial Sequence
<220> FEATURE:
<223> OTHER INFORMATION: Alexa647 from Fig 27

<400> SEQUENCE: 24
ggaucaauca uggcaa                                                    16

<210> SEQ ID NO 25
<211> LENGTH: 38
<212> TYPE: RNA
<213> ORGANISM: Artificial Sequence
<220> FEATURE:
<223> OTHER INFORMATION: MG aptamer from Fig 31

<400> SEQUENCE: 25
ggaucccgac uggcgagagc cagguaacga auggaucc                            38

<210> SEQ ID NO 26
<211> LENGTH: 100
<212> TYPE: RNA
<213> ORGANISM: Artificial Sequence
<220> FEATURE:
<223> OTHER INFORMATION: Spinach aptamer from Fig 31

<400> SEQUENCE: 26
ggacgcaacu gaaugaaaug gugaaggacg ggnccaggug uggcugcuuc ggcagugcag    60
cuuguugagu agagugugag cuccguaacu agucgcgucc                          100

<210> SEQ ID NO 27
<211> LENGTH: 68
<212> TYPE: RNA
<213> ORGANISM: Artificial Sequence
<220> FEATURE:
```

<223> OTHER INFORMATION: HBV ribozyme from Fig 31

<400> SEQUENCE: 27
gggacgaaaa aaaacaaauu cuuuacugau gaguccguga ggacgaaacg ggucaaaaaa      60
aacguccc                                                              68

<210> SEQ ID NO 28
<211> LENGTH: 64
<212> TYPE: RNA
<213> ORGANISM: Artificial Sequence
<220> FEATURE:
<223> OTHER INFORMATION: streptavidin apatamer from Fig 31

<400> SEQUENCE: 28
ggaugcggcc gccgaccaga aucaugcaag ugcguaagau agucgcgggu cggcggccgc      60
aucc                                                                  64

<210> SEQ ID NO 29
<211> LENGTH: 39
<212> TYPE: RNA
<213> ORGANISM: Artificial Sequence
<220> FEATURE:
<223> OTHER INFORMATION: EGFR aptamer from Fig 31

<400> SEQUENCE: 29
gccuuaguaa cgugcuuuga ugucgauucg acaggaggc                            39

<210> SEQ ID NO 30
<211> LENGTH: 23
<212> TYPE: RNA
<213> ORGANISM: Artificial Sequence
<220> FEATURE:
<223> OTHER INFORMATION: Luc siRNA sense from Fig 31

<400> SEQUENCE: 30
aacuuacgcu gaguacuucg auu                                             23

SELF-ASSEMBLED 3D RNA CAGE NANOPARTICLES

CROSS-REFERENCE TO RELATED APPLICATIONS

This application claims the benefit of and priority to U.S. Provisional Patent Application No. 62/380,238, filed on Aug. 26, 2016, and to U.S. Provisional Patent Application No. 62/333,890, filed on May 10, 2016, the contents of which are incorporated by reference herein in their entirety.

STATEMENT REGARDING FEDERALLY SPONSORED RESEARCH

This invention was made with government support under grant numbers EB019036; EB012135; and CA151648 awarded by the National Institutes of Health. The government has certain rights in the invention.

SEQUENCE LISTING

This application contains a sequence listing filed in electronic form as an ASCII.txt file entitled 321501-2030_ST25.txt, created on May 10, 2017. The content of the sequence listing is incorporated herein in its entirety.

BACKGROUND

Significant advances in the development of small molecule drugs, RNAi therapies, and various aptamer therapies show promise to treat varying disease from cancer to genetic disorders. With that in mind, there exists a need for improved drug delivery technologies.

SUMMARY

In accordance with the purposes of the disclosed materials, compounds, compositions, articles, devices, and methods, as embodied and broadly described herein, the disclosed subject matter relates to compositions and methods of making and using the compositions.

Disclosed herein is a three-dimensional cage molecule, wherein the cage molecule contains RNA. Also disclosed is a composition containing the three-dimensional cage molecule, as well as a pharmaceutical composition containing the three-dimensional cage molecule.

Further disclosed is a method of inhibiting or reducing the expression of a target gene in a cell including the step of contacting the cell with a therapeutically effective amount of a three-dimensional cage molecule, wherein the cage molecule contains RNA.

Disclosed is a method of treating disease in a subject, including the step of administering to the subject the pharmaceutical composition disclosed herein.

Also disclosed is a method of imaging a cell, the method including the step of exposing the cell to the three-dimensional cage structure disclosed herein.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying Figure, which is incorporated in and constitutes a part of this specification, illustrates several aspects and together with the description serves to explain the principles of the invention.

FIG. 1A demonstrates an embodiment of a 2D sequence (SEQ ID NO:1) of pRNA monomer showing the central pRNA-3WJ motif. The 22-nucleotide core sequence (with red color) of pRNA-3WJ is used to construct RNA tetrahedrons. FIGS. 1B-1C shows 2D sequences (FIG. 1B) and 3D computational model (FIG. 1C) of RNA tetrahedrons. Strand 1 (SEQ ID NO:2); Strand 2 (SEQ ID NO:3); Strand 3 (SEQ ID NO:4); Strand 4 (SEQ ID NO:5). FIG. 1D shows an image of a representative 7% native PAGE gel showing step-wise assembly of RNA tetrahedrons. "+" indicates the presence of the strands. M: ultralow range DNA Ladder. FIGS. 1E-1F show representative Atomic force microscopy (AFM) images (FIG. 1E) and single-particle cryo-EM 3D reconstruction (FIG. 1F) of 8 nm RNA tetrahedrons.

FIG. 2C shows a melting curve of RNA tetrahedron complex and each of the four component strands. FIG. 2D shows a comparison of melting curves for RNA, 2'-F and DNA tetrahedrons.

FIG. 3A shows a schematic showing tunable size conversion (from 22 bp per edge to 55 bp per edge) of RNA tetrahedrons. FIG. 3B shows an image of a representative 6% native PAGE gel showing step-wise assembly of larger RNA tetrahedrons. "+" indicates the presence of the strands. M: 100 bp DNA ladder. Ig. 3C shows the results of a DLS assay showing the hydrodynamic size of larger RNA tetrahedrons. FIGS. 3D-3E show AFM images (FIG. 3D) and (FIG. 3E) cryo-EM images and 3D reconstruction of RNA tetrahedrons.

FIG. 4A shows a schematic showing multifunctional RNA tetrahedrons harboring HBV ribozyme, MG aptamer, Spinach aptamer, and STV aptamer. FIG. 4B shows am image of a representative 7% native PAGE gel showing step-wise assembly of multifunctional RNA tetrahedrons. "+" indicates the presence of the strands. FIG. 4C shows the results of a ribozyme activity assay demonstrating cleavage of 135 nt substrate. Fluorogenic assay demonstrating fluorescence emission of (FIG. 4D) MG aptamer and (FIG. 4E) Spinach aptamer. FIG. 4F shows the results of a Streptavidin (STV) aptamer binding assay using STV affinity column.

FIG. 5A shows representative confocal images demonstrating RNA tetrahedron (with and without EGFR aptamers) binding to MDA-MB-231 cells. FIG. 5B demonstrates luciferase siRNA silencing effects as assayed by a dual luciferase assay. The error bars indicate mean±SD. FIG. 5C shows the results of a biodistribution assay in orthotopic MDA-MB-231 tumor-bearing mice after systemic tail vein injection of RNA tetrahedrons harboring EGFR aptamers.

FIG. 6A shows an embodiments of the fabrication of the triangle nanoprism from two planar equilateral RNA triangles. The triangle prism nanostructure forms by hybridization of the flexible 21 nt ssRNA "arms" of each triangles. The overall prismoidal construct contains the preserved geometry of the pRNA 3WJ structural building block. FIG. 6B shows a computer model structure of the triangular nanoprism demonstrating its average dimension in 3D space.

FIG. 7A demonstrates assembly efficiency of the RNA triangle nanoprism complex evaluated by 6% native polyacrylamide gel electrophoresis (PAGE). Step-wise association of the 8 RNA strands (0.5 µM each) into the final complex was conducted in 1×TMS buffer using one-pot assembly. FIG. 7B demonstrates the typical dynamic light scattering (DLS) data demonstrating average hydrodynamic diameter of the prism. FIG. 7C shows representative AFM images of the triangle nanoprism (5 nM) taken in air. FIG. 7D shows a representative CryoEM image of the large (10 nm) triangular RNA prism. Each white box indicates an individual RNA complex. Class averages of RNA nanoprisms as observed by cryo-EM. Reconstructed three-dimensional nanoprism at 2.5 nm resolution. FIG. 7E shows a representative CryoEM image of the small (5 nm) triangular RNA prism. Each white box indicates an individual RNA complex. Class averages of RNA nanoprisms as observed by cryo-EM. Reconstructed three-dimensional nanoprism at 2.2 nm resolution.

FIG. 8A shows an embodiment of a schematic design approach for the RNA MGA encapsulation. The RNA MGA sequence is embedded within the 3'-end of D and d' strands. Upon hybridization MGA folds into native conformation. FIG. 8B shows a schematic representation of the RNase T1 protection experiment demonstrating the relative dimensions of RNase T1 and nanoprisms. FIG. 8C shows assembly efficiency and relative migration of the triangle prisms on native 6% PAGE. The smaller RNA prism migrates much faster compared to the regular prism and emits fluorescence signal indicating proper folding of the functional RNA complex. Lane "L" is 100 bp DNA ladder (Thermo Scientific). FIG. 8D demonstrates the time-dependent fluorescence emission profile of the 0.1 µM RNA MGA aptamer in the presence of 500 U of RNase T1 and its absence (control). FIG. 8E demonstrates the remaining fluorescence signal of the triangle prisms after one hour of RNase T1 treatment. FIG. 8F shows a graph that can demonstrate the fluorescence properties of the complexes demonstrated in FIG. 8B.

FIG. 9A shows representative gel images of nanoprisms with different percentages of 2'-F modified pyrimidines used during assembly. Nanoprisms of 200 nM concentration were incubated in 2% FBS solution and analyzed by 3% agarose gel. FIG. 9B demonstrates prism relative gel band intensity plotted versus time. The intensity of each band was compared to the zero time point for each nanoprism.

FIG. 10A shows representative confocal microscopy images of KB cells incubated with RNA nanoprism decorated with 5 folates as targeting modules. FIG. 10B demonstrates TNF-α cytokine induction by the RNA nanoprism harboring different number of CpG-ODN per nanoparticle. Experiments conducted using macrophage-like RAW264.7 cells showing that cytokine secretion increases with the number of CpG payload per nanovehicles. The error bar obtained through three independent experiments.

FIG. 11A demonstrates methods that were developed to tune the interior angle of polygon from 60°→90°→108°. FIG. 11B demonstrates simple methods to change the size of RNA squares. FIGS. 11C-11D demonstrate a variety of RNA nanocages that have been constructed; illustration (left) and AFM images (right).

FIG. 14A shows a crystal structure of the 3WJ of pRNA composed of three strands. FIG. 14B shows a three dimensional structure of pyramid-shaped RNA nanocage with four 3WJs at the bottom and one four-way junction at the vertex. FIG. 14C shows a representative native PAGE assembly gel showing the step-wise assembly of RNA pyramid. FIG. 14D shows a melting temperature profile of RNA pyramid nanoparticles characterized by TGGE. FIG. 14E demonstrates the size of the RNA pentahedron determined by dynamic light scattering (DLS). FIG. 14F demonstrates the zeta potential of the RNA pyramid.

FIG. 15A shows a raw cryoEM (cryogenic electron microscopy) image. White boxes indicate individual RNA pyramid. FIG. 15B demonstrates a comparison between individual raw particles and computer-generated two-dimensional projections of the 3D model in similar orientations. FIG. 15C shows four views of the pentahedron model reconstructed from cryoEM images.

FIG. 20A shows a schematic illustration of the DNA-drug enacapsulation mechanism shown the hybridization of the oligonucleotide-drug conjugates within the inner cavity of the triangle prism. FIG. 20B shows images of representative gels demonstrating the results of a native PAGE analysis of the DNA-drug encapsultated complexes. The bottom image shows a gel scanned using the Cy5 channel and demonstrates a positive signal from the DNA-Cy5 conjugated. Lane "L" is the DNA ladder (Thermo Scientific GeneRuler Low Range).

FIGS. 22A-22C can demonstrate serum stability of 2' modified RNA nanocages. Serum stability was assayed in 10% FBS for (FIG. 22A) 2'-F RNa tetrahedrons and (FIG. 22B) unmodified RNA tetrahedrons. FIG. 22C shows a graph demonstrating the quantification of intact particles of FIGS. 22A-22B using Image J software.

FIG. 28 shows a table demonstrating the tilt geometry computed for tilt pair of images, using the final 3D model of the 17 nm RNA tetrahedron.

FIG. 29 shows RNA sequences of various functional modules that can be incorporated into the RNA nanocages described herein.

DETAILED DESCRIPTION

Figure 1A:
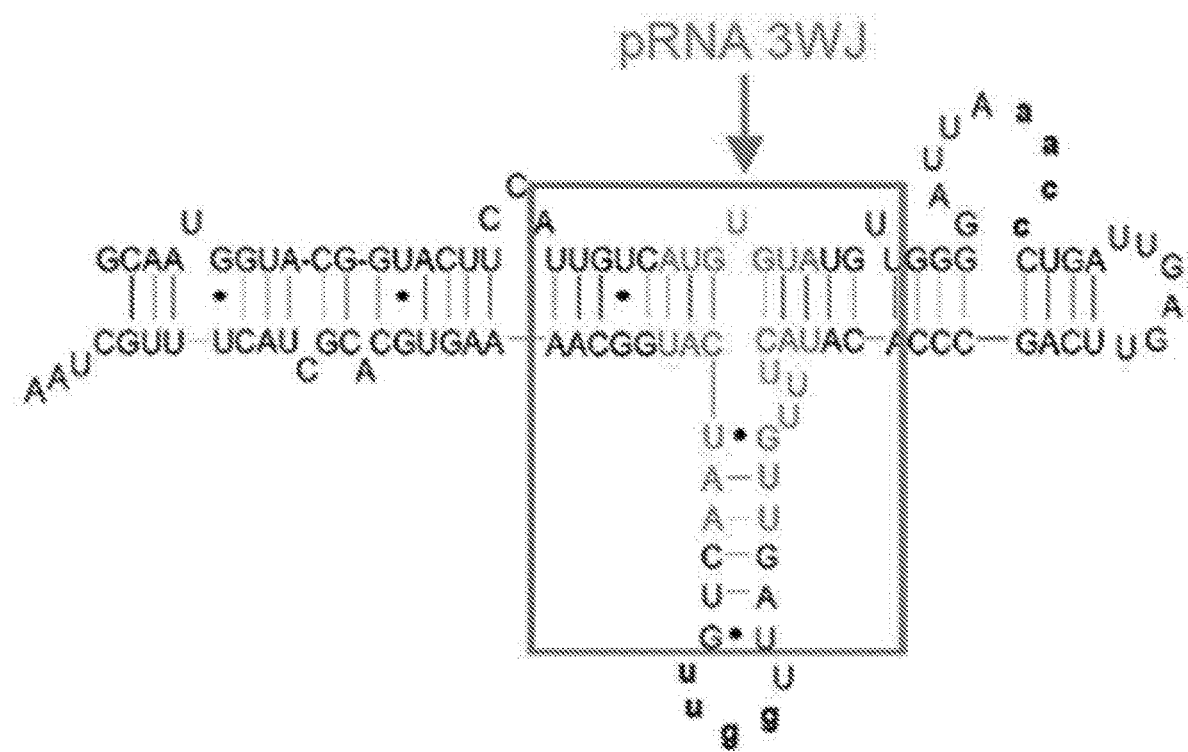
FIGS. 1A-1F can demonstrate the design and assembly of 8 nm RNA tetrahedrons.

The disclosed subject matter can be understood more readily by reference to the following detailed description, the Figures, and the examples included herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It is understood that the disclosed methods and systems are not limited to the particular methodology, protocols, and systems described as these may vary. It is also to be understood that the terminology used herein is for the purpose of describing particular embodiments only, and is not intended to limit the scope of the present invention which will be limited only by the appended claims.

Definitions

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and can also include any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "anti-cancer" or "anti-neoplastic" drug refers to one or more drugs that can be used to treat cancer and/or aberrant cell growth. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate;

Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators;

single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tel telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Therapeutic agents, as used herein, can include anticancer agents. The majority of anticancer agents can be divided in to: alkylating agents (e.g., cisplatin, carboplatin, oxaliplatin, mechloethamine, cyclophosphamide, chlorambucil), antimetabolites (e.g., azathioprine, mercaptopurine), anthracyclines, plant alkaloids and terpenoids (e.g., vinca alkaloids (e.g., vincristine, vinblastine, vinorelbine, vindesine, and podophyllotoxin) and taxanes (e.g., paclitaxel and docetaxel), topoisomerase inhibitors (e.g., irinotecan, topotecan, amsacrine, etoposide, etoposide phosphate, and teniposide), monoclonal antibodies (e.g., trastuzumab, cetuximab, rituximab, bevacizumab), other antitumour agents (e.g., dactinomycin), and hormonal therapy (e.g., steroids such as dexamethasone, finasteride, aromatase inhibitors, and gonadotropin-releasing hormone agonists).

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

As used herein, the term "nanoparticle" or "nanocage" is meant to refer to a particle between 10 nm and 200 nm in size. The nanocage can be between 10 nm and 50 nm, between 10 nm and 40 nm, between 10 nm and 30 nm, between 10 nm, and 20 nm, and 10 nm and 15 nm. The RNA can be obtained from any source, for example bacteriophages phi 29, HIV, Drosophila, the ribosome, or be a synthetic RNA.

As used herein, the term "nanotube" is meant to refer to the assembly of nanoparticles from RNA into a two or three dimensional structure. The assembly of nano-particles in to nanotubes can be by a process of self-assembly. Self-assembly can occur by ligation, chemical conjugation, covalent linkage, and non-covalent interactions of RNA, especially in the formation of RNA multimeric complexes.

As used herein, the term "motif" in reference to a nanoparticle or nanocage is meant to refer to a double-stranded or single-stranded ribonucleic acid or analog thereof. Individual motifs are joined together into larger particles by attachment to each other. Attachment can occur by non-covalent linking.

"Self-assembly" can refer to the ability of nucleic acids (and, in some instances, preformed nucleic acid nanostructures (e.g., crystals)) to anneal to each other, in a sequence-specific manner, in a predicted manner and without external control. In some embodiments, nucleic acid nanostructure self-assembly methods include combining nucleic acids (e.g; single-stranded nucleic acids, or oligonucleotides) in a single vessel and allowing the nucleic acids to anneal to each other, based on sequence complementarity. In some embodiments, this annealing process involves placing the nucleic acids at an elevated temperature and then reducing the temperature gradually in order to favor sequence-specific binding. Various nucleic acid nanostructures or self-assembly methods are known and described herein.

As used herein, "active agent" or "active ingredient" refers to a component or components of a composition to which the whole or part of the effect of the composition is attributed.

As used herein "anti-infectives" can include, but are not limited to, antibiotics, antibacterials, antifungals, antivirals, and antiproatozoals.

As used herein, "control" is an alternative subject or sample used in an experiment for comparison purposes and included to minimize or distinguish the effect of variables other than an independent variable. A "control" can be positive or negative.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein "immunomodulator," refers to an agent, such as a therapeutic agent, which is capable of modulating or regulating one or more immune function or response.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers.

Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA. As used herein, "expression" can refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. Techniques and methods appropriate for determining an amount of expression will be instantly appreciated by those of ordinary skill in the art and include, but are not limited to, western blotting for the transcribed protein, pyro-sequencing, polymerase chain reaction (PCR) based methods (e.g. reverse transcription PCR and quantitative real-time PCR), and mass-spectrometric based analysis.

As used herein, "gene" can refer to a hereditary unit corresponding to a sequence of DNA that occupies a specific location on a chromosome and that contains the genetic instruction for a characteristic(s) or trait(s) in an organism. The term gene can refer to both translated and untranslated regions of a subject's genome.

As used herein, "identity," "identical to", and the like can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H G., Eds., Humana Press, New Jersey, 1994; Sequence Analysis in Molecular Biology, von Heinje, G., Academic Press, 1987; and Sequence Analysis Primer, Gribskov, M and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. As used herein, "nucleic acid sequence" and "oligonucleotide" also encompasses a nucleic acid and polynucleotide as defined above.

Discussion

Disclosed are the components to be used to prepare a composition disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

As used herein, "molecular weight" can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

All patents, patent applications, and other scientific or technical writings referred to anywhere herein are incorporated by reference in their entirety. The disclosed subject matter can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

RNA nanotechnology has been progressively applied to generate 1D and 2D architectures via self-assembly of modular building blocks. However, 1D and 2D structures have limited capacity for use as a cargo delivery compounds. While 3D RNA based structures have been generated, significant challenges have limited their development such that, none currently exist that are degradation resistant, have precisely controlled shapes, can effectively encapsulate cargo molecules and, and can provide tunable and controlled cargo compound delivery.

With the deficiencies of current RNA nanotechnologies in mind, provided herein are RNA nanocages that are three dimensional (3D) structures that can be composed of RNA and can be configured to encapsulate a cargo compound. The RNA nanocages can further include a functional moiety. Also provided herein are pharmaceutical formulations that can contain one or more of the RNA nanocages provided herein. Methods of using the RNA nanocages and pharmaceutical formulations thereof are also provided herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

RNA Nanocages
RNA Nanocages

Provided herein are three dimensional ribonucleic acid nanostructures (also referred to herein as RNA nanocages) that are 3D structures composed of multiple RNA strands (e.g. polyribonucleotides). The RNA nanocages can be configured such that they self-assemble from the RNA strands that form the RNA nanocages. To form the RNA nanostructures each RNA strand can be complementary to only one other RNA strand. The complementary RNA strands specifically bind to each other to form duplex RNA and causing the RNA nanostructures to self-assemble. As such, it will be appreciated that RNA strand can be any desired sequence so long as it is configured to allow for specific self-assembly into the RNA nanocage. As such, it will be appreciated that the specific sequences presented herein are for example and the skilled artisan will be able to use tools and technique generally known in the art to design the specific polynucleotide sequence for any desired RNA nanocage in view of this disclosure. This is discussed in greater detail elsewhere herein. The RNA nanostructures can contain one ore more pRNA three-way junction (3WJ)s to connect the RNA strands and provide for a stable RNA nanostructure. In some embodiments, each RNA strand is attached to at least one pRNA 3WJ The exact size of the RNA nanocages is a function of the size of the RNA strands and 3WJs. In some embodiments, all of the RNA strands are the same length. In some embodiments, least two of the RNA strands that form the RNA nanocage are different lengths (have a different number of ribonucleotides) from each other. The number of ribonucleotides in each RNA strand can range from about 5 ribonucleotides to about 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1000, or more and any integer in between.

The RNA nanocages can be measured along an x-axis, a y-axis and a z-axis. The RNA nanocages can have a height, width, and length. In some aspects the largest dimension (height, width, length, diameter, etc. as appropriate) of the RNA nanocage can range from about 3 nm to about 100 nm, about 5 nm to about 30 nm, 10 nm, to about 75 nm, about 10 nm to about 50 nm, about 10 nm to about 40 nm, 10 nm to about 30 nm, 10 nm to about 20 nm, 10 nm to about 15 nm. The size (e.g. the largest dimension) of the RNA nanocage can be such that it is able to encapsulate a cargo molecule and yet evade immune detection when administered to a subject The RNA nanocage can be uniform in height, length, and/or width or it may be non-uniform in height, length, and/or width.

The specific choices of length of each RNA strand, number of 3WJ's, and number of strands can allow for the precise design of the shape of the RNA nanocage. Specific design strategies are describe elsewhere herein. The RNA nanocage can be any desired 3D shape. Specifically contemplated herein are prisms as well as tetrahedrons, cubes, and dodecahedrons. One of ordinary skill in the art will appreciate other 3D structures in view of this disclosure and Examples provided herein.

The RNA nanocage, in some embodiments, can be assembled from more than one two-dimensional nucleic acid nanostructure (e.g., more than one layer of nucleic acids (e.g. ribonucleic acids) or more than one three-dimensional nucleic acid nanostructure (e.g., more than one "pre-assembled" nucleic acid nanostructure that is linked to one or more other "pre-assembled" nucleic acid nanostructure).

The ribonucleotides that form the RNA strands can be 2' modified. In some embodiments, the modification can alter the stability of the RNA strand and/or RNA nanocage, alter the sensitivity of an RNA strand and/or RNA nanocage to an enzyme, such as an RNAse (e.g. RNAse I). In some embodiments, one or more ribonucleotides that form the RNA strand(s) contains a 2'-Fluoro (2'F) modification. In this modification, a 2'fluoro is substituted for a 2'-hydroxyl group in a ribonucleotide. In other embodiments, the RNA strand(s) can be 2' OME (2' 0-Methyl), LNA (locked nucleic acid), and/or phospholiolate modified. 2'OME modifications are ribonucleotides that are modified at the 2' position with an —O-Methyl group. The 2' OME modification can prevent attack by single-stranded endonucleases. LNA, which is also referred to as inaccessible RNA, describes a ribonucleotide that is modified with an extra bridge connecting the 2' oxygen and the 4' carbon. The bridge can "lock" the ribose in the 3'-endo conformation.

Any ribonucleotide (A/U/G/C) can be 2' modified. By altering the amount of ribonucleotides in the RNA strands, the degradation profile and thus the release of any cargo molecule contained therein and/or encapsulated therein can be tuned. In some embodiments, the more ribonucleotides are 2'modified the faster the degradation of the RNA nanocage. In other embodiments, the more ribonucleotides that are 2' modified the slower the degradation of the RNA nanocage. Whether the modification makes the RNA nanocage more resistant to degradation or more susceptible, will depend in the modification made. The more ribonucleotides that are 2'F modified in the RNA nanocage the more resistant the RNA nanocage can be to RNAseI degradation.

The percentage of ribonucleotides that are 2' modified in an RNA nanocage can range from 0% about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

Composite RNA Nanocages

Two or more RNA nanocages can be operably linked to each other to form a composite RNA nanocage. The composite RNA nanocages can be homogenous (e.g. contain the same type of RNA nanocage) or heterogenous (contain at least two different RNA nanocage types). The RNA nanocages that form the composite RNA nanocage can be operably linked to each other via a linker. The linkers are typically not integral to the nucleic acid nanostructures, although they may be attached to the nanostructures through suitable functional groups. The ability to attach two or more RNA nanocages together allows structures of greater size (e.g. micrometer size) and/or complexity to be made. Examples of linkers for use in accordance with the present disclosure to operably couple two or more RNA nanocages together include, without limitation, chemical crosslinkers (e.g., glutaraldehyde), biomolecules (e.g. avidin-biotin), and ligand-functionalized nanoparticles/moieties (e.g., single-stranded-nucleic acid-functionalized nanoparticles). In some instances, the linkers may involve click chemistry or coordinating interaction (Ni2+/polyhistidine).

Functional Moieties

As discussed above, the RNA nanocage can include one or more functional moieties. The functional module can facilitate targeting the RNA nanocage to a specific cell-type, tissue-type, organ, or locale within a subject. The functional moiety can facilitate encapsulation of a cargo molecule within the RNA nanocage. The functional moiety can facilitate attaching the cargo molecule within or to the RNA nanocage. The functional moiety can be an aptamer. The functional moiety can be an antibody. The functional moiety can be a ligand for a receptor that can be expressed in or on a cell. The functional moiety can be a polynucleotide. The functional moiety can be an RNA molecule or a DNA molecule. The functional moiety can directly attached or integrated into an RNA strand that forms the RNA nanocage.

In some embodiments, the targeting moiety specifically targets a cancer cell. In some embodiments the In some embodiments, the targeting moiety is an EGFR, HER2, and/or EP-CAM aptamer or PSM antigen, or folate. In some embodiments, the targeting moiety is a ligand for EGFR. In other embodiments, the targeting moiety targets blood, lungs, kidneys, brain tissue, neurons, muscle, heart, tendons, ligaments, liver, pancreas, or other specific tissue.

In some embodiments, the functional moiety can be a stimulus responsive linker, such as a photocleavable linker, pH responsive linker, or a linker that is enzyme cleavable. Photocleable linkers are molecules that contain a photoliable group that is cleabable by a specific wavelength of light. The photocleavable linker can cleavably attach a cargo molecule or other functional moiety (e.g. a targeting moiety) to the RNA nanocage. This is another mechanism in which the release of a cargo molecule from the RNA nanocage can be tuned and controlled. The photocleavable linker can be activated (e.g. cleaved) via a source of electromagnetic radiation, including but not limited to, visible light, infared radiation, ultra-violet radiation. Use of a photocleavable linker can allow for time-controlled and spatial control of release of the cargo molecule from the RNA nanocage. Exemplary photocleavable linkers can include, but are not limited to phosphoramidites (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6888), photocleavable biotin (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6691); Photocleavable Amino C6 (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6890), photocleavable spacer (see e.g. see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6889); 2-nitrobenzyl linkers (see e.g. Bai et al., (2003) PNAS, 100: 409-413). Other suitable photocleavable linkers will be appreciated by those of ordinary skill in the art.

pH responsive linkers can be any compound that can degrade (e.g. hydrolyze) at a certain pH. Thus the pH responsive linkers can be acidic responsive or basic responsive. Th pH responsive linkers can be polymers. Suitable pH responsive linkers are generally known in the art and include, but are not limited to those described in Choy et al. (Bioconjugate. Chem. (2016) 27:824-830; Schmaljohann (2008) Adv. Drug Deliv. Rev. (2006) 58:1655-1670, Balamuralidhara et al. (2011) Am. J. Drug Disc. Devel. 1:24-48;

Biomedical Nanomaterials, ed. Zhao and Shen (2016), Chapter 6; Masson et al. (2004) J. Control Release. 99:423-434; Karimi et al., Nanomed. and Nanobiotech. (2016) 8:696-716; International Patent Application Publication No.: WO2016/028700; and Patil et al., 2012. Int. J. Mol. Sci. 13:11681-11693.

Enzyme cleavable linkers are those that contain a cleavage site for an enzyme. In some embodiments the linkers can be a nucleic acid that contains a sequences for an endonuclease. Endonculease cleavage sites and how to produce nucleic acid molecules containing them will be appreciated by those of ordinary skill in the art. Other cleavage sites that can be contained can be RNAse or DNAse cleavage sites. In some embodiments, the enzyme cleavae site can be a cleavage site for an enzyme that is specific to a target cell. Thus in this way, release can be controlled such that it occurs only at the target cell via interaction with the target-cell specific enzyme. Other cleavage sites that can be incorporated into the enzyme cleavable linkers will be instantly appreciated by those of skill in the art.

Cargo Compounds

The RNA nanocages can contain one or more cargo compounds. The cargo compound(s) can be any biological molecule, chemical molecule, synthetic molecule, or any other molecule that can be encapsulated by or linked to, as described herein, the RNA nanocage described herein.

In some aspects, the cargo compound can be DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable cargo compounds include sensitizers, (e.g. radiosensitizers) that can make a cell or subject more responsive (or sensitive) to a treatment or prevention and imaging or other diagnostic agents. The RNA nanocages can be used as a monotherapy or in combination with other active agents for treatment or prevention of a disease or disorder.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepineph-rine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein Suitable sensitizing agents can include, but are not limited to, radiosensitizers, insulin sensitizers (e.g. metformin, thiazolidinediones,) and photosensitizers for photodynamic therapy (e.g. aminolevulinic acid (ALA), Silicon Phthalocyanine Pc 4, m-tetrahydroxyphenylchlorin (mTHPC) and mono-L-aspartyl chlorin e6 (NPe6)).

Suitable imaging agents include but are not limited to, fluorescent molecules (e.g. Cy3, Cy5, and other commercially available fluorflores), paramagnetic ions, nanoparticles that can contain a paramagnetic ion, super-paramagnetic iron oxide molecules and nanoparticles thereof, 18F-fluorodeoxyglucose and other PET imaging agents, gadolinium containing contrast agents, radionuclides and compositions thereof.

Self Assembly of the RNA nanocages. The fundamental principle for designing self-assembled nucleic acid nanostructures is that sequence complementarity in nucleic acid strands is encoded such that, by pairing up complementary segments, the nucleic acid strands self-organize into a predefined nanostructure under appropriate physical conditions. From this basic principle (see, e.g., Seeman N. C. J. Theor. Biol. 99: 237, 1982, incorporated by reference herein), researchers have created diverse synthetic nucleic acid nanostructures (see, e.g., Seeman N. C. Nature 421: 427, 2003; Shih W. M. et al. Curr. Opin. Struct. Biol. 20: 276, 2010, each of which is incorporated by reference herein). Examples of nucleic acid (e.g., DNA) nanostructures, and methods of producing such structures, that may be used in accordance with the present disclosure are known and include, without limitation, lattices (see, e.g., Winfree E. et al. Nature 394: 539, 1998; Yan H. et al. Science 301: 1882, 2003; Yan H. et al. Proc. Natl. Acad. of Sci. USA 100; 8103, 2003; Liu D. et al. J. Am. Chem. Soc. 126: 2324, 2004; Rothemund P. W. K. et al. PLoS Biology 2: 2041, 2004, each of which is incorporated by reference herein), ribbons (see, e.g., Park S. H. et al. Nano Lett. 5: 729, 2005; Yin P. et al. Science 321: 824, 2008, each of which is incorporated by reference herein), tubes (see, e.g., Yan H. Science, 2003; P. Yin, 2008, each of which is incorporated by reference herein), finite two-dimensional and three dimensional objects with defined shapes (see, e.g., Chen J. et al. Nature 350: 631, 1991; Rothemund P. W. K., Nature, 2006; He Y. et al. Nature 452: 198, 2008; Ke Y. et al. Nano. Lett. 9: 2445, 2009; Douglas S. M. et al. Nature 459: 414, 2009; Dietz H. et al. Science 325: 725, 2009; Andersen E. S. et al. Nature 459: 73, 2009; Liedl T. et al. Nature Nanotech. 5: 520, 2010; Han D. et al. Science 332: 342, 2011, each of which is incorporated by reference herein), and macroscopic crystals (see, e.g., Meng J. P. et al. Nature 461: 74, 2009, incorporated by reference herein). The RNA strands can be single-stranded nucleic acids, double-stranded nucleic acids, or a combination of single-stranded and double-stranded nucleic acids.

Methods of Making the RNA Nanocages

The RNA strands, functional moieties, can be synthesized using standard molecular biologic and biochemical techniques. In other words, the various nucleic acids that can form the RNA nanocages can be de novo synthesized as desired or be generated from various nucleic acid expression vectors, or transcribed in vitro. Such synthesis techniques will be known to the skilled artisan.

The RNA components (RNA strands and 3WJs can be designed using a computer aided design methodology described in the Examples herein. Although the computer design is demonstrated using a specific RNAnanocage, it will be appreciated that the principles taught therein will be able to be extrapolated to any desired RNA nanocage by the skilled artisan.

Pharmaceutical Formulations

Also provided herein are pharmaceutical formulations that can include an amount of a RNA nanocage described herein and a pharmaceutical carrier appropriate for administration to an individual in need thereof. The individual in need thereof can have or can be suspected of a cancer, a genetic disease or disorder, a viral, bacterial, fungal, and/or parasitic infection, or other disease or disorder in need of treatment or prevention. In some embodiments, the subject in need thereof is in need of a diagnostic procedure, such as an imaging procedure. The pharmaceutical formulations can include an amount of an RNA nanocage described herein, such as that can be effective to treat or prevent a cancer, a genetic disease or disorder, a viral, bacterial, fungal, and/or parasitic infection, or other disease or disorder or be effective to image the subject or a portion thereof.

Formulations can be administered via any suitable administration route. For example, the formulations (and/or compositions) can be administered to the subject in need thereof orally, intravenously, occularly, intraoccularly, intramuscularly, intravaginally, intraperitoneally, rectally, parenterally, topically, intranasally, or subcutaneously. Other suitable routes are described herein. In some embodiments, the RNA nanocage contains an effective amount of a cargo molecule.

Parenteral Formulations

The RNA nanocages can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the RNA nanocages as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the RNA nanocages.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the RNA nanocages in the required amount in the appropriate solvent or dispersion medium with one or more of the excipients listed above, as required, followed by filtered sterilization. Dispersions can be prepared by incorporating the various sterilized RNA nanocages into a sterile vehicle which contains the basic dispersion medium and the required other ingredients from those listed above. Sterile powders for the preparation of sterile injectable solutions can be prepared by vacuum-drying and freeze-drying techniques, which yields a powder of the RNA nanocages plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more N RNA nanocages. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The RNA nanocages as described herein can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the RNA nanocages can be administered as a liquid formulation, such as a solution or suspension, a semi-solid formulation, such as a lotion or ointment, or a solid formulation. In some embodiments, the RNA nanocages can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing a RNA nanocage as described herein are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing a RNA nanocage as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing a RNA nanocage as described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing a RNA nanocage as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, C12-C15 alkyl benzoates, mineral oil, squalane, cyclomethicone, capric/caprylic triglycerides, and combinations thereof.

Also described herein are foams that can include a RNA nanocage as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The RNA nanocages as described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing a RNA nanocages as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing a RNA nanocage as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing a RNA nanocage as described herein can be prepared as described in standard references such as "Pharmaceutical dosage form tablets", eds. Liberman. et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing a RNA nanocage as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing a RNA nanocage. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable additional active agents include, sensitizers (such as radiosensitizers). The RNA nanocages can be used as a monotherapy or in combination with other active agents for treatment or prevention of a disease or disorder.

Suitable hormones include, but are not limited to, aminoacid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, nonsteroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein.

Methods of Using the RNA Nanocages and Pharmaceutical Formulations Thereof

The RNA Nanocages and formulations there can be used to deliver one or more cargo compounds to a subject in need thereof or a cell. In some embodiments, the RNA nanocages can be used to deliver an RNA or DNA molecule for replacement gene/transcript therapy, deliver RNAi or similar RNA (e.g. microRNA) to a subject to specifically inhibit RNA transcripts to reduce gene expression of a specific gene or genes, deliver an imaging agent, delivering a small molecule drug, and/or deliver any other cargo compound that can be encapsulated in the RNA nanocages provided herein. Thus, the RNA nanocages can be used to deliver a treatment, prevention, and/or a diagnostic compound to a subject in need thereof.

In some embodiments, the RNA nanocages described herein can be contacted with a cell or population thereof. In some embodiments, the cell or population thereof is sensitized to the treatment or prevention being delivered by the RNA nanocage. In some embodiments, the RNA nanocage is delivering the sensitizing agent. In some aspects the cargo compound being delivered is not a sensitizing agent. In an aspect, following the administration of a RNA nanovage, a subject can be sensitized to treatment. In an aspect, an increased sensitivity or a reduced sensitivity to a treatment, such as a therapeutic treatment (such as that provided by a cargo compound being delivered by the RNA nanocage, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a sensitizing agent and/or the RNA nanocage (such as a RNA nanocage carrying a sensitizing agent) the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a sensitizing agent. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a sensitizing agent, such as one being delivered by an RNA nanocage described herein. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

In some embodiments, where the RNA nanocage includes a photocleavable linker that is linking the targeting moiety and/or cargo compound the RNA nanocage can be administered to the subject or population of cells. After administration, light can be applied to the region and/or population of cells in the subject in need thereof where treatment or prevention is needed to cause the release of the RNA nanocage and/or cargo molecule.

The RNA nanocages as provided herein can be administered to a subject in need thereof, cell, or population thereof. The subject in need thereof can have a cancer, genetic disease or discorder, a viral, bacterial, parasitic, and/or fungal infection, or any other disease or disorder that would benefit from an effective agent (such as a cargo compound described herein) being delivered. The amount delivered can be an effective amount of an RNA nanocage provided herein. The subject in need thereof can be symptomatic or asymptomatic. In some embodiments, the RNA nanocages provided herein can be co-administered with another active agent. It will be appreciated that co-administered can refer to an additional compound that is included in the formulation or provided in a dosage form separate from the RNA nanocage or formulation thereof. The effective amount of the RNA nanocage or formulation thereof, such as those described herein, can range from about 0.1 mg/kg to about 500 mg/kg. In some embodiments, the effective amount ranges from about 0.1 mg/kg to 10 mg/kg. In additional embodiments, the effective amount ranges from about 100 mg/kg. If further embodiments, the effective amount ranges from about 0.1 mg to about 1000 mg. In some embodiments, the effective amount can be about 500 mg to about 1000 mg.

Administration of the RNA nanocages and formulations thereof can be systemic or localized. The compounds and formulations described herein can be administered to the subject in need thereof one or more times per day. In an embodiment, the compound(s) and/or formulation(s) thereof can be administered once daily. In some embodiments, the compound(s) and/or formulation(s) thereof can be administered given once daily. In another embodiment, the compound(s) and/or formulation(s) thereof can be administered is administered twice daily. In some embodiments, when administered, an effective amount of the compounds and/or formulations are administered to the subject in need thereof. The compound(s) and/or formulation(s) thereof can be administered one or more times per week. In some embodiments the compound(s) and/or formulation(s) thereof can be administered 1 day per week. In other embodiments, the compound(s) and/or formulation(s) thereof can be administered 2 to 7 days per week.

In some embodiments, the RNA nanocage(s) and/or formulation(s) thereof, can be administered in a dosage form. The amount or effective amount of the compound(s) and/or formulation(s) thereof can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 0.1 to about 1000 mg per day. The effective amount in a dosage form can range from about 0.1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

EXAMPLES

The following examples are put forth so as to provide those of ordinary skill in the art with a complete disclosure and description of how the compounds, compositions, and methods claimed herein are used and evaluated and are intended to be purely exemplary of the disclosed subject matter and are not intended to limit the scope of what the inventors regard as their invention. However, those of skill in the art should, in light of the present disclosure, appreciate that many changes can be made in the specific aspects which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Controllable Self-Assembly of RNA Tetrahedrons with Precise Shape and Size for Cancer Targeting The Watson-Crick base paring properties of DNA and RNA have led to their development as excellent building blocks for the construction of nanomaterials by bottom-up self-assembly.[1-6] For constructing larger architectures by directional or angular extension, it is necessary to extend the building blocks with a defined angle or orientation. This has been challenging for DNA since one helix turn of 360° is 10.5 nucleotides for the regular B-DNA. A non-integer per helix turn will result in the twisting of the extension angle or the restriction in orientation control. In RNA, the number of nucleotides per helix turn is an integer of 11 for A-form RNA, which is a common structure for most RNA sequences. This unique property of RNA can enable RNA structural growth with precise one directional control, which can facilitate the construction of large size architectures for materials science, computer device, and biomedical applications.

RNA nanotechnology is an emerging field that involves the design, construction, and functionalization of nanometer-scale particles composed mainly of RNA for applications in biomedical and material sciences.[1] Previous reports have shown that a variety of RNA nanostructures can be constructed with defined sizes, shapes, and stoichiometry, including triangles,[7] squares,[8-10] bundles,[11,12] 2D arrays,[7,13] hexamers,[14-16] and 3D cages[17-19] by bottom-up self-assembly based on intra- and inter-RNA interactions. We have extensively utilized the structural features of bacteriophage phi29 packaging RNA[20] to construct varieties of RNA nanoparticles via loop-loop interactions,[11,14,21,22] palindrome sequence mediated foot-to-foot interactions,[11,21] and three-way junction (3WJ) motif.[7,21,23-25] More recently, 2D polygons such as triangle, square, and pentagon[25] were constructed using the pRNA-3WJ as core scaffold at the vertices. This 2D work was extended to design and construct 3D RNA nanoparticles with controllable shape and size.

Tetrahedral geometry is attractive because of their intrinsic mechanical rigidity and structural stability. It is a pyramid-like structure with four triangular faces and six edges. Several methods have been used to construct DNA based tetrahedrons, such as an origami approach based on a long single DNA strand,[26] complementary hybridization of strands using sticky ends,[27,28] and hierarchical assembly of tiles.[29] RNA is an attractive alternative building block due to its high thermal stability[30,31] and versatility in structures[1,32] well beyond the simplistic canonical Watson-Crick base pairing in DNA nanostructures. Herein, the well-characterized ultrastable 3WJ motif[15,23] was used as core scaffold to construct tetrahedral architectures. The RNA tetrahedrons have defined 3D structure as revealed by atomic force microscope (AFM), as well as by single-particle cryo-electron microscopy (cryo-EM) that has long been found to be very challenging in imaging pure RNA structures without forming complex with proteins.[33] Moreover, for the functionalization of the RNA tetrahedrons, aptamers, ribozyme, and siRNA were placed at the edges of the RNA tetrahedrons with high precision without disrupting the overall structure. Importantly, the functional modules were incorporated prior to the assembly of the RNA tetrahedrons to ensure the production of homogeneous nanoparticles with high yield. Biodistribution studies revealed that RNA tetrahedrons functionalized with EGFR-targeting RNA aptamer specifically targeted orthotopic breast tumors without detectable accumulation in healthy vital organs. The RNA tetrahedrons are envisioned to have a broad impact in nanotechnology arena, such as for organizing nanoscale materials with high precision, encapsulation of functional materials within its hollow cavity, targeted therapy to diseased cells, and as image-guided delivery vectors.

Figure 1C:
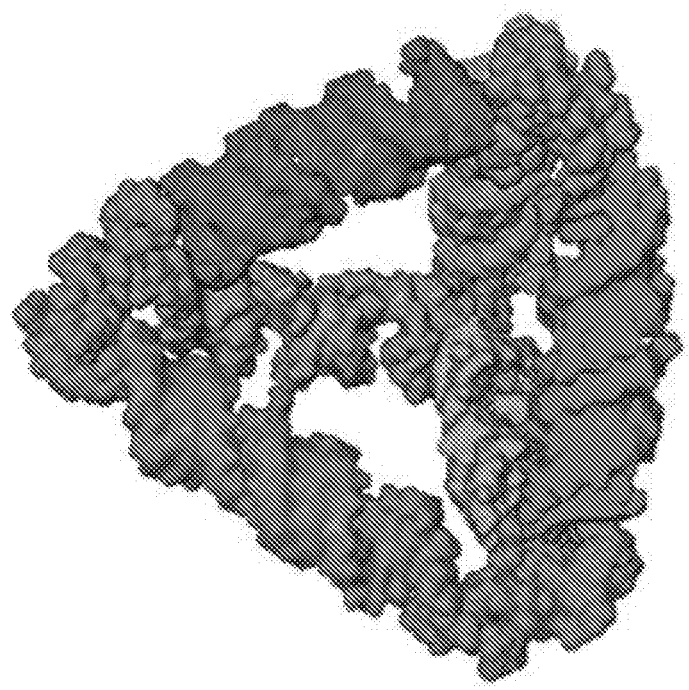
Figure 1B:
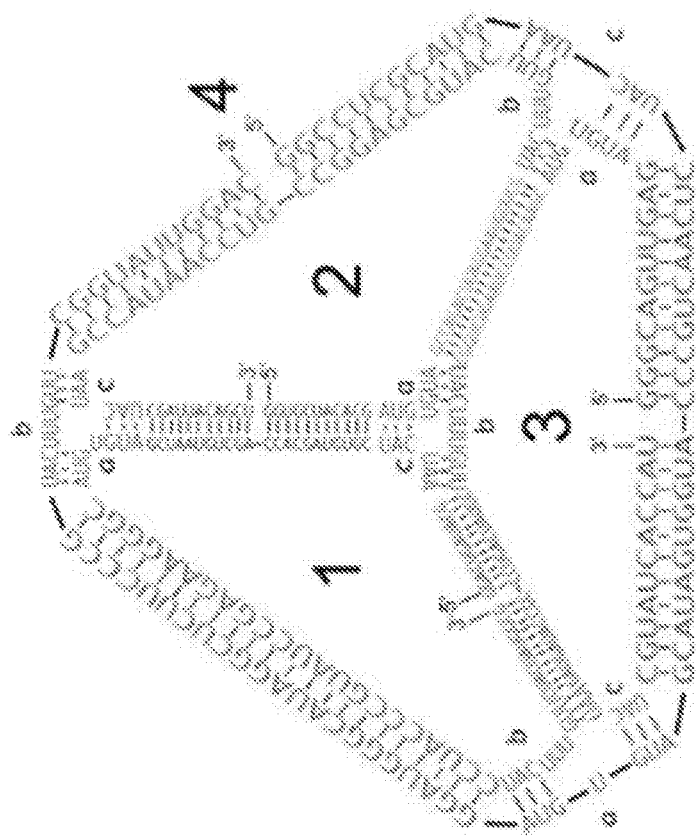
Figure 1D:
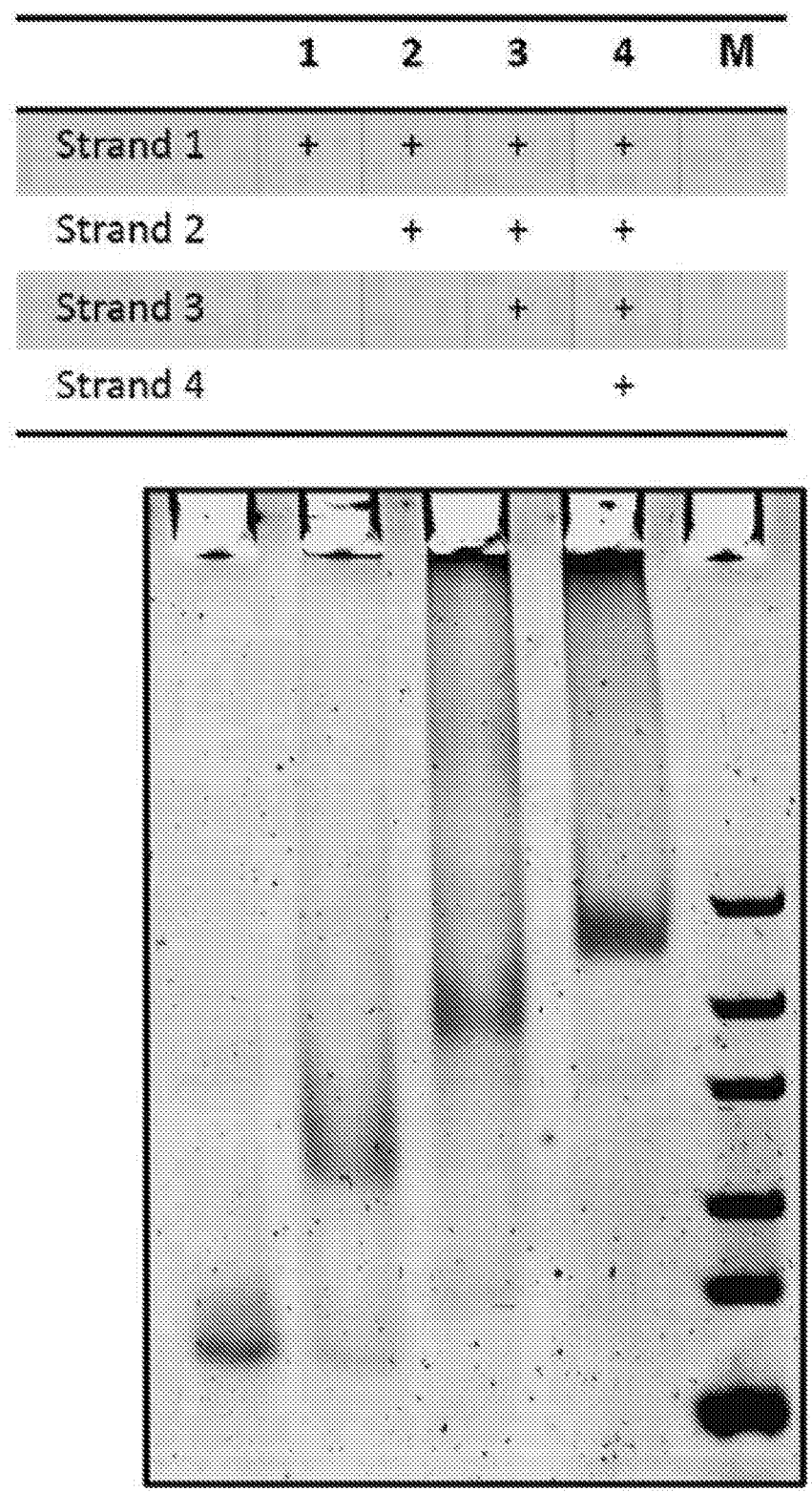

In this study, the pRNA-3WJ motif[15,23] (FIG. 1A) was used as a core module and placed at each of the four vertices to build RNA tetrahedrons (FIG. 1B). A total of four RNA strands were designed consisting of four pRNA 3WJ core sequences and six linking RNA sequences. A 3D model of the RNA tetrahedron (FIG. 1B) was then generated using computational modeling software UCSF Chimera,[34] Swiss PDB Viewer, and PyMOL Molecular Graphics System. The resulting computational model exhibited authentic tetrahedral conformation. For assembling the RNA tetrahedrons, the four RNA strands were synthesized by in vitro transcription and then mixed in stoichiometric ratio and annealed in 1× Tris buffer in a one-pot manner. Step-wise assembly of the complex was observed by native polyacrylamide gel electrophoresis (PAGE) (FIG. 1D). FIGS. 29-31 show RNA sequences for the various strands and functional modules used in the 8 nm and 17 nm RNA tetrahedrons discussed in this Example.

Figure 1E:
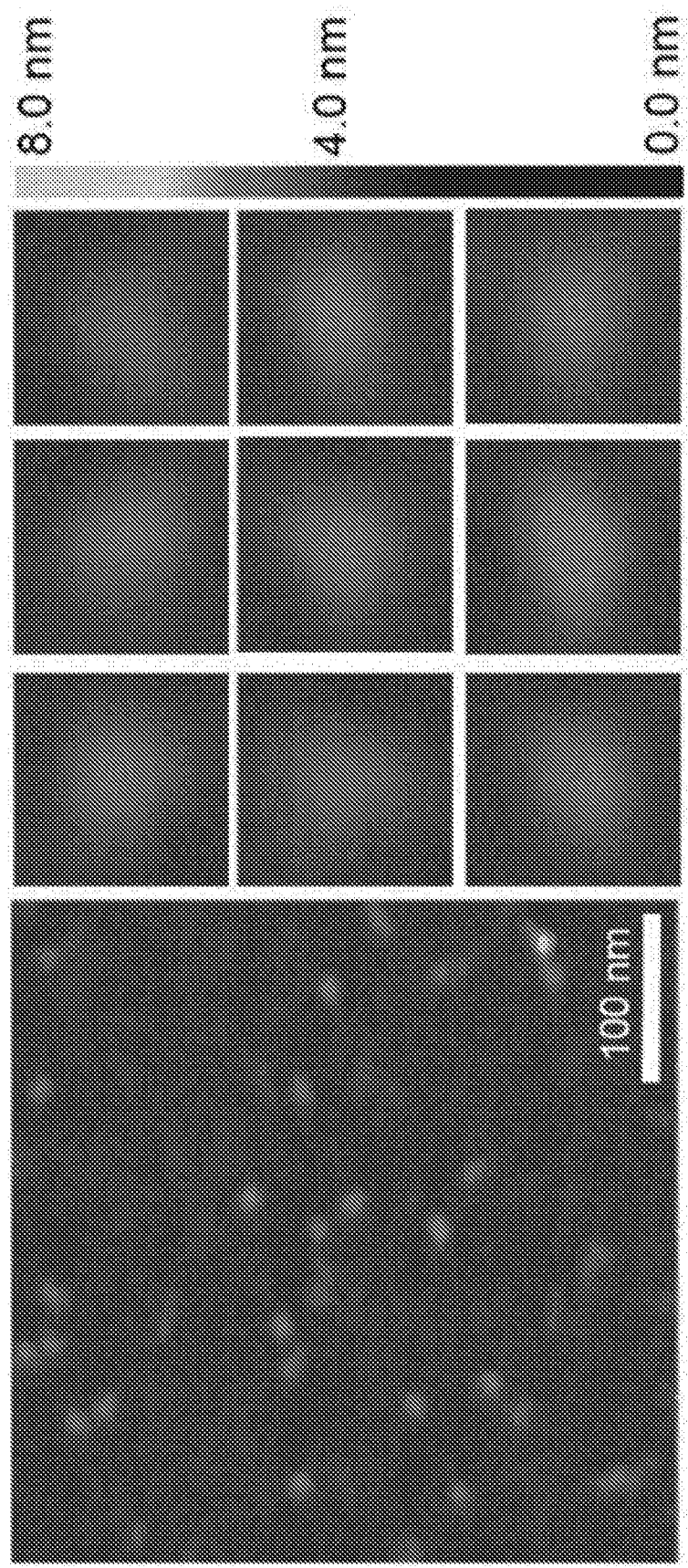
Figure 1F:
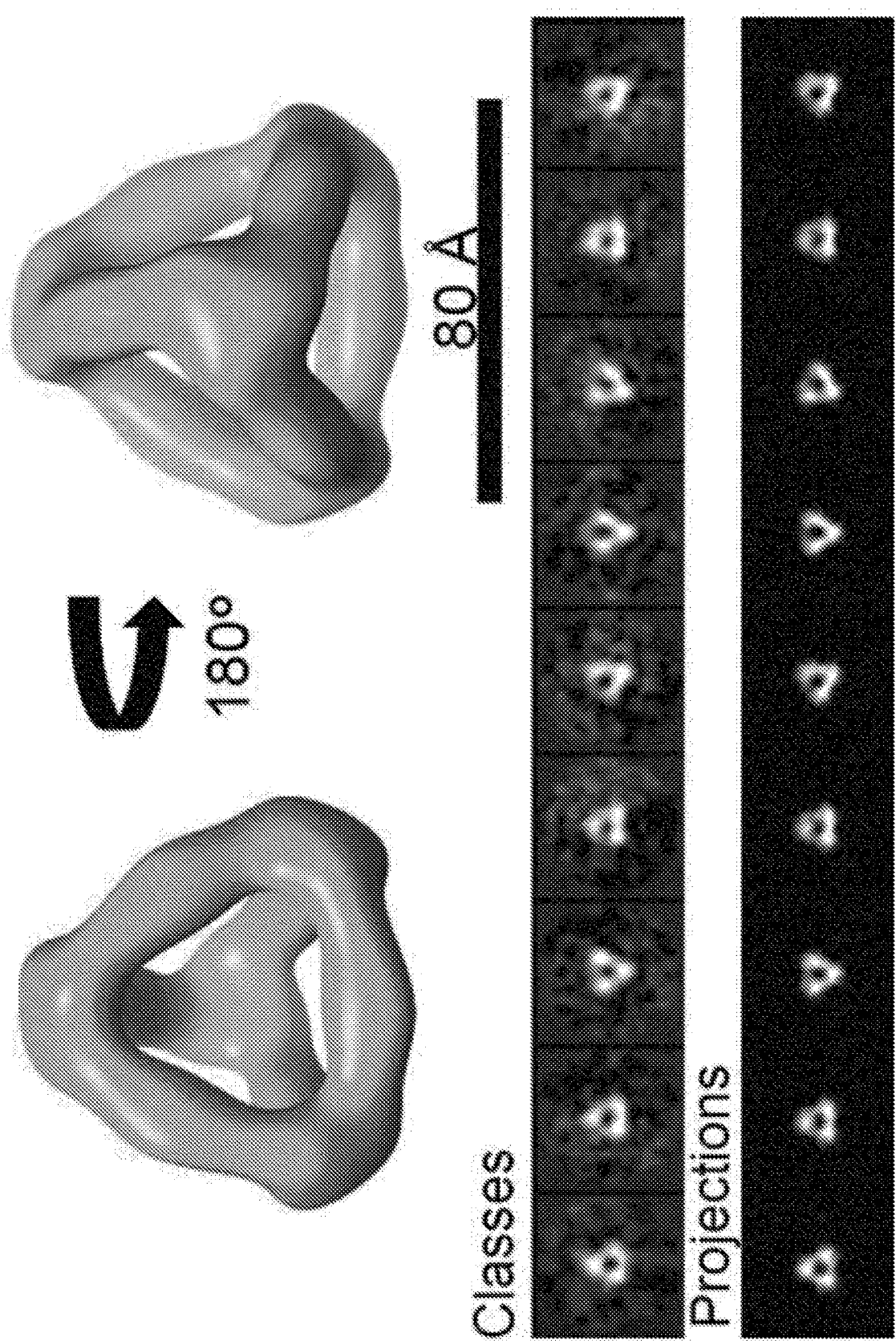
Figures 2A, 2B:
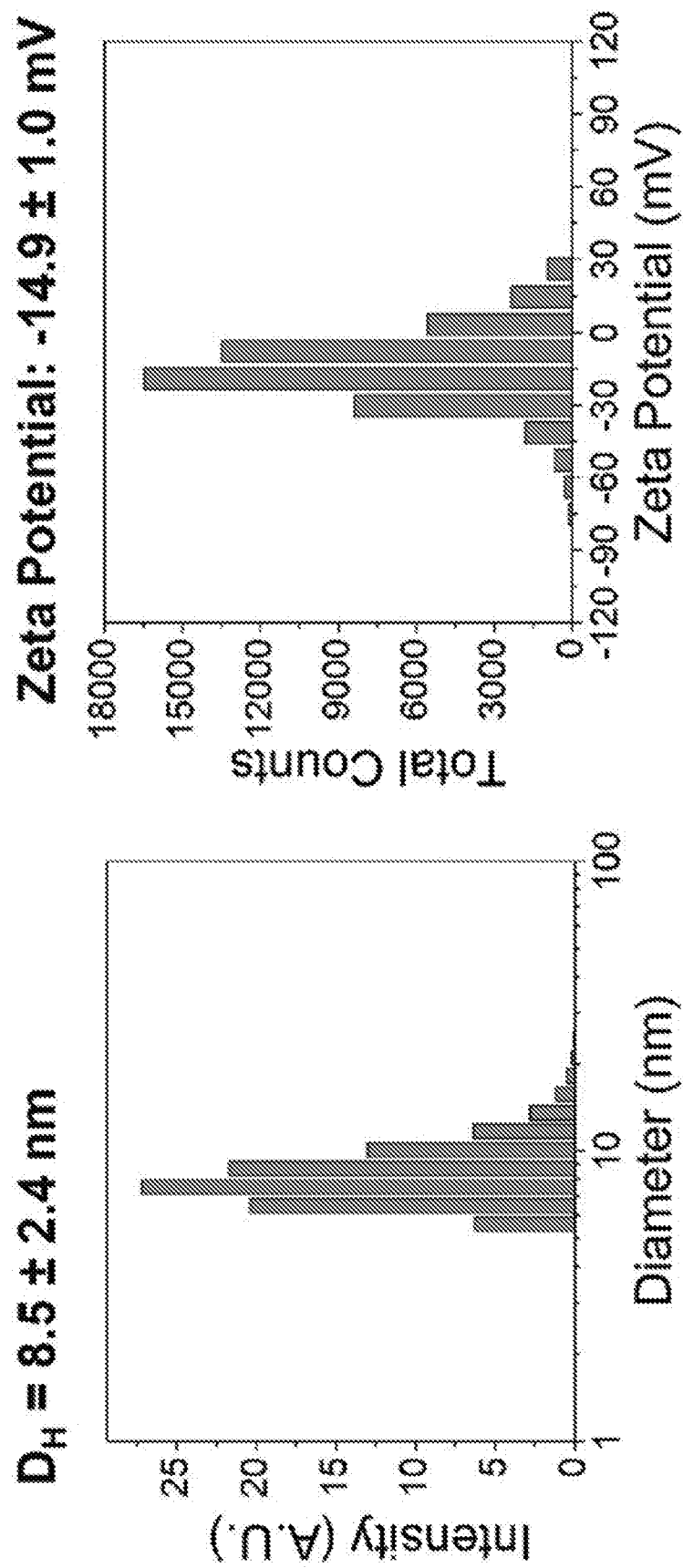
FIGS. 2A-2D demonstrate the physiochemical characterization of RNA tetrahedrons. Dynamic light scattering (DLS) assay showing (FIG. 2A) the hydrodynamic size and (FIG. 2B) the zeta potential of RNA tetrahedrons.
Figure 2D:
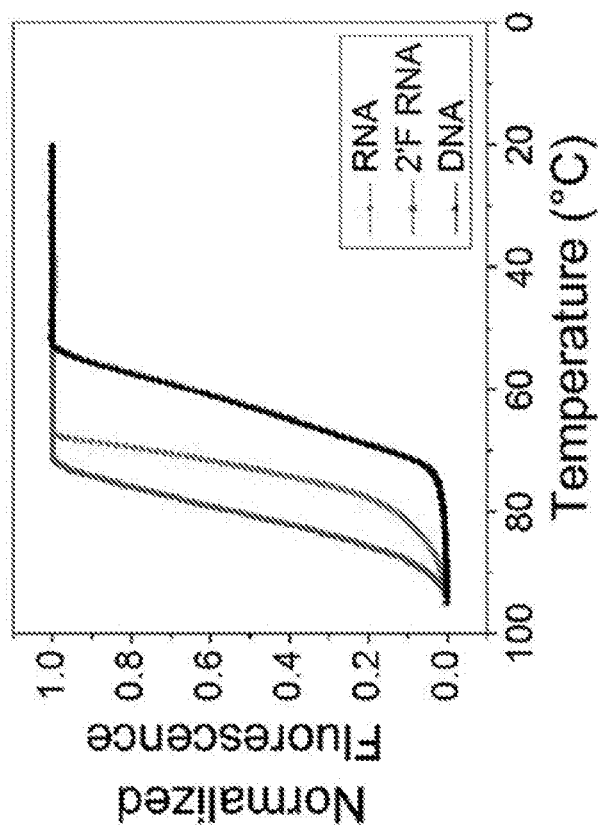
Figure 2C:
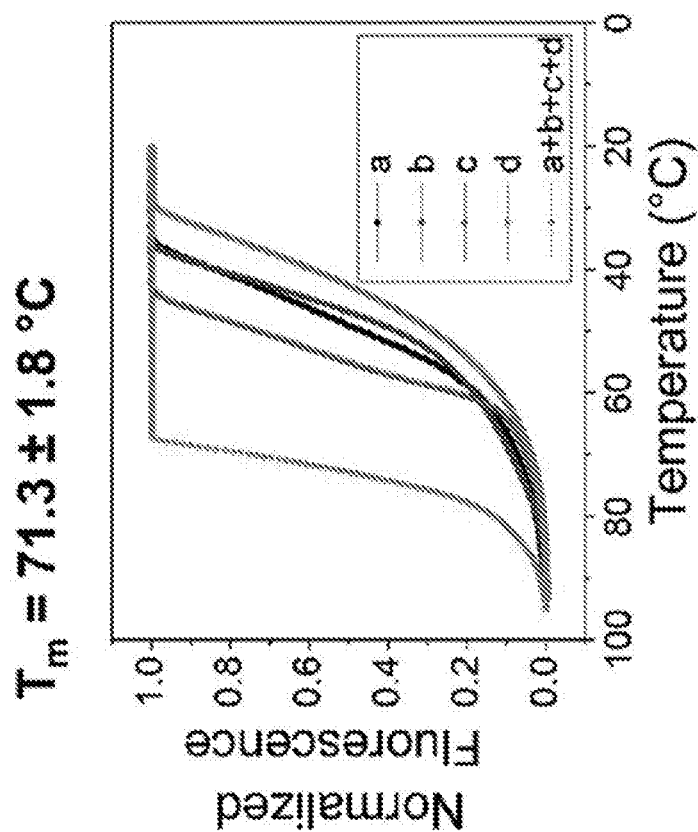
Figure 21A:
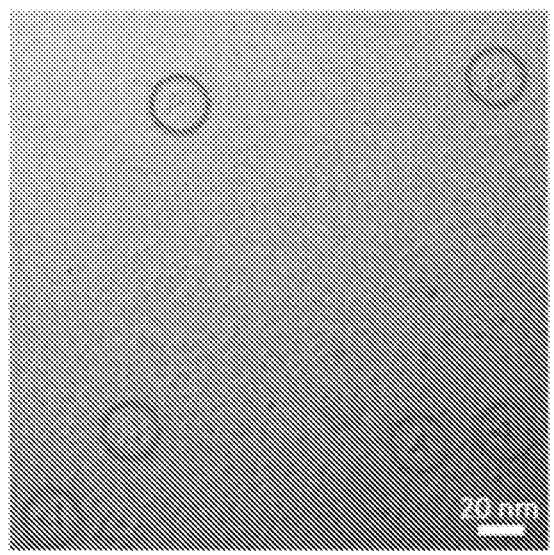
FIGS. 21A-21C show (FIG. 21A Cryo-EM raw images of the 8 nm tetrahedrons, (FIG. 21B) reference free 2D class averages of the 8 nm tetrahedrons, and (FIG. 21C) 0.143 Fourier shell correlation.
Figure 21B:
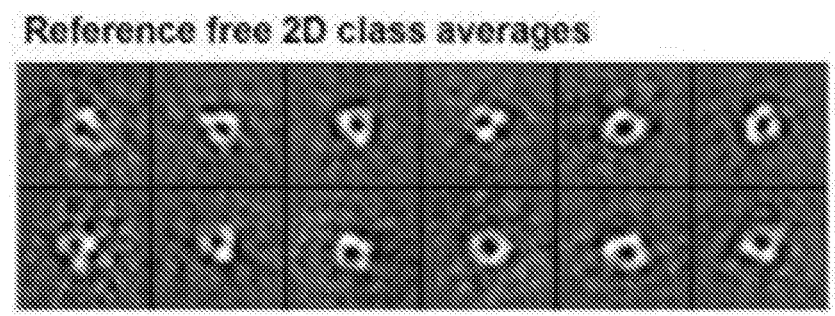
Figure 21C:
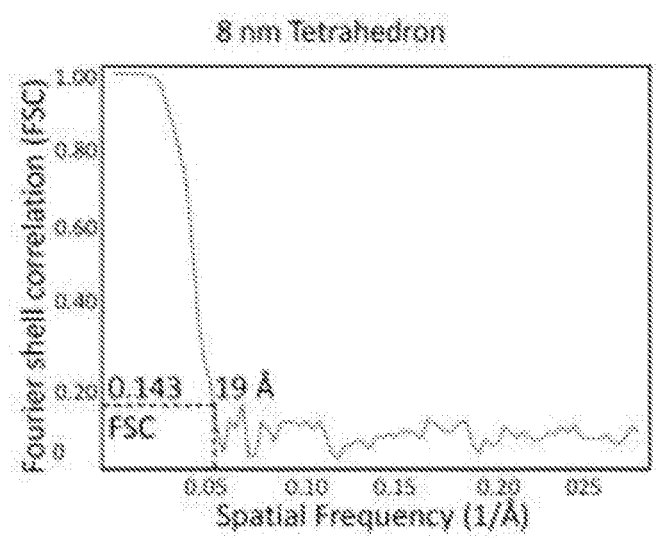

For 3D RNA tetrahedrons, the most convincing structural characterization in their native state comes from single-particle cryo-EM studies. The 3D structure of the 8 nm RNA tetrahedrons with two-helix turn per edge was first analyzed (FIG. 1F). Single-particle 3D reconstruction was applied by analyzing a total of 1254 particles collected from cryo-EM images and achieved a final resolution of 19 Å (gold standard criterion, 0.143 Fourier shell correlation) (FIGS. 21A-21C). The 3D reconstruction data revealed that the RNA tetrahedron has a clear overall shape consistent with the computational 3D model (FIG. 1C) which agrees with the predicted size of 8 nm. The 2D computed projections of the reconstructed RNA tetrahedron 3D model showed clear match to the 2D class averages of the raw particles, suggesting the reconstructed 3D model truly represented the native structure and conformation of the designed RNA tetrahedron. The images from cryo-EM accord with the global images obtained by AFM imaging (FIG. 1E). However, the central cavities of each tetrahedron were too small to be resolved by AFM and gave an apparent size of 12.5±0.6 nm. The observed size discrepancy is due to limitations in the diameter of the AFM tip. To further characterize the size of the RNA tetrahedrons, dynamic light scattering (DLS) was performed. DLS assumes that the particles have an average globular geometry in solution. The apparent hydrodynamic size of the RNA tetrahedron was determined to be 8.5±2.4 nm (FIG. 2a).

The surface charge of RNA tetrahedrons, measured as zeta potential, was also evaluated by DLS. As expected, due to the phosphate backbone of nucleotides, RNA tetrahedrons have a negative surface charge with a single peak at −14.9±1.0 mV. This negative surface charge is advantageous for the overall colloid stability of RNA nanoparticles and prevents forming aggregation in solution. Moreover, negative surface charge could also reduce the non-specific interaction of the nanoparticles with the reticuloendothelial system (RES) and minimize non-specific cell entry, which is attractive for in vivo targeted drug delivery and theranostic applications.[35]

To assess the thermodynamic stability of RNA tetrahedrons, their melting temperatures (Tm) were investigated by measuring their fluorescence intensities in the presence of SYBR Green II dye with the change of temperature on a real-time PCR machine. Melting experiments revealed that the assembled RNA tetrahedron had a very smooth, high-slope temperature dependent melting curve with a Tm of 71.3±1.8° C. The high slope indicates cooperative assembly of the tetrahedron from its four component strands. Moreover, the melting curve of RNA, 2'-F RNA and DNA tetrahedrons were compared. The results showed that 2'-F RNA tetrahedrons was the most stable with a Tm of 77.7±2.4° C., followed by RNA tetrahedron with a Tm of 71.3±1.8° C., and finally DNA tetrahedron with a much lower Tm of 58.3±0.5° C. These results were in agreement with previously reported thermodynamic stability of nucleic acids with the order of stability: 2'-F RNA>RNA>DNA.[30, 31]

Figure 22C:
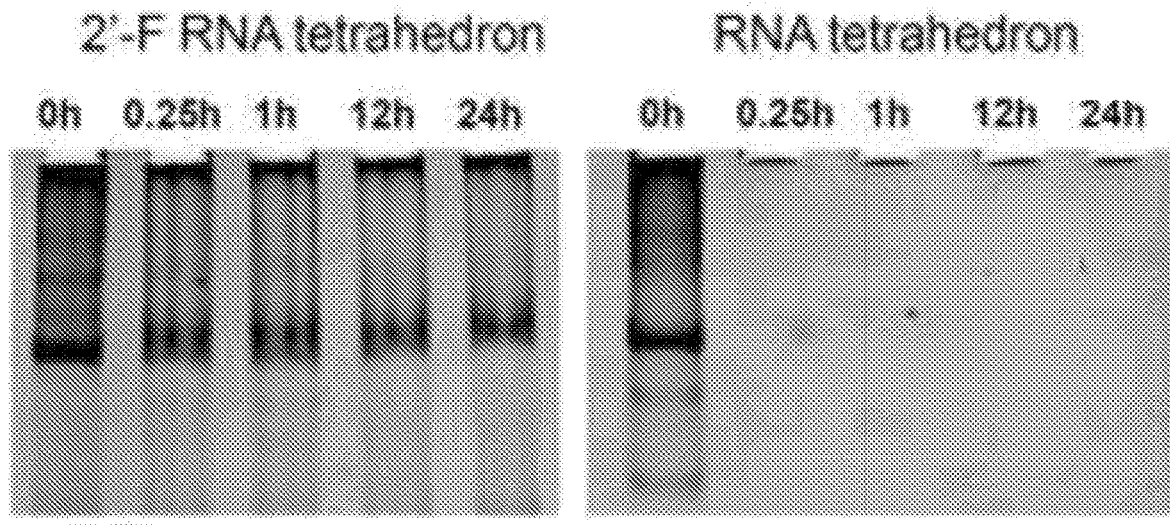
Figure 22C:
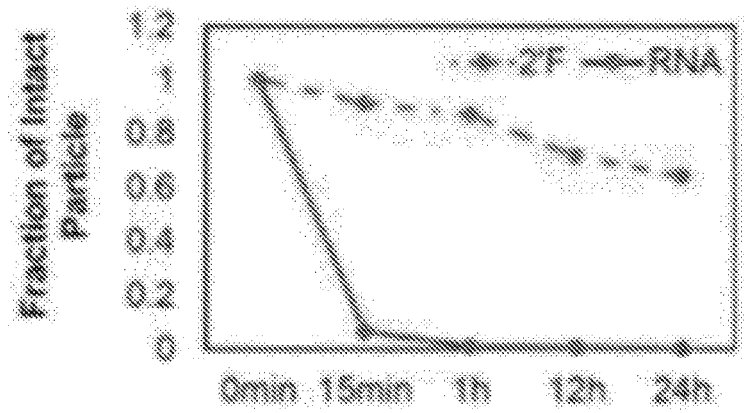

To investigate their enzymatic stability, unmodified and 2'-F modified (U and C nucleotides) RNA tetrahedrons were incubated in cell culture medium with 10% FBS (fetal bovine serum). At specific time points, aliquots were extracted and evaluated by native PAGE. Results are demonstrated in FIGS. 22A-22C. The unmodified RNA tetrahedrons were degraded within 15 min, while 2'-F counterparts were stable over an extended period of time, well beyond 24 h. The resistance to serum-mediated degradation combined with the high thermodynamic stability is particularly attractive for the in vivo application of these RNA nanoparticles.

Figure 3A:
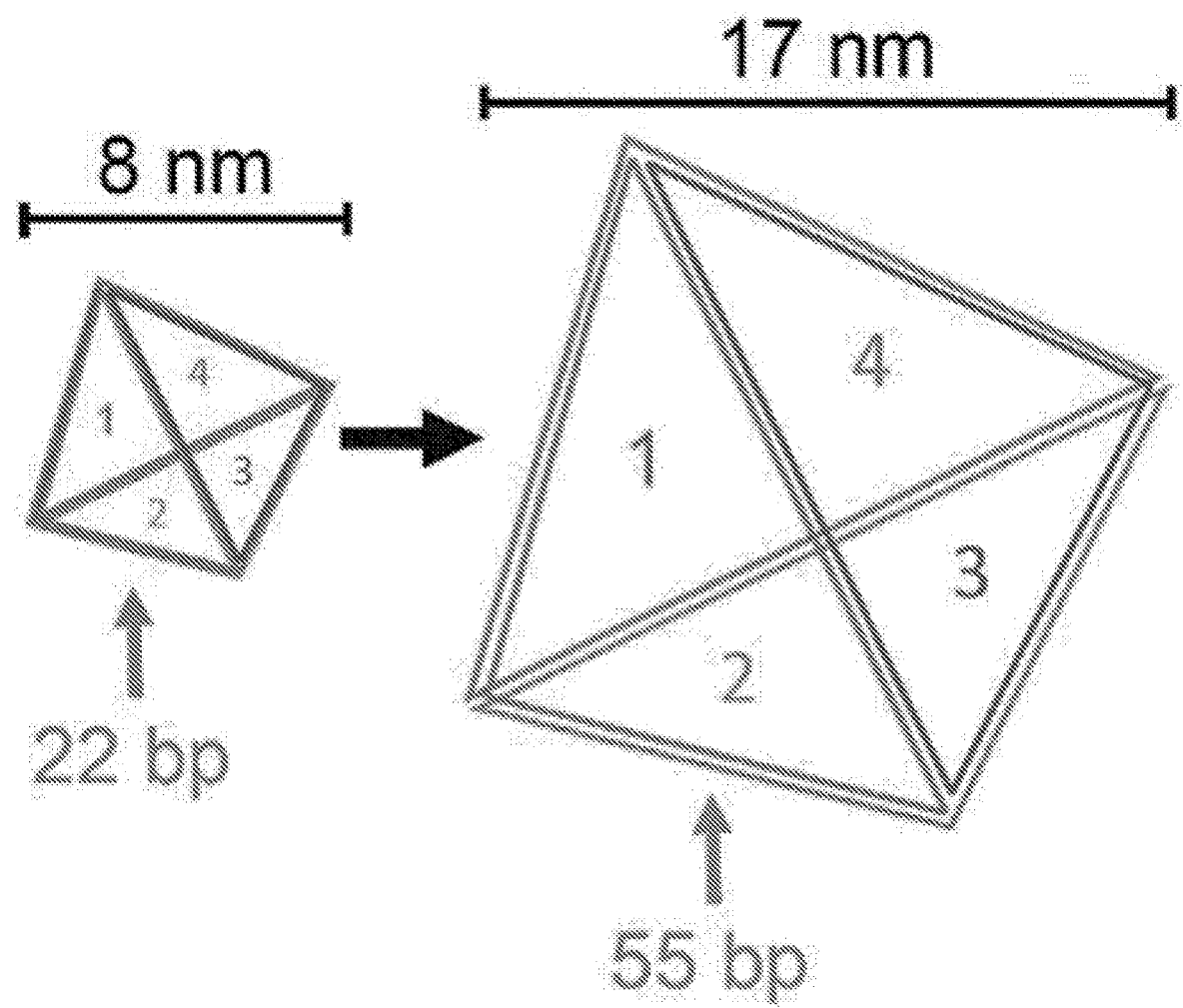
FIGS. 3A-3E demonstrate the design, assembly, and characterization of 17 nm RNA tetrahedrons.
Figure 3B:
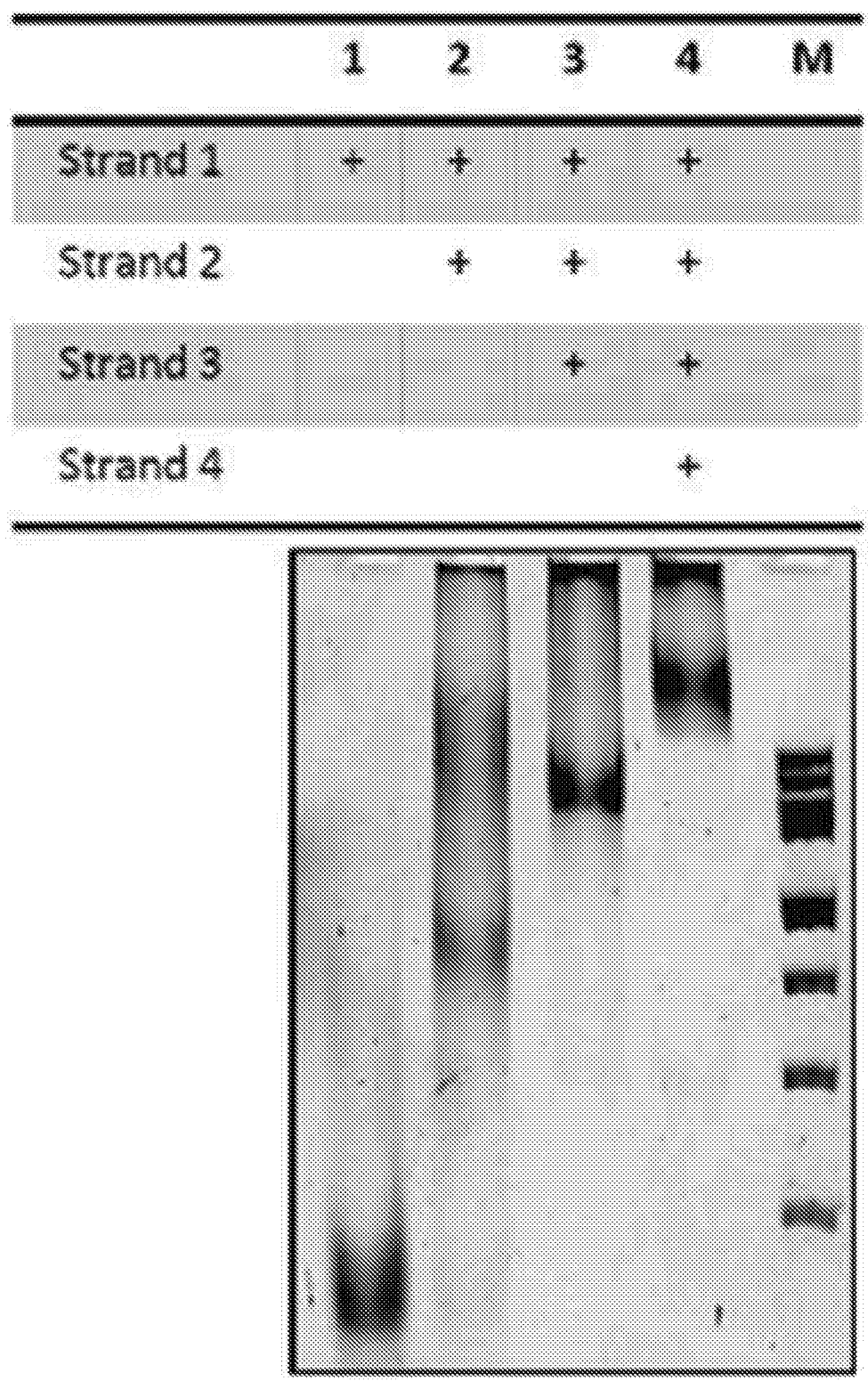
Figure 3C:
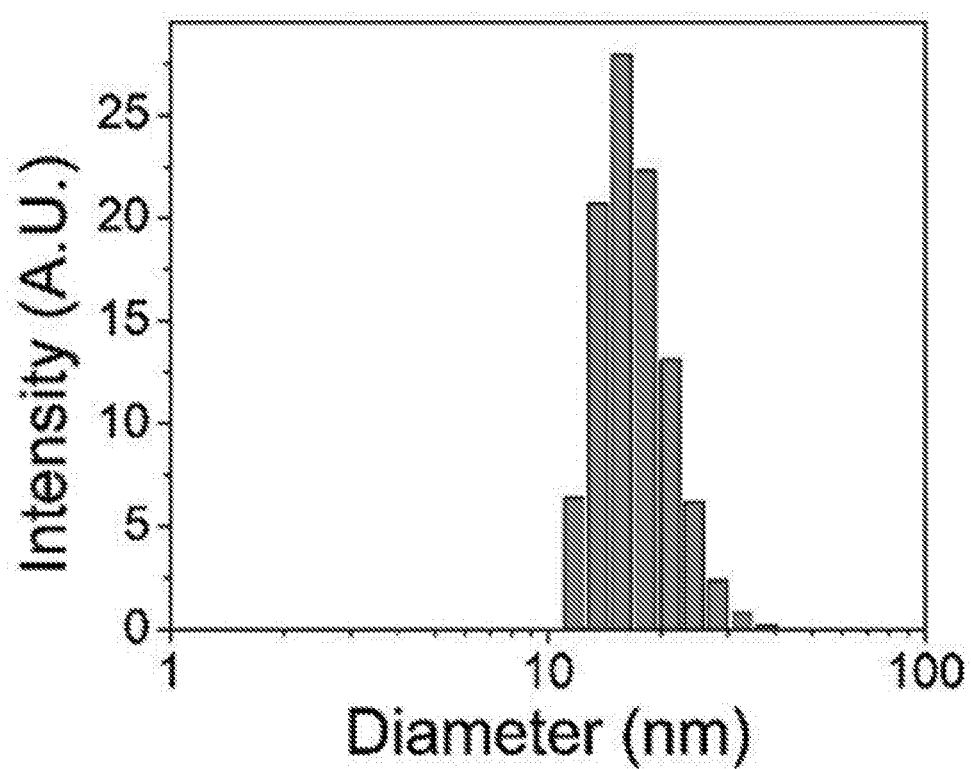
Figure 3D:
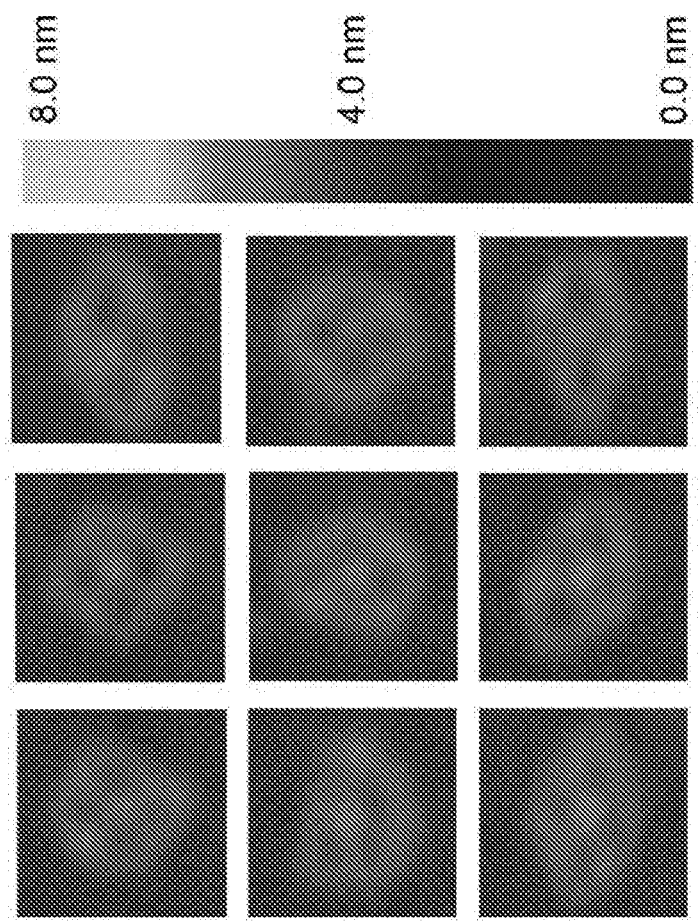
Figure 3D:
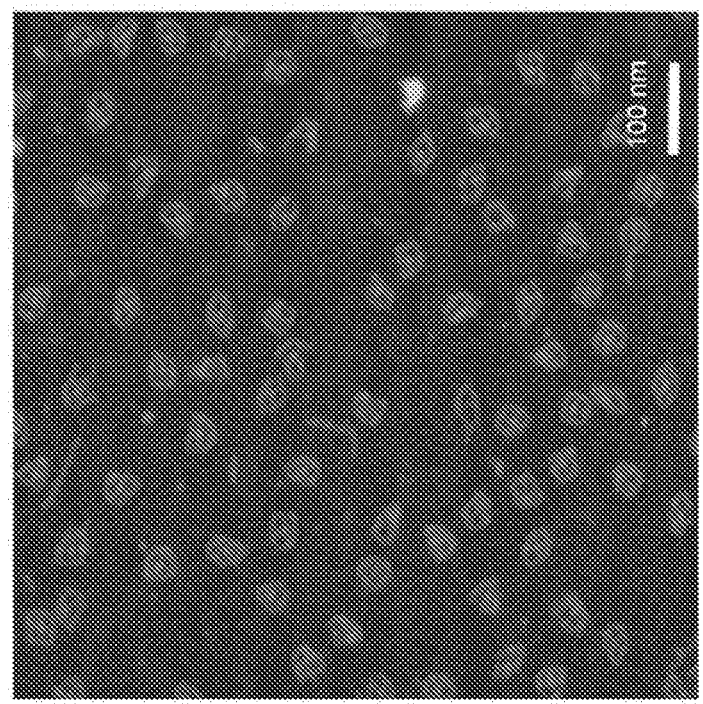
Figure 3E:
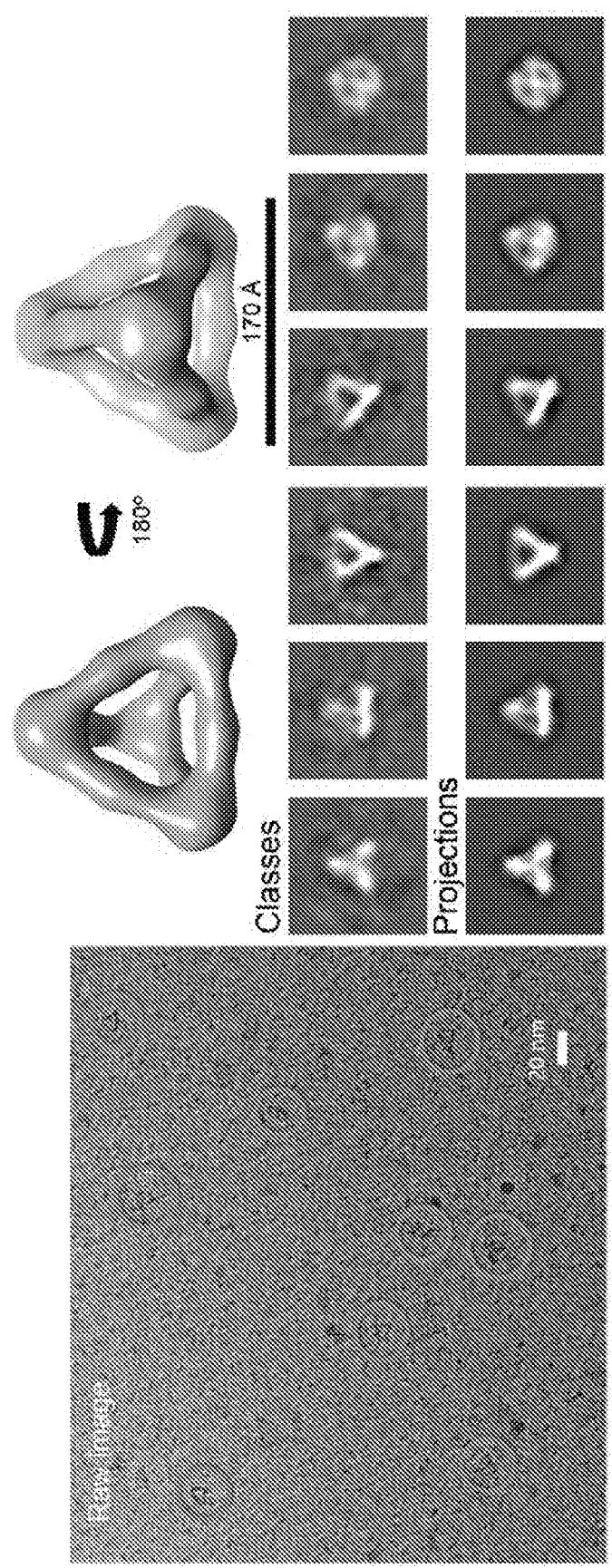
Figure 23:
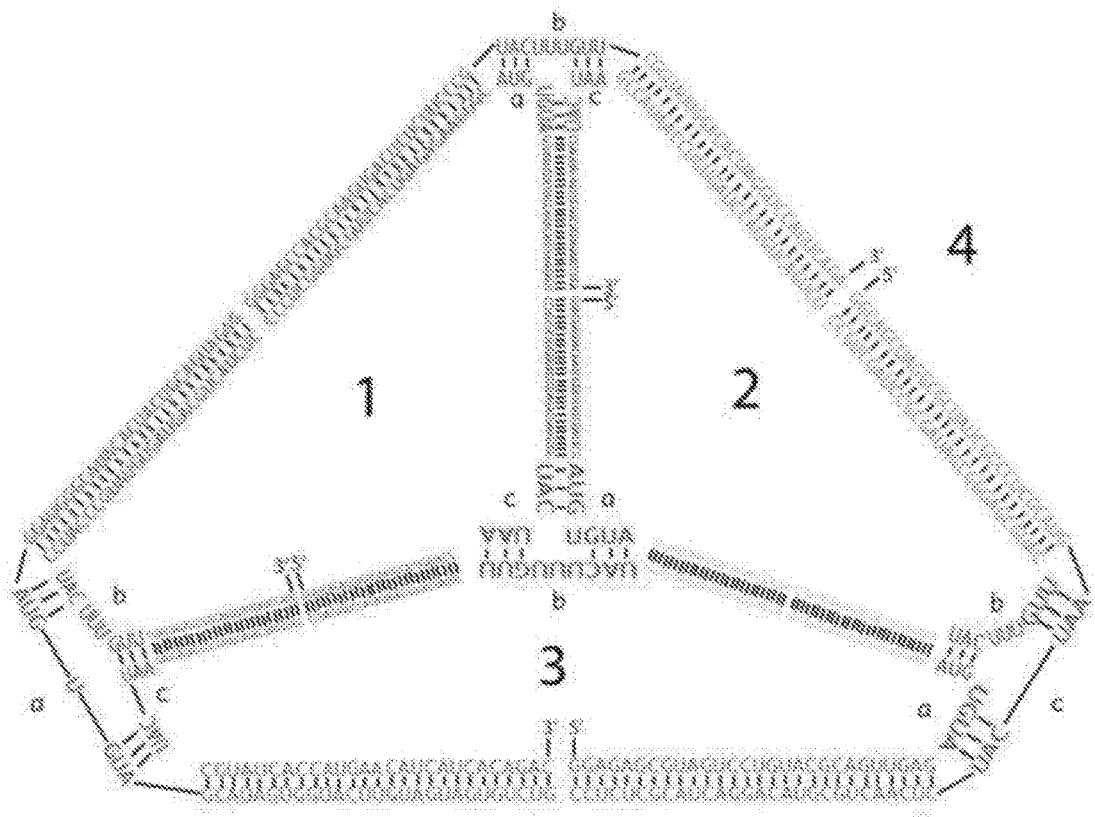
FIG. 23 shows a 2D sequence of a larger RNA tetrahedron with 55 bp per edge. Strand 1 (SEQ ID NO:11); Strand 2 (SEQ ID NO:12); Strand 3 (SEQ ID NO:13); Strand 4 (SEQ ID NO:14).
Figure 24A:
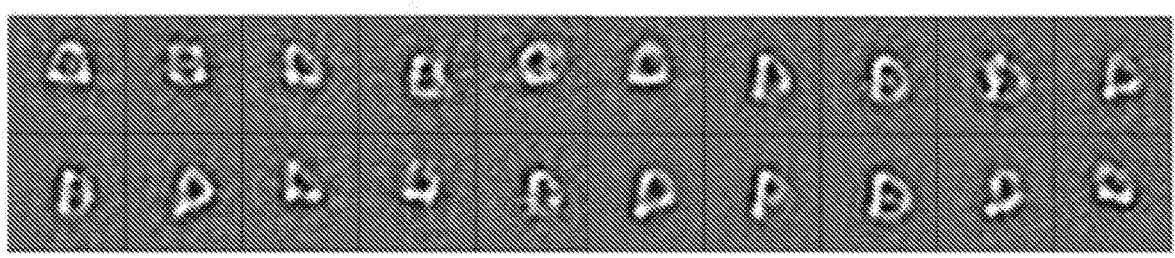
FIGS. 24A-24C show (FIG. 24A) reference free 2D class averages of the raw 17 nm tetrahedrons, (FIG. 24B) 0.143 Fourier shell correlation, and (FIG. 24C) tilt pair validation of 3D structure.
Figure 24B:
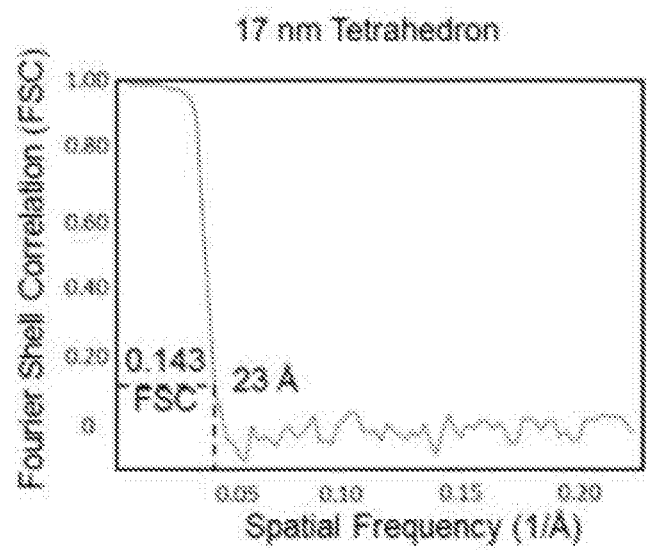
Figure 24C:
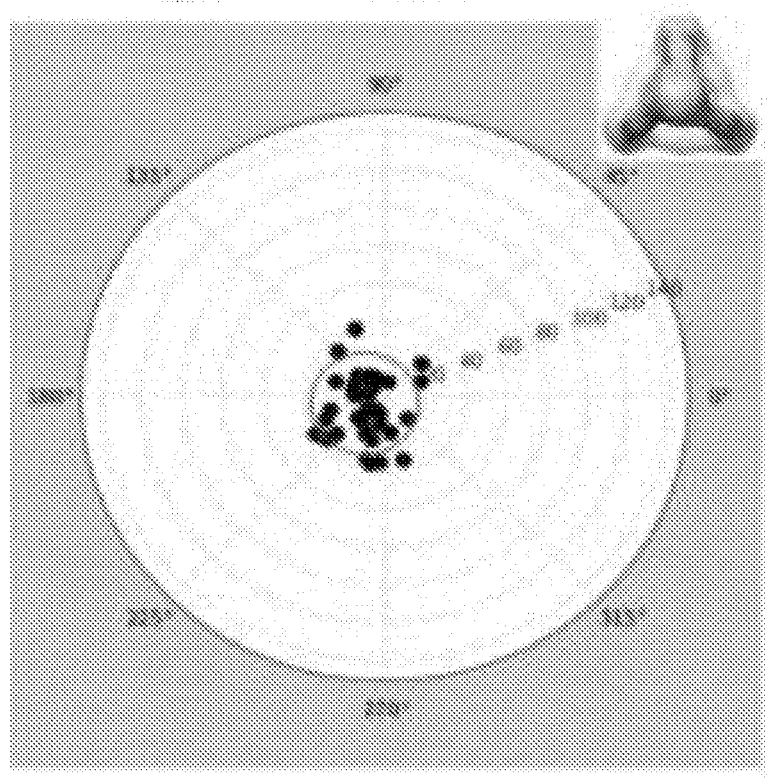

To demonstrate the precise tunable sizes of the RNA tetrahedrons, a larger 17 nm RNA tetrahedron was designed in which every edge of the tetrahedron was extended to 55 bp equal to five helix turns (FIG. 23). This larger nanoparticle has the same overall tetrahedral geometry in this design (FIG. 3A). Upon annealing the four component strands in one-pot self-assembly, the larger RNA tetrahedron assembled with high efficiency, as revealed by native PAGE analysis (FIG. 3B). DLS experiments revealed that the hydrodynamic diameter of the larger RNA tetrahedron was 16.9±1.6 nm, which is in agreement with the designed dimensions (FIG. 3C). Moreover, AFM imaging was clearly able to resolve the tetrahedral morphology along with the inner cavities (FIG. 3D). Since the RNA tetrahedrons were dried on the APS-modified mica surface before imaging in air, flattened tetrahedral shapes were observed. The RNA nanoparticles were also highly homogenous in shape and structure, demonstrating the robustness of the self-assembly of RNA tetrahedrons. Cryo-EM image further showed the very clear RNA tetrahedron nanoparticles (indicated by red circles) with the expected sizes and geometries (FIG. 3E). Single-particle 3D reconstruction of a total of 1582 particles collected from 131 cryo-EM images achieved a resolution of 23 Å (gold standard criterion, 0.143 Fourier shell correlation, FIGS. 24A-24C). FIG. 28 shows related tilt geometry computed for tilt pair of images, using the final 3D model of the 17 nm RNA Tetrahedron.

Figure 4A:
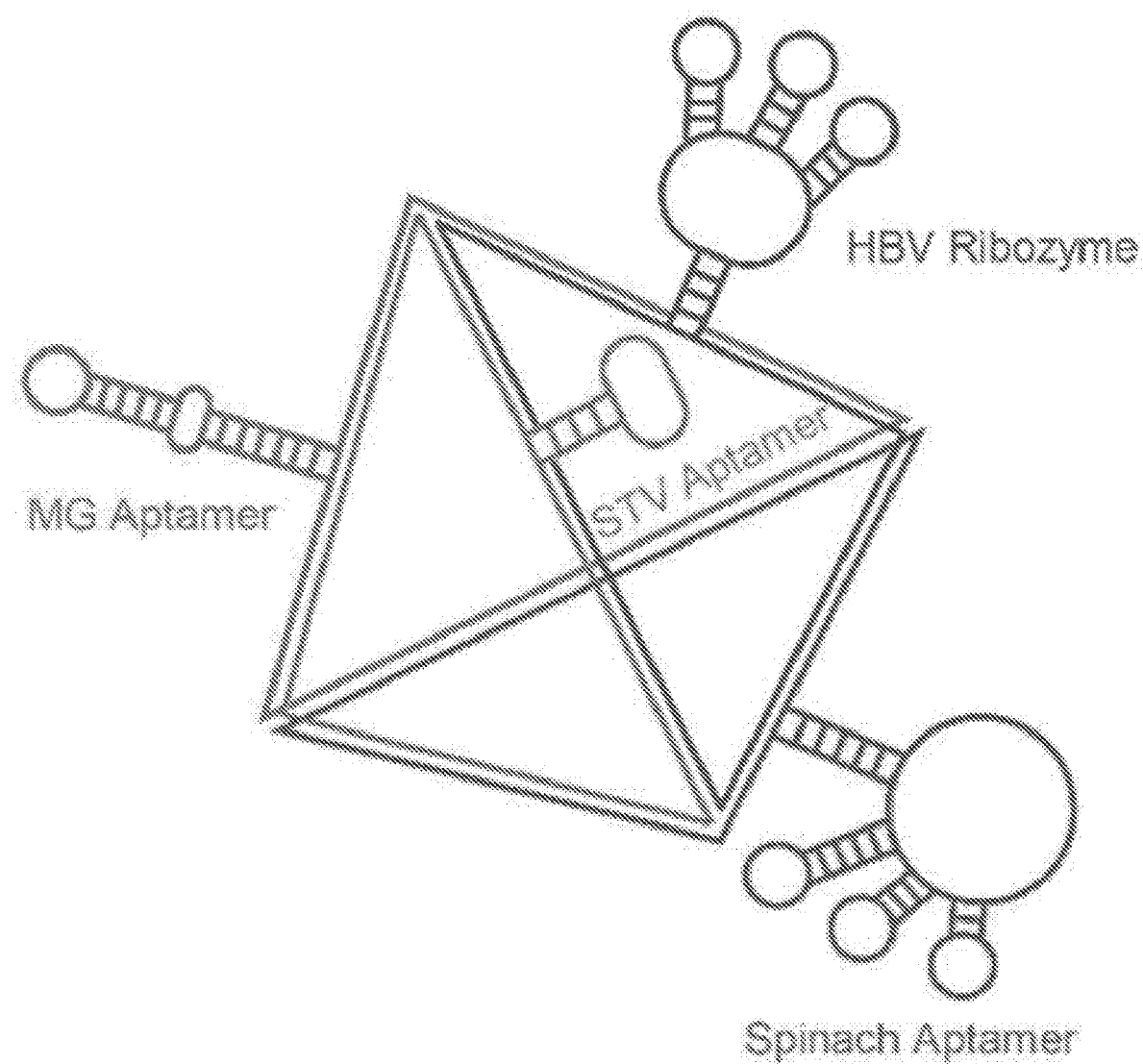
FIGS. 4A-4F demonstrates the functional characterization of multifunctional RNA tetrahedrons.
Figure 4B:
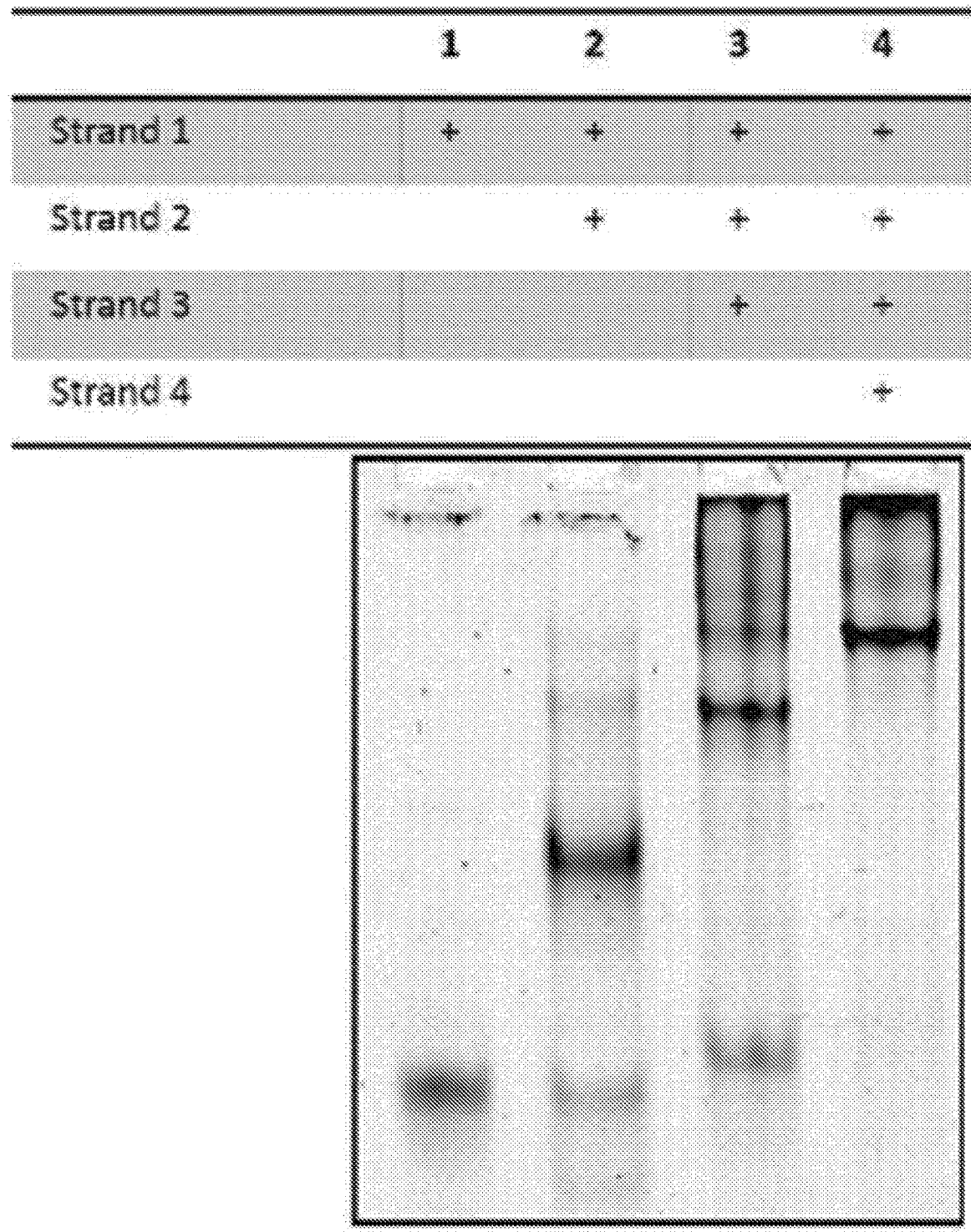

To evaluate the application of tetrahedrons, four different functional modules including a hepatitis B virus (HBV) ribozyme, fluorogenic aptamers for malachite green (MG) or Spinach, and a streptavidin-binding aptamer (FIG. 4A) were incorporated into the tetrahedron structure. The sequences of the functional modules were simply fused with the sequences of the 3WJ core, and then synthesized by in vitro transcription. After annealing the strands, the step-wise self-assembly was evaluated by native PAGE analysis to confirm the successful assembly of the RNA tetrahedrons (FIG. 4B). Functional assays were then conducted to determine whether the modules retained their authentic folding and functionalities upon incorporation into the RNA tetrahedrons.

Figure 4C:
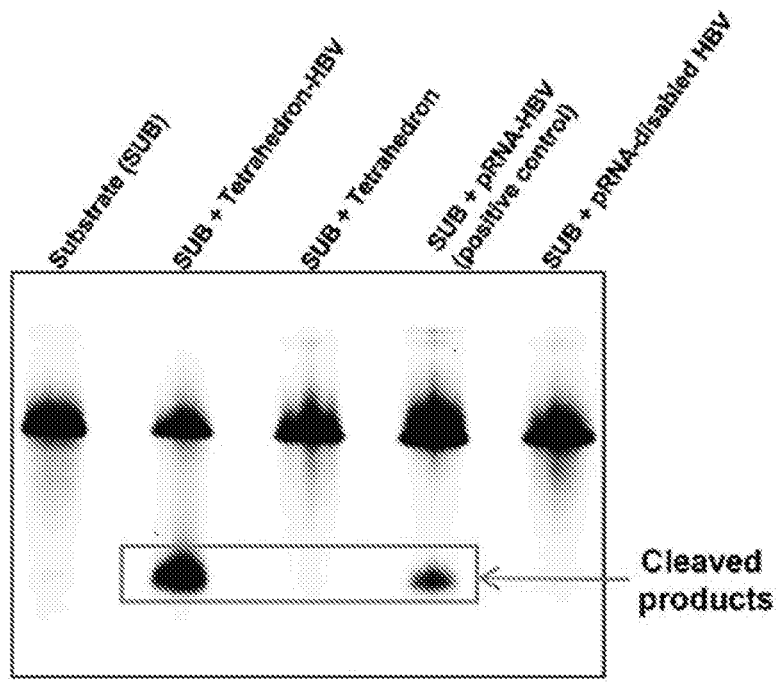

The HBV ribozyme is a hammerhead ribozyme that can target and cleavage the 135 nt HBV genomic RNA substrate. [36] The HBV ribozyme was fused to the RNA tetrahedron by extending one of the strands of the nanoparticle. After incubation with the RNA tetrahedron harboring the HBV ribozyme, the HBV substrate was cleaved into fragments with smaller molecular weights, as revealed by PAGE analysis (FIG. 4C). The yield of the cleavage reaction was comparable with the positive control (pRNA harboring HBV ribozyme). In contrast, RNA tetrahedron by itself or harboring disabled HBV ribozyme (G→A mutation in catalytic site) had no catalytic effects. The result confirmed that the designed multifunctional RNA tetrahedron successfully escorted the HBV ribozyme, and the catalytic activity was retained after ribozyme sequence was fused to the tetrahedron.

Figure 4D:
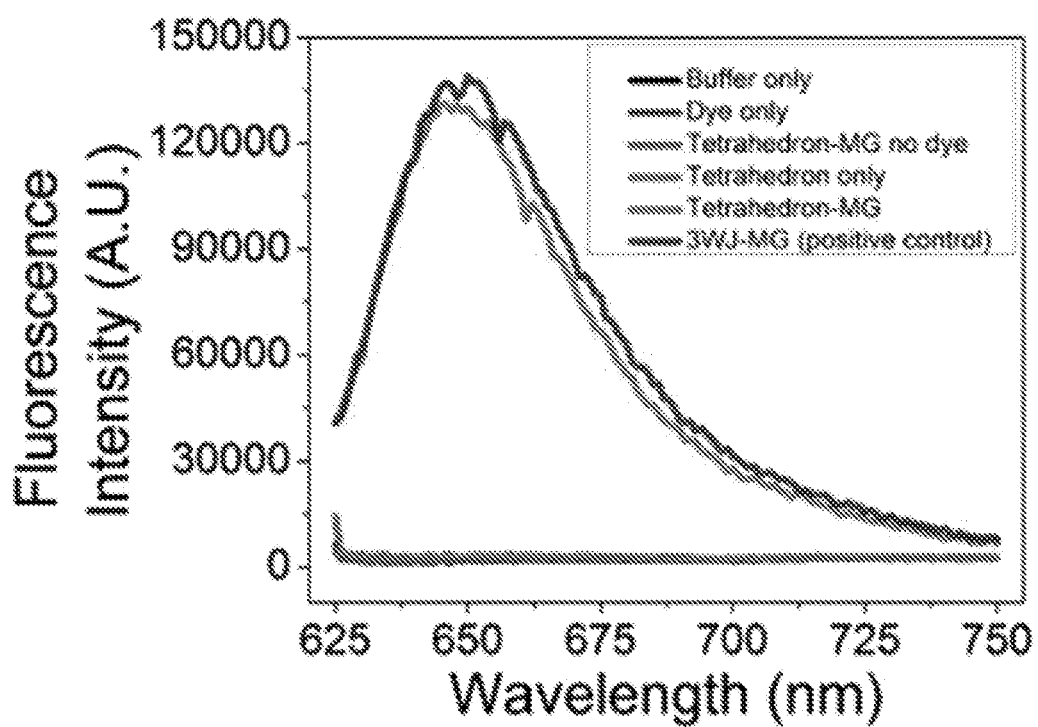
Figure 4E:
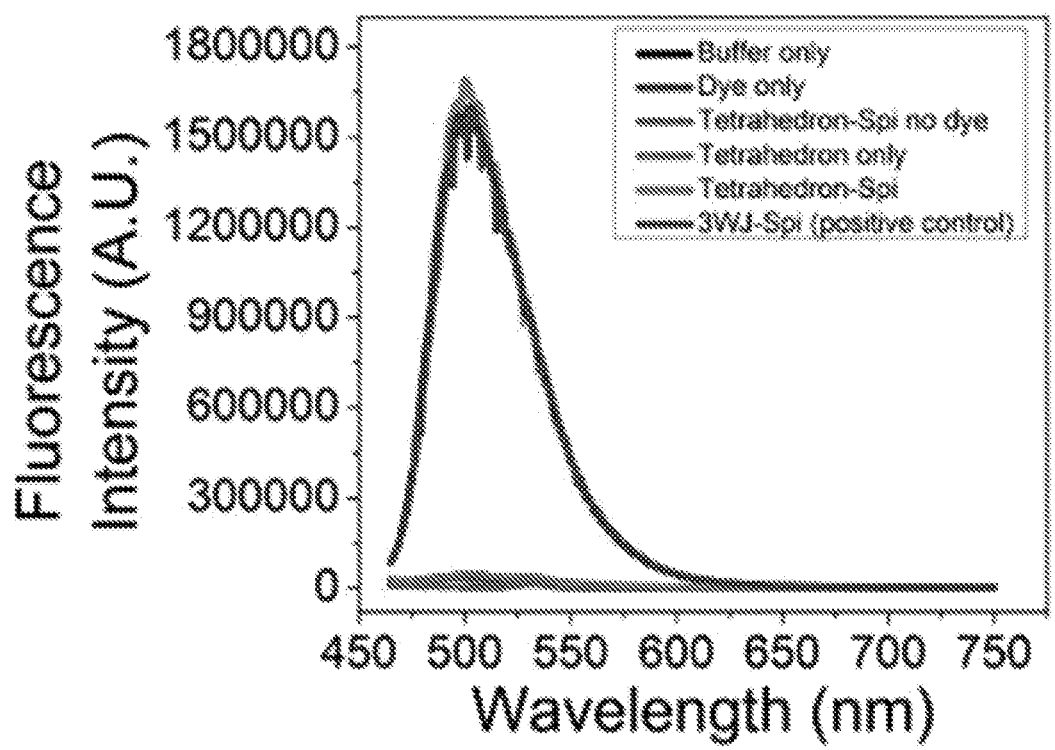

Both MG[37,38] and Spinach[39] aptamers are well-characterized for their fluorogenic properties, which emit fluorescence upon binding of their respective dye targets, triphenylmethane and 3,5-difluoro-4-hydroxybenzylidene imidazolinone (DFHBI). To verify that the MG and Spinach aptamers incorporated into the multifunctional RNA tetrahedron are still functional and folded correctly, fluorescence studies were performed using a fluorospectrophotometer. The fluorescence emission spectra showed that both the aptamers retained their ability to bind their respective dyes and emitted strong fluorescence at a similar level to the positive control, indicating the retention of the correct folding and functionalities of these fluorogenic aptamers (FIGS. 4D and 4E). The fluorogenic modules fused with tetrahedron nanoparticles can have potential applications for imaging these nanoparticles in cells.

Figure 4F:
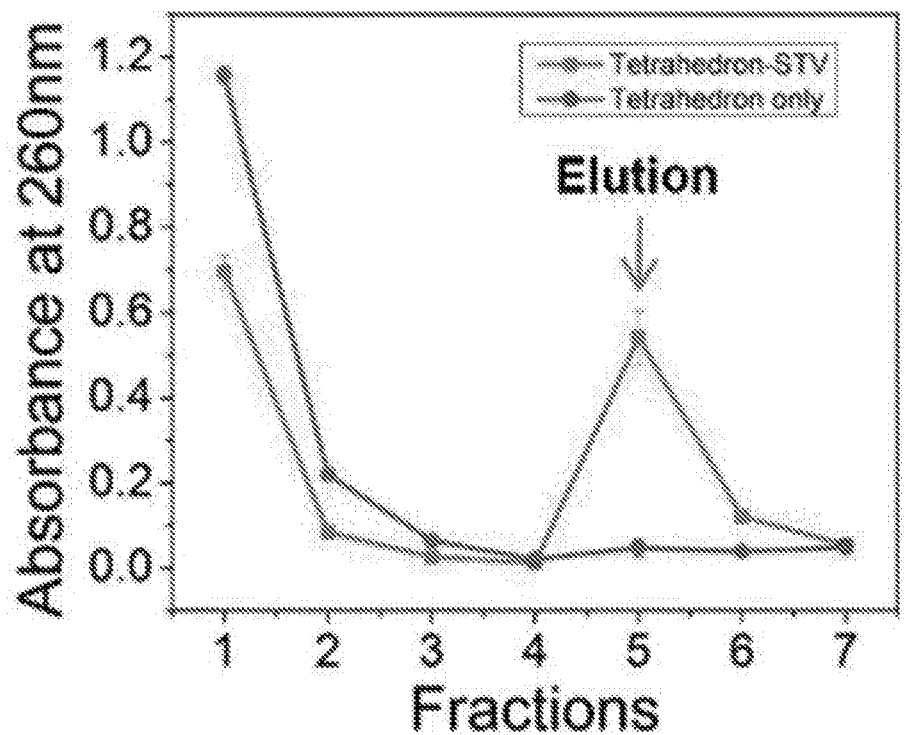
Figure 25:
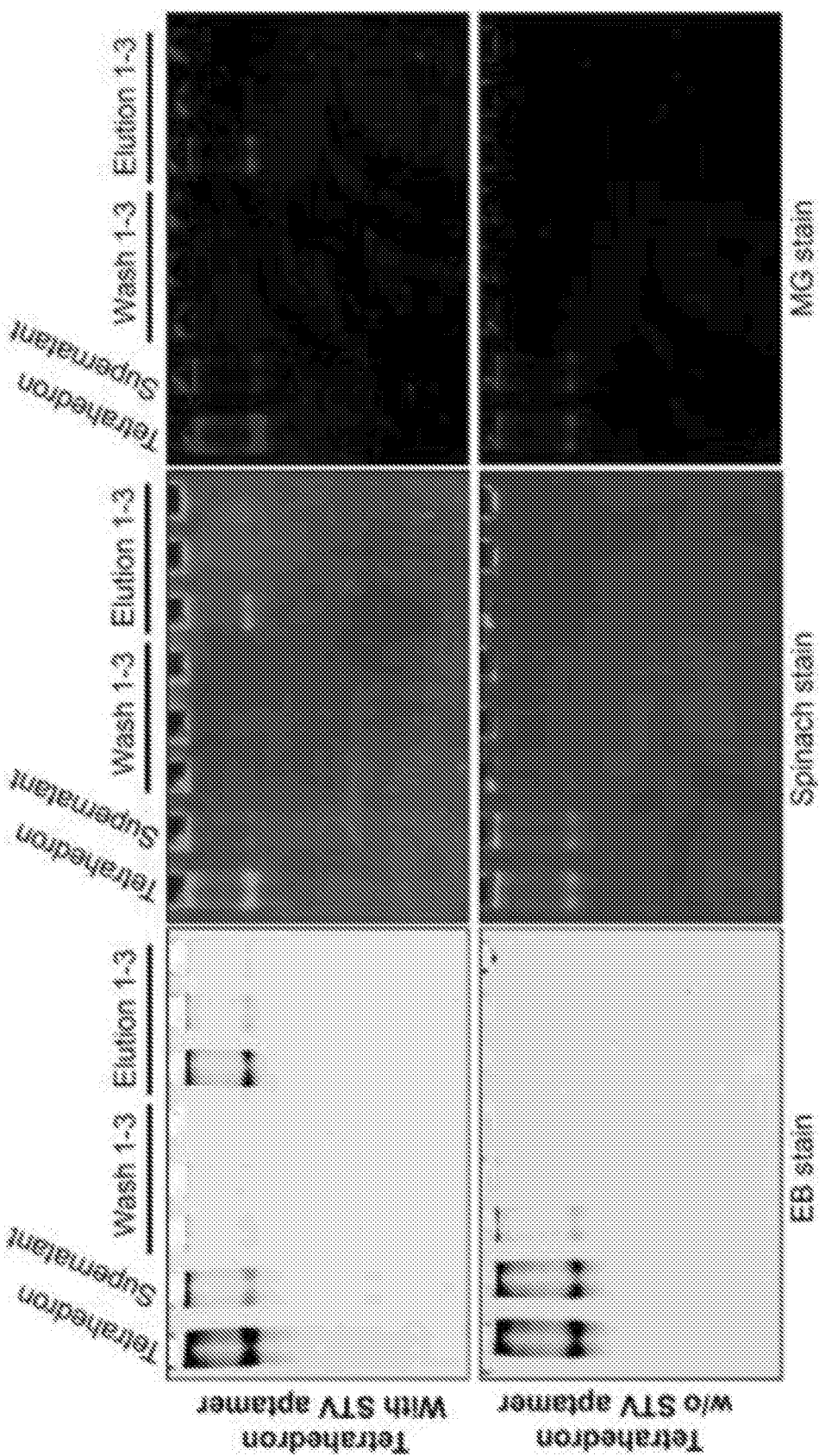
FIG. 25 shows a panel of images demonstrating the results from a 7% native PAGE assay of multifunctional RNA tetrahedrons with or without (w/o) streptavidin aptamer after binding, washing and elution from the STV column as visualized by ethidium bromide (EB) staining, Spinach aptamer fluorescence (spinach stain) and MG aptamer fluorescence (MG stain).

Upon incubation with STV agarose resins, the multifunctional RNA tetrahedrons harboring STV aptamer[40] successfully bind to the resin with high affinity and were eluted by biotin (FIG. 4F). In contrast, the negative control tetrahedron did not bind to the resin and also did not show up in the elution fractions. The results indicated that the fusion with RNA tetrahedron did not interfere with the native structure and function of the STV aptamer. Moreover, in PAGE analysis of the eluted multifunctional nanoparticles harboring MG and Spinach aptamer, they still retained their fluorogenic properties, indicating that the RNA tetrahedron structure promoted the correct folding of the two aptamers after fusion into the RNA nanoparticle (FIG. 25). The results demonstrated that the fused STV aptamer could be potentially employed as a handle to specifically purify the assembled multifunctional RNA tetrahedrons by using STV agarose resins.

Figure 5A:
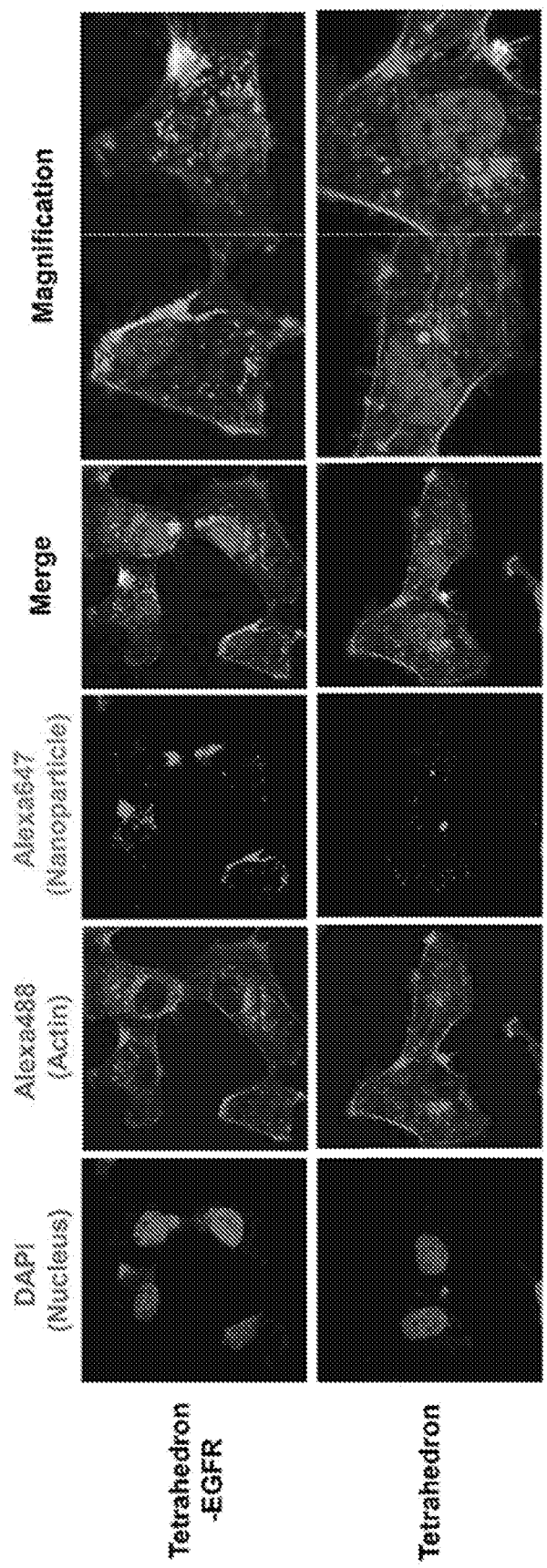
FIGS. 5A-5C demonstrate results of an in vitro and in vivo evaluation of RNA tetrahedrons harboring siRNA and cancer-targeting aptamers.
Figure 5B:
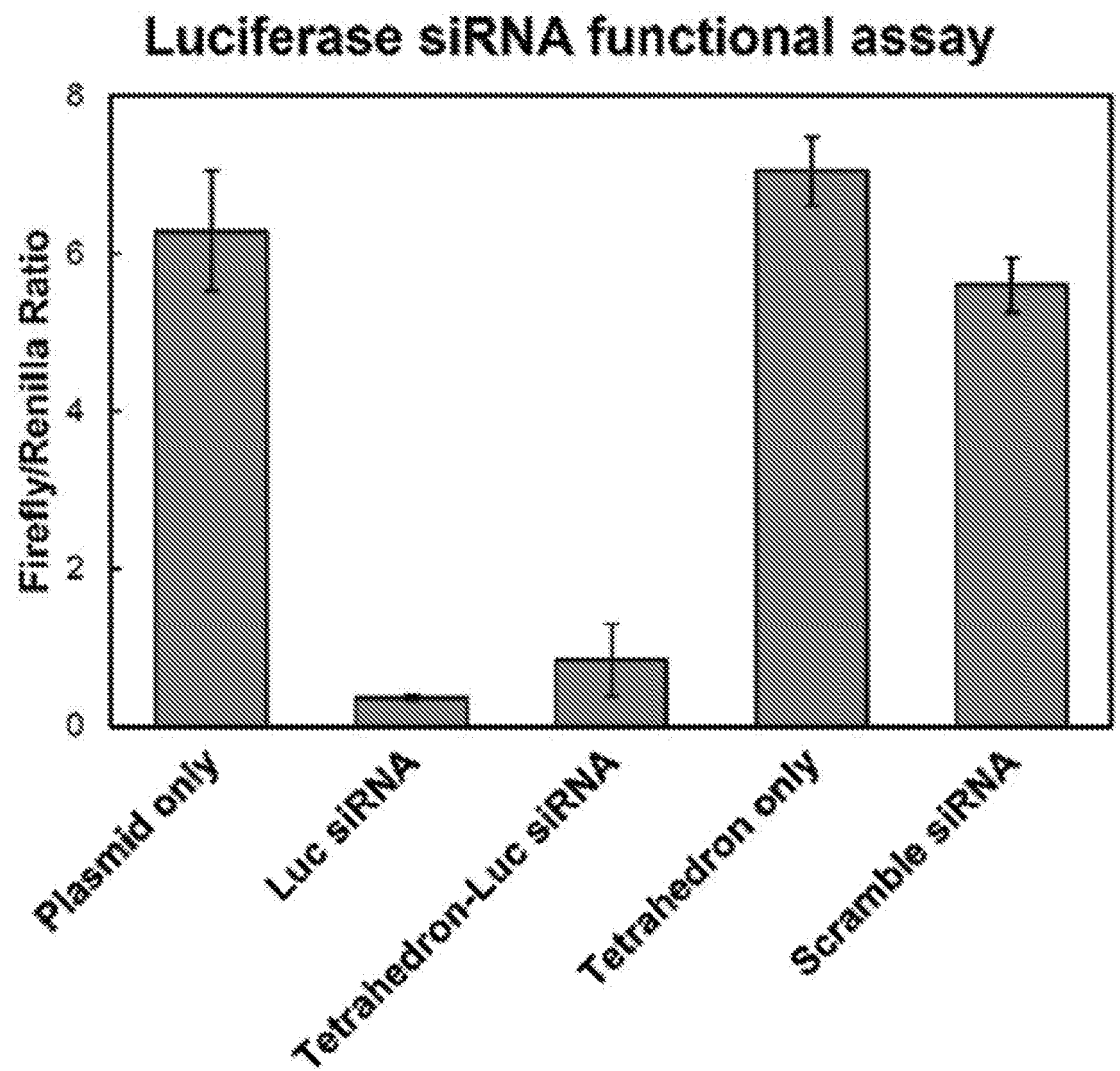
Figure 26:
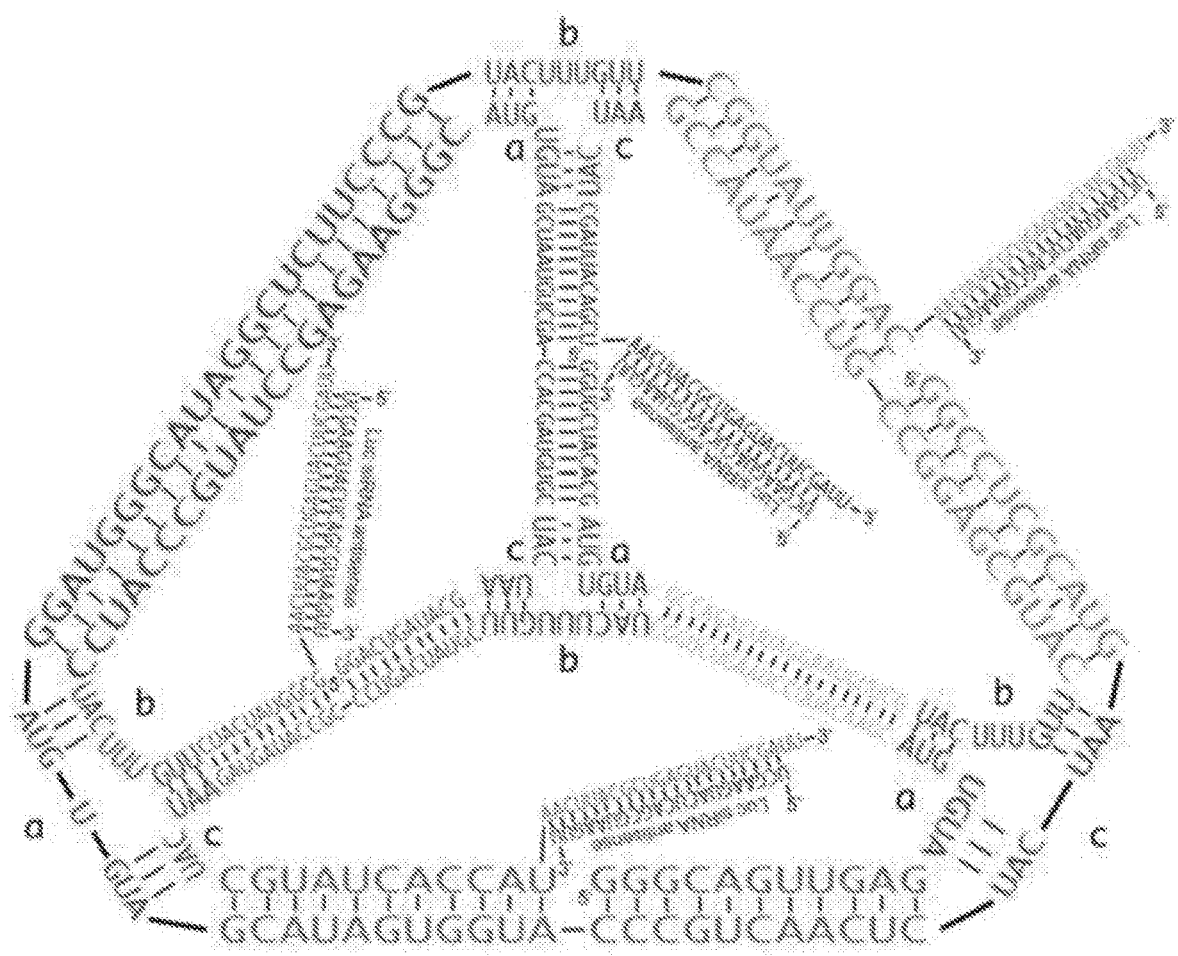
FIG. 26 shows a 2D sequence of an RNA tetrahedron harboring luciferacse siRNAs. Strand 1 (SEQ ID NO:15); Strand 2 (SEQ ID NO:16); Strand 3 (SEQ ID NO:17); Strand 4 (SEQ ID NO:18); Luc siRNA antisense (SEQ ID NO:19).

Dual-luciferase reporter assay was utilized to study the gene silencing effects of the RNA tetrahedron harboring four siRNAs targeting the same region of the firefly luciferase gene (FIG. 26). The *Renilla* luciferase, which was not the target of the luciferase siRNA, served as an internal control. The relative ratio of the expression level of the firefly luciferase to the *Renilla* luciferase was used to evaluate the targeted gene silencing effect in MCF-7 cells upon transfection. The results revealed that the tetrahedron harboring four luciferase siRNAs with $1\times10^{-9}$ m concentration achieved ≈90% gene silencing which is similar to the positive control of luciferase siRNA only at $4\times10^{-9}$ m concentration. In contrast, the tetrahedron only and scrambled control did not show any noticeable gene silencing effects (FIG. 5B). These results demonstrated that luciferase siRNA still retained their gene silencing ability after incorporation into the RNA tetrahedrons, suggesting that RNA tetrahedrons could serve as an efficient vehicle for intracellular siRNA delivery.

Figure 27:
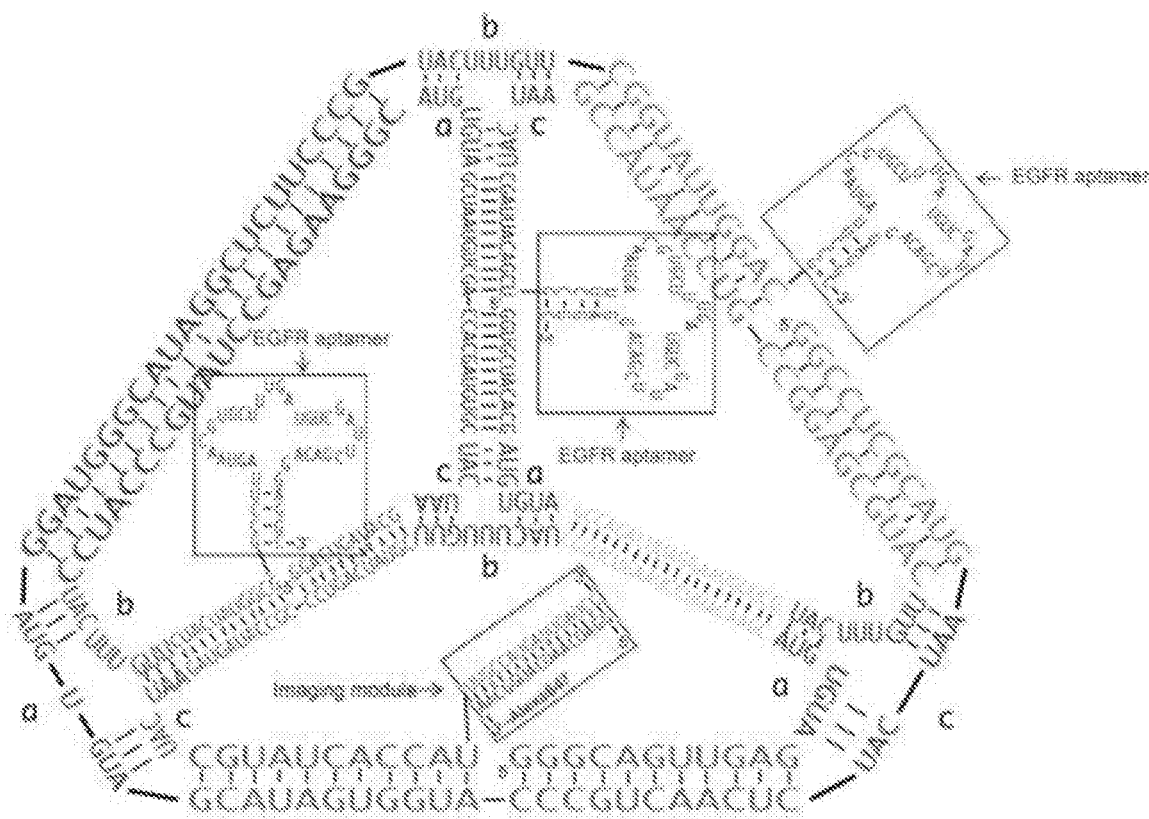
FIG. 27 shows a 2D sequence of an RNA tetrahedron harboring EGFR aptamers and Alexa647 fluorescent probe. Strand 1 (SEQ ID NO:20); Strand 2 (SEQ ID NO:21); Strand 3 (SEQ ID NO:22); Strand 4 (SEQ ID NO:23); Alexa 647 (SEQ ID NO:24).

For effective cancer therapy, it is ideal to guide therapeutics to specific cancer cells. The epidermal growth factor receptor (EGFR) family of receptor tyrosine kinases (RTK) is highly prevalent in both primary tumors and metastatic breast cancer cells, making them an ideal candidate for targeted therapies.[41] RNA aptamers have been developed to bind to EGFR receptors[42-45] with high selectivity and sensitivity. Here EGFR targeting RNA aptamers were incorporated into RNA tetrahedrons (FIG. 27) and their cellular binding evaluated by confocal microscopy (FIG. 5a). Alexa647 labeled RNA strand was incorporated into tetrahedrons for fluorescence imaging. Tetrahedrons without EGFR aptamer were used as negative control. Confocal imaging showed that tetrahedron nanoparticles with EGFR aptamers strongly bound to EGFR(+) MDA-MB-231 cells (FIG. 5a), as revealed by the co-localization of the Alexa647-labeled RNA and cellular actin (FIG. 5a). In contrast, negative control "naked" tetrahedrons without the EFGR aptamer showed negligible cellular binding. The results suggest that the EFGR aptamer could facilitate the binding of RNA tetrahedrons to EGFR-expressing cancer cells.

Figure 5C:
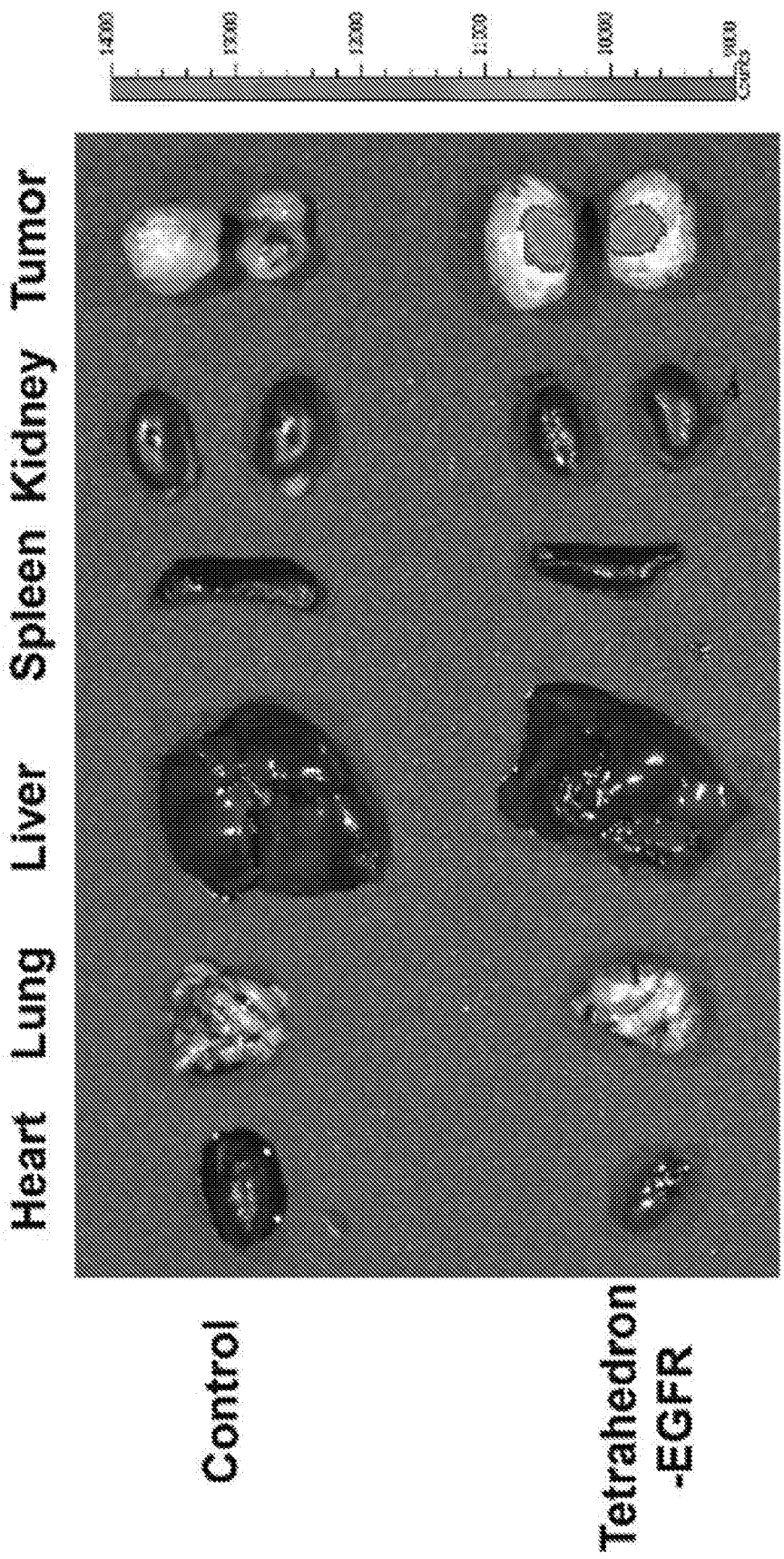
Figure 5D:
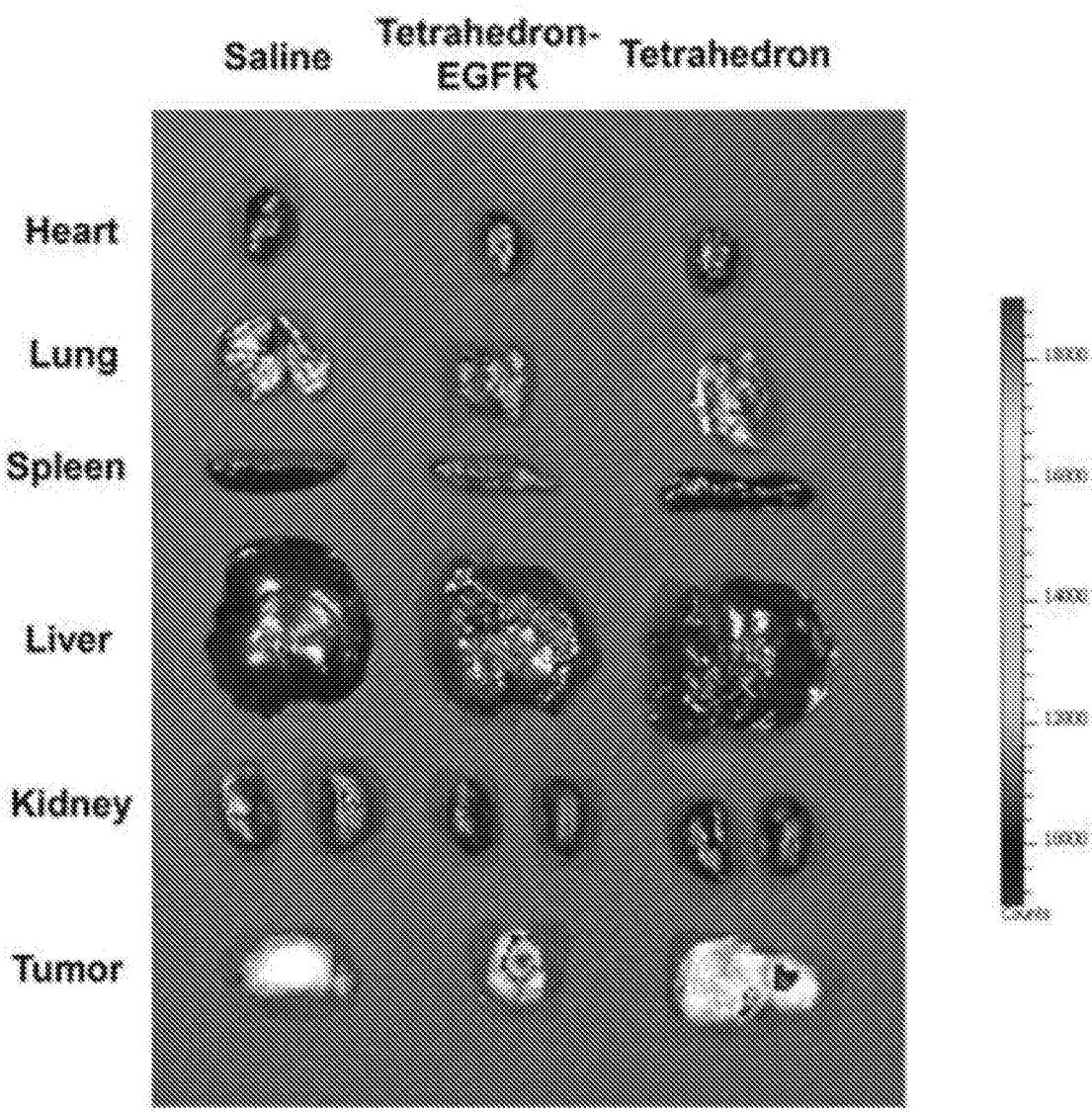
FIG. 5D shows the results of a biodistribution assay of tetrahedron nanoparticles with EGFR aptamer in a KB xenograft mouse model. PBS saline and tetrahedron without the EGFR aptamer treated mice were used as a control.

For studying the in vivo cancer-targeting properties of the RNA tetrahedrons, breast cancer mouse models were generated orthotopic by injecting MDA-MB-231 cells directly into the mammary fat pad of athymic nude mice[46] to generate xenografts. Nuclease-resistant 2'-F RNA tetrahedrons harboring EGFR aptamers and Alexa647 were systemically injected into mice and their biodistribution was monitored by whole-body imaging. The mice were sacrificed 8 h post injection and their organs were collected for ex vivo imaging (FIG. 5C). RNA tetrahedrons were not detected in any other organs except the breast tumor, indicating that the nanoparticles were cleared from normal organs quickly and did not accumulate in the liver, lung, spleen, or kidney after systemic injection. In another confirmatory animal trial by using an EGFR-expressing KB cells xenograft mouse model, similar cancer-targeting ability of the RNA tetrahedrons was also observed (FIG. 5D). The selective cancer-targeting ability of the RNA tetrahedrons would make this delivery system an attractive candidate for future targeted cancer imaging studies and/or cancer therapy.

In conclusion, the design and self-assembly of multifunctional 3D RNA tetrahedrons is disclosed based on the ultrastable pRNA-3WJ motif. The constructed RNA tetrahedrons have defined 3D structures as revealed by both AFM and single particle cryo-EM. The size of the RNA tetrahedrons can be easily tuned by changing the number of RNA base pairs per edge. Melting experiments revealed its high thermodynamic stability. Aptamers, ribozyme, and siRNA were successfully incorporated into the RNA tetrahedron with their correct folding and optimal functionality. Cellular binding and biodistribution study showed that the RNA tetrahedron functionalized with EGFR-aptamer targeted orthotopic breast tumors without detectable accumulation in other healthy organs. These results suggest that 3D RNA tetrahedron nanoparticles have the potential to escort imaging modules and therapeutics for in vivo cancer diagnosis and therapy.

REFERENCES

[1] P. Guo, Nat. Nanotechnol. 2010, 5, 833.
[2] H. Li, T. Lee, T. Dziubla, F. Pi, S. Guo, J. Xu, C. Li, F. Hague, X. Liang, P. Guo, Nano Today 2015, 10, 631.
[3] Y. Shu, F. Pi, A. Sharma, M. Rajabi, F. Hague, D. Shu, M. Leggas, B. M. Evers, P. Guo, Adv. Drug Delivery Rev. 2014, 66C, 74.
[4] N. C. Seeman, Annu. Rev. Biochem. 2010, 79, 65.
[5] F. Zhang, J. Nangreave, Y. Liu, H. Yan, J. Am. Chem. Soc. 2014, 136, 11198.
[6] M. R. Jones, N. C. Seeman, C. A. Mirkin, Science 2015, 347, 1260901.
[7] E. F. Khisamutdinov, D. L. Jasinski, P. Guo, ACS Nano 2014, 8, 4771.
[8] D. Jasinski, E. F. Khisamutdinov, Y. L. Lyubchenko, P. Guo, ACS Nano 2014, 8, 7620.
[9] I. Severcan, C. Geary, E. Verzemnieks, A. Chworos, L. Jaeger, Nano Lett. 2009, 9, 1270.
[10] S. M. Dibrov, J. McLean, J. Parsons, T. Hermann, Proc. Natl. Acad. Sci. USA 2011, 108, 6405.
[11] D. Shu, W. D. Moll, Z. Deng, C. Mao, P. Guo, Nano Lett. 2004, 4, 1717.
[12] L. Nasalean, S. Baudrey, N. B. Leontis, L. Jaeger, Nucl. Acids Res. 2006, 34, 1381.
[13] A. Chworos, I. Severcan, A. Y. Koyfman, P. Weinkam, E. Oroudjev, H. G. Hansma, L. Jaeger, Science 2004, 306, 2068.
[14] P. Guo, C. Zhang, C. Chen, M. Trottier, K. Garver, Mol. Cell. 1998, 2, 149.
[15] H. Zhang, J. A. Endrizzi, Y. Shu, F. Hague, C. Sauter, L. S. Shlyakhtenko, Y. Lyubchenko, P. Guo, Y. I. Chi, RNA 2013, 19, 1226.
[16] W. W. Grabow, P. Zakrevsky, K. A. Afonin, A. Chworos, B. A. Shapiro, L. Jaeger, Nano Lett. 2011, 11, 878.
[17] C. Hao, X. Li, C. Tian, W. Jiang, G. Wang, C. Mao, Nat. Commun. 2014, 5, 3890.
[18] I. Severcan, C. Geary, A. Chworos, N. Voss, E. Jacovetty, L. Jaeger, Nat. Chem. 2010, 2, 772.
[19] K. A. Afonin, M. Viard, A. Y. Koyfman, A. N. Martins, W. K. Kasprzak, M. Panigaj, R. Desai, A. Santhanam, W. W. Grabow, L. Jaeger, E. Heldman, J. Reiser, W. Chiu, E. O. Freed, B. A. Shapiro, Nano Lett. 2014, 14, 5662.
[20] P. Guo, S. Erickson, D. Anderson, Science 1987, 236, 690.
[21] Y. Shu, F. Hague, D. Shu, W. Li, Z. Zhu, M. Kotb, Y. Lyubchenko, P. Guo, R N A 2013, 19, 766.
[22] Y. Shu, D. Shu, F. Hague, P. Guo, Nat Protoc. 2013, 8, 1635.
[23] D. Shu, Y. Shu, F. Hague, S. Abdelmawla, P. Guo, Nat. Nanotechnol. 2011, 6, 658.
[24] F. Hague, D. Shu, Y. Shu, L. Shlyakhtenko, P. Rychahou, M. Evers, P. Guo, Nano Today 2012, 7, 245.
[25] E. F. Khisamutdinov, H. Li, D. Jasinski, J. Chen, J. Fu, P. Guo, Nucl. Acids Res. 2014, 42, 9996.
[26] Z. Li, B. Wei, J. Nangreave, C. X. Lin, Y. Liu, Y. L. Mi, H. Yan, J. Am. Chem. Soc. 2009, 131, 13093.
[27] J. P. Sadowski, C. R. Calvert, D. Y. Zhang, N. A. Pierce, P. Yin, ACS Nano 2014, 8, 3251.
[28] H. Lee, A. K. Lytton-Jean, Y. Chen, K. T. Love, A. I. Park, E. D. Karagiannis, A. Sehgal, W. Querbes, C. S. Zurenko, M. Jayaraman, C. G. Peng, K. Charisse, A. Borodovsky, M. Manoharan, J. S. Donahoe, J. Truelove, M. Nahrendorf, R. Langer, D. G. Anderson, Nat. Nanotechnol. 2012, 7, 389.
[29] R. Iinuma, Y. G. Ke, R. Jungmann, T. Schlichthaerle, J. B. Woehrstein, P. Yin, Science 2014, 344, 65.
[30] D. W. Binzel, E. F. Khisamutdinov, P. Guo, Biochemistry 2014, 53, 2221.
[31] N. Sugimoto, S. Nakano, M. Katoh, A. Matsumura, H. Nakamuta, T. Ohmichi, M. Yoneyama, M. Sasaki, Biochemistry 1995, 34, 11211.
[32] N. B. Leontis, E. Westhof, Curr. Opin. Struct. Biol. 2003, 13, 300.
[33] R. F. Garmann, A. Gopal, S. S. Athavale, C. M. Knobler, W. M. Gelbart, S. C. Harvey, RNA 2015, 21, 877.
[34] E. F. Pettersen, T. D. Goddard, C. C. Huang, G. S. Couch, D. M. Greenblatt, E. C. Meng, T. E. Ferrin, J. Comput. Chem. 2004, 25, 1605.
[35] Advanced Drug Delivery Reviews: Cancer Nanotechnology, (Eds: P. Grodzinski, V. Torchilin), Elsevier, Amsterdam, The Netherlands 2014.
[36] S. Hoeprich, Q. Zhou, S. Guo, G. Qi, Y. Wang, P. Guo, Gene Ther. 2003, 10, 1258.
[37] C. Baugh, D. Grate, C. Wilson, J. Mol. Biol. 2000, 301, 117.
[38] J. Flinders, S. C. Defina, D. M. Brackett, C. Baugh, C. Wilson, T. Dieckmann, ChemBioChem 2004, 5, 62.
[39] J. S. Paige, T. Nguyen-Duc, W. Song, S. R. Jaffrey, Science 2012, 335, 1194.
[40] C. Srisawat, D. R. Engelke, RNA 2001, 7, 632.
[41] N. E. Hynes, H. A. Lane, Nat. Rev. Cancer 2005, 5, 341.
[42] C. L. Esposito, D. Passaro, I. Longobardo, G. Condorelli, P. Marotta, A. Affuso, V. de Franciscis, L. Cerchia, PLoS One 2011, 6, e24071.
[43] K. W. Thiel, L. I. Hernandez, J. P. Dassie, W. H. Thiel, X. Liu, K. R. Stockdale, A. M. Rothman, F. J. Hernandez, J. O. McNamara, P. H. Giangrande, Nucleic Acids Res. 2012, 40, 6319.
[44] M. Y. Kim, S. Jeong, Nucleic Acid Ther. 2011, 21, 173.
[45] C. H. Chen, G. A. Chernis, V. Q. Hoang, R. Landgraf, Proc. Natl. Acad. Sci. USA 2003, 100, 9226.
[46] D. Shu, H. Li, Y. Shu, G. Xiong, W. E. Carson, F. Hague, R. Xu, P. Guo, ACS Nano 2015, 9, 9731.

Example 2: Fabrication of RNA 3D Nanoprism for Loading and Protection of Small RNAs and Model Drugs Results and Discussion Computer-Aided Rational Design and Fabrication of 3D RNA Nanoprism from Planar pRNA 3WJ Geometry.

Figure 6A:
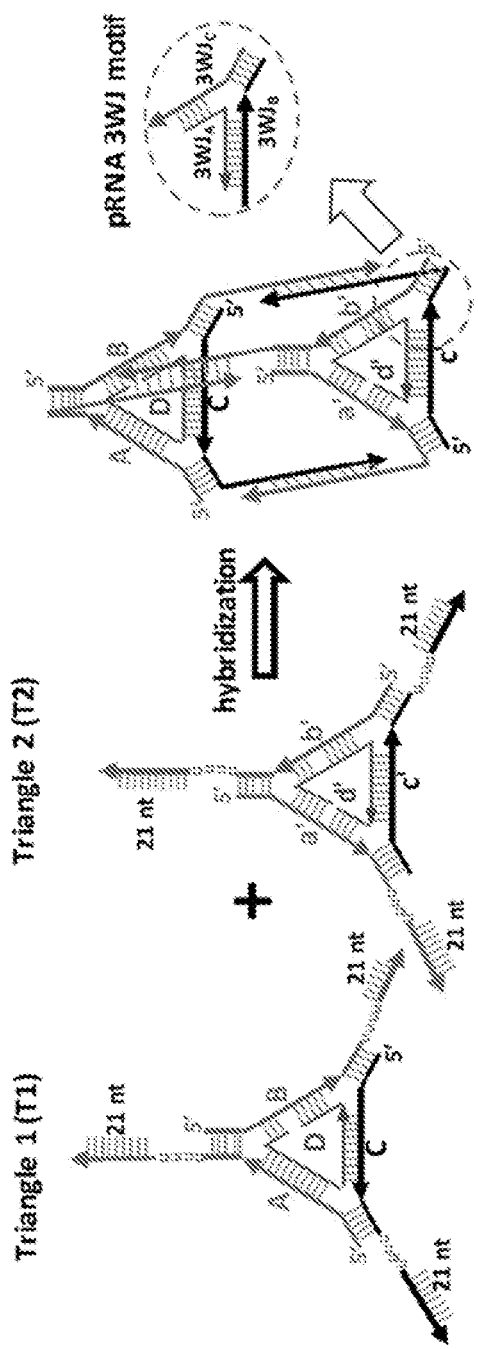
FIGS. 6A-6B demonstrate triangular Nanoprism design and 3D model structure.
Figure 6B:
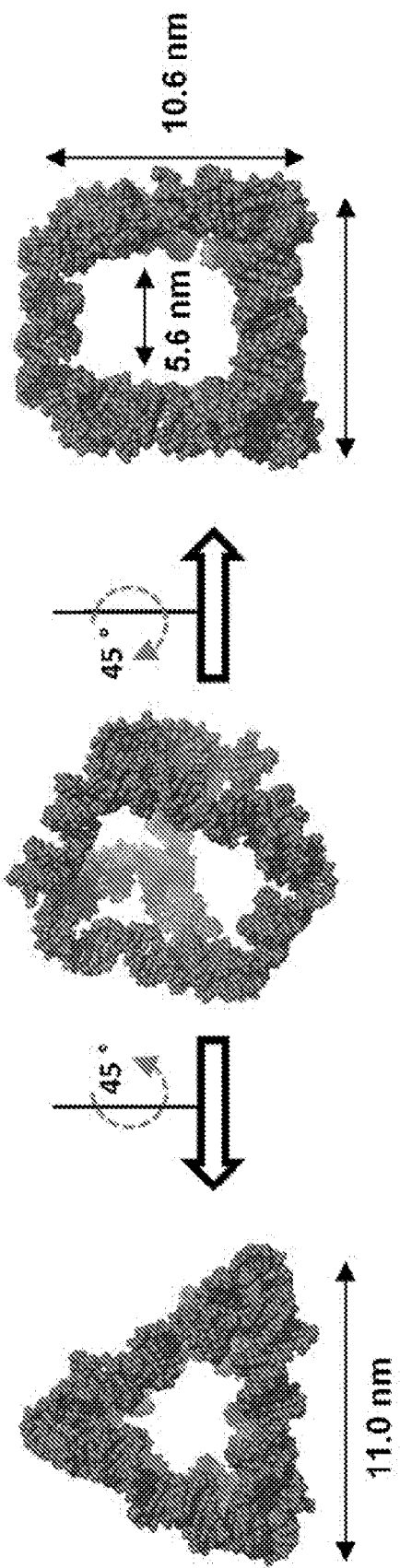

The triangular nanoprism was designed employing the structural information of pRNA 3WJ following a bottom-up approach[1]. As such, two helices of three adjacently arranged 3WJs were connected with duplex RNA to form flat triangular nanoparticles, a nanoparticle construction method devised previously[12]. To extend 2D triangle particles into a 3D RNA complex, two triangular nanoparticles (T1 and T2) containing 21 nucleotide (nt) single stranded (ss) complementary linker (L) regions on each vertex were tethered (FIG. 6A). Each ssL region was designed to interact specifically with its compliment strands L1-L1', L2-L2', L3-L3' forming RNA-RNA duplex of 21 bp. To provide structural flexibility and allow the linkers to bend to a 90° angle necessary for triangular prism complex, poly uracils (poly-Us) were embedded between the ssL and triangle vertices. This resulted in the formation of a "face-to-face" dimer with a total of 8 RNA strands. The overall geometry was manually computed using SwissPDB Viewer software [34], the structure resembling triangular prism geometry with the pRNA-3WJ motif at the corners. The 3D RNA model displays a size of ~11 nm, measured from one vertex to an adjacent vertex, and a size of ~10 nm measured from one vertex to its nearest edge, as measured by the modeling software (FIG. 6B). The largest diameter of the inner cavity of the prism was measured to be ~7 nm while the height was ~6 nm. Based on these dimensions, we assume that the central cavity of the prism could accommodate a spherical object of approximately 6 nm in diameter.

Figure 7A:
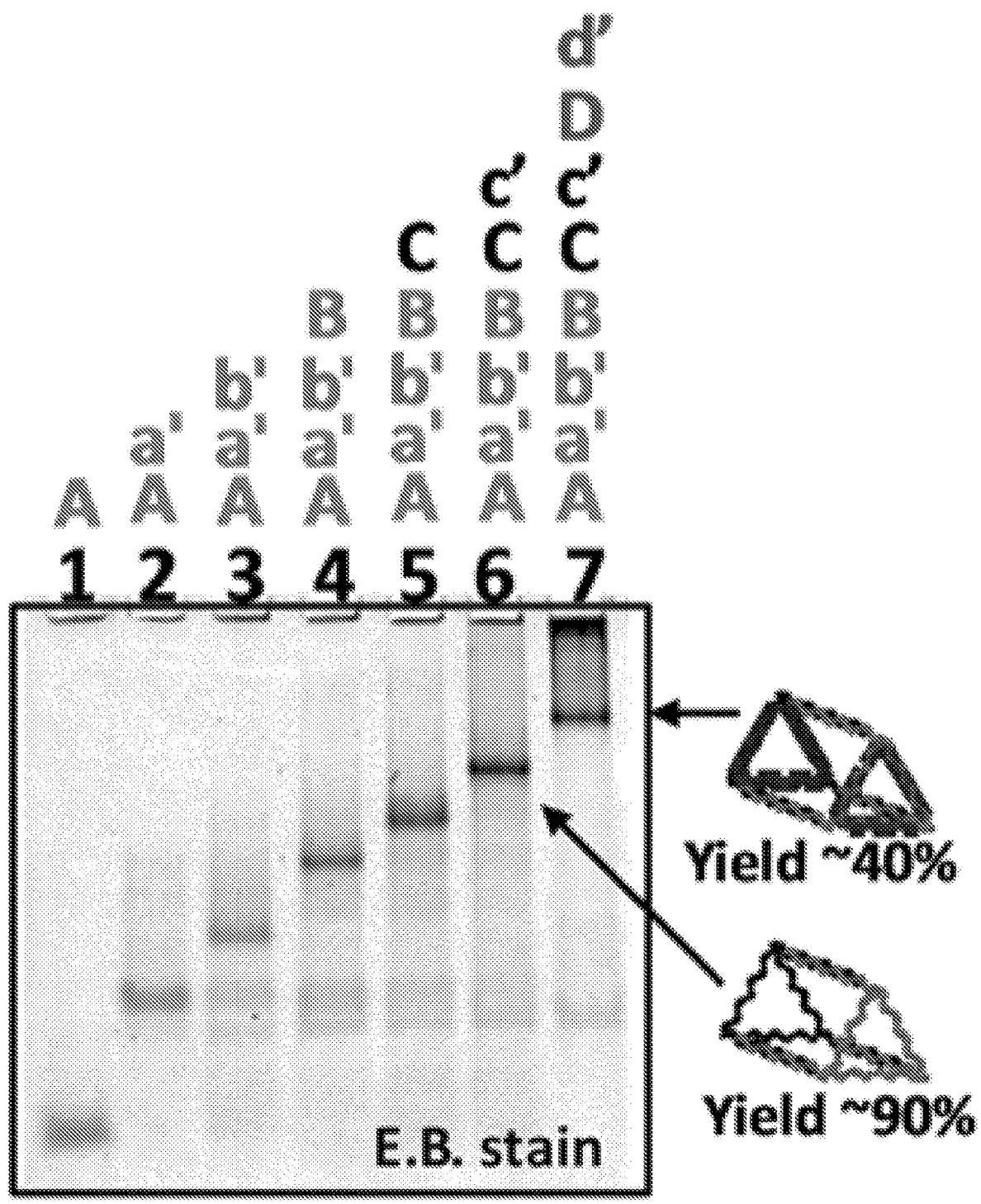
FIGS. 7A-7E demonstrate RNA Triangular nanoprism self-assembly and characterization.

Assembly efficiency of the RNA strands into the desired conformation was first assayed by 6% native polyacrylamide gel electrophoresis (PAGE). Upon addition of each of eight component strands, a step-wise decrease in electrophoretic migration can be clearly seen, indicating association of each complimentary ssRNA oligomer into the complex RNA structure (FIG. 7A). The distinct band in lane 7 indicates the formation of a stable RNA complex containing all 8 RNA strands. Integration of the intensity of gel bands results in an estimated assembly yield of 43.0±3.1%. A large fraction of RNA aggregates are localized in the top of lane 7. Presumably, this is due to non-specific interactions between the 21nt RNA single stranded sticky ends. Interestingly, the RNA complex with no D and d' stands has much higher assembly efficiency with estimated yield of 90% (FIG. 7A lane 6).

Figure 7B:
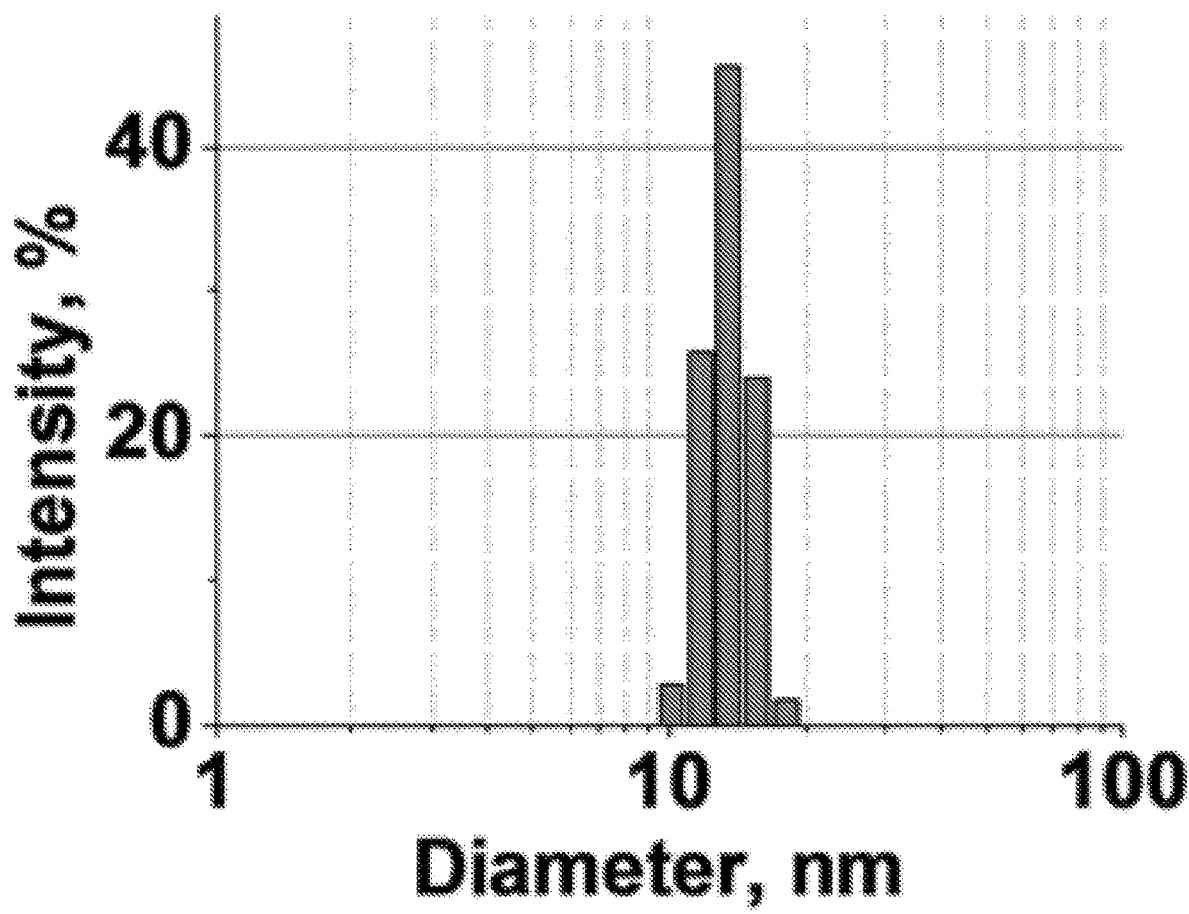
Figure 7C:
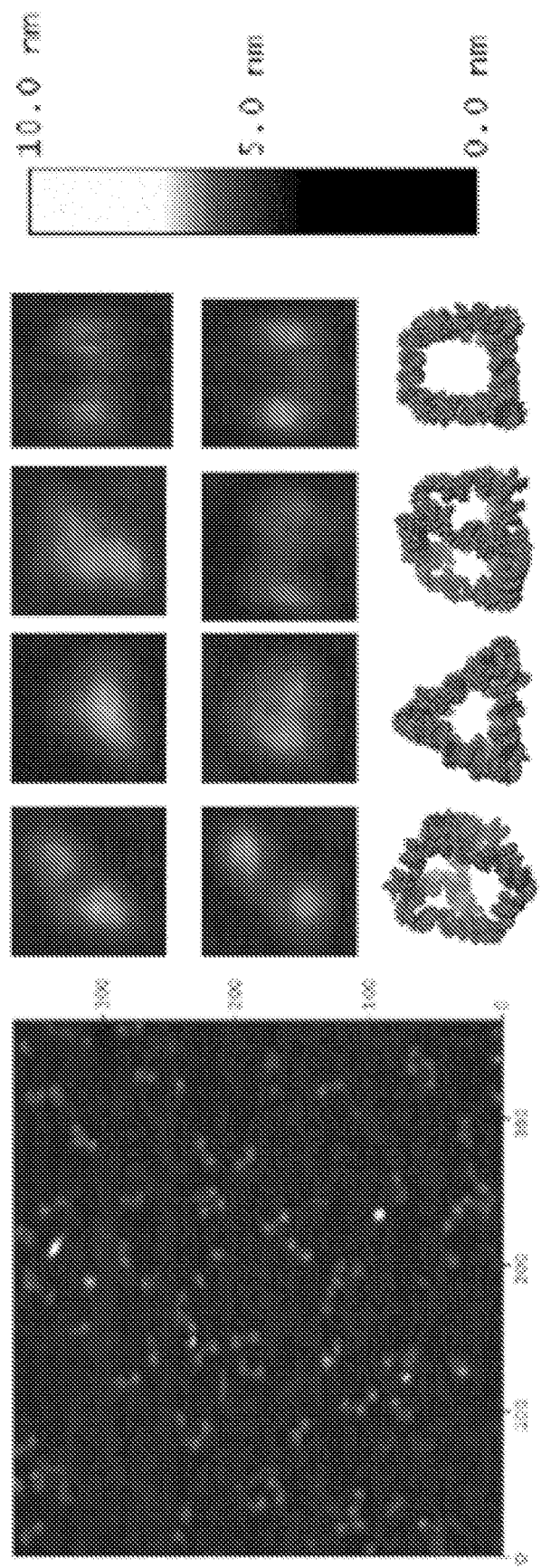

DLS was utilized to measure the apparent dimensions of the purified RNA prism. As measured by DLS, the hydrodynamic diameter of the RNA complex is 11.5±1.6 nm, consistent with the 3D model structure of the nanoprism (FIG. 7B). AFM imaging of the pure RNA complex has revealed that the particles do in fact display prismoidal-like architecture (FIG. 7C). AFM is 2D observation of the 3D RNA prism and cannot be used to conclusively indicate the formation of the triangular prism geometry, nevertheless, the particles do resemble the designed triangular prism in two dimensional projections.

Cryo-EM Imaging Studies Revealed Triangular Prism Geometry

Figure 7D:
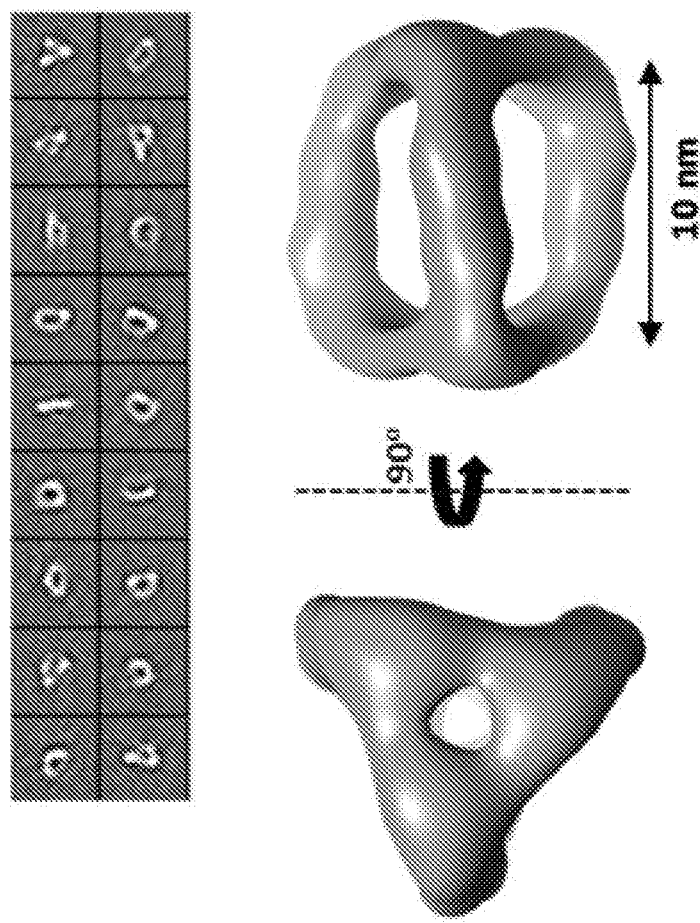
Figure 7D:
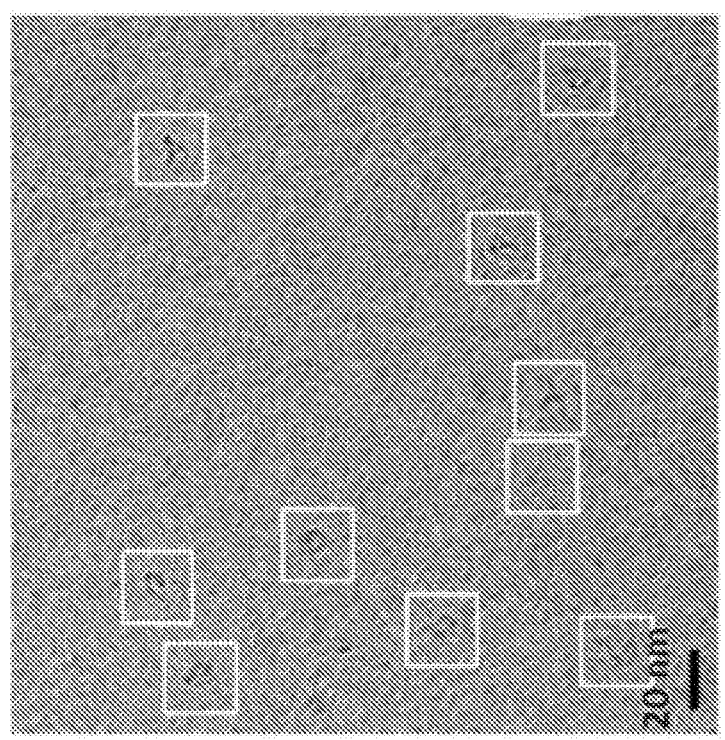
Figure 7E:
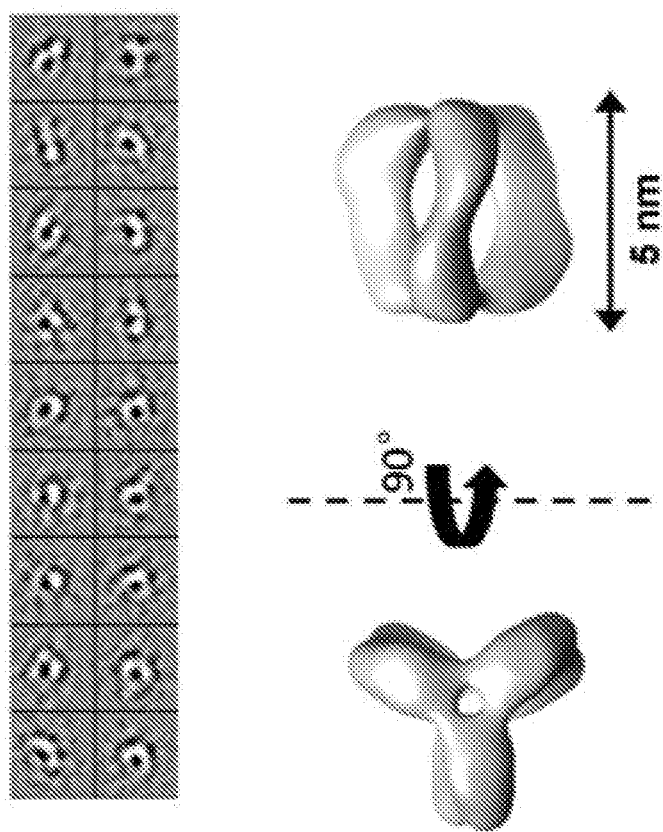
Figure 7E:
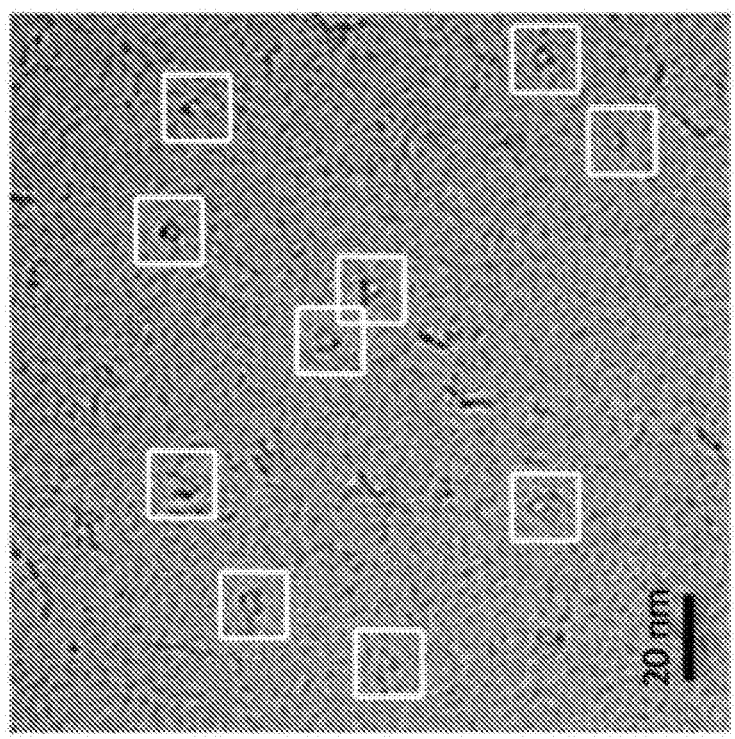

To address the concern whether the folding of 8 RNA stands resulted in 3D geometry, the purified RNA complex was visualized by single-particle cryo-electron microscopy (cryo-EM) (FIG. 7D, 7E). Cryo-electron microscopy is a useful method to show the true 3D nature of the RNA nanoprisms, as AFM analysis causes distortion of 3D nanoparticles imaged in 2D[35]. The 3D reconstruction of the RNA nanoparticles was achieved implementing single-particle reconstruction using the EMAN2 approach as described in the methods section. Reconstruction of the 3D structure of the RNA complex were determined at a resolution of 2.5 nm (10 nm RNA prism) and 2.2 nm (5 nm RNA prism), and demonstrated that the RNA particles have an average sizes of 10 nm and 5 nm, respectively, in agreement with DLS and AFM results. More importantly, the overall geometry is similar to the computer modeled 3D RNA prism. It is important to note that the reconstruction of the RNA prism by Cryo-EM clearly demonstrates the presence of an inner cavity. Collectively, the data from native PAGE, DLS, AFM, and Cryo-EM clearly indicate the formation of closed and compact RNA nanoprisms.

Design and Construction of RNA Aptamer Encapsulated Nanoparticle.

The MGA is a commonly used tool in biochemistry for structure-function verification [36-38]. This is attributed to its unique properties as free MG dye in solution displays little to no fluorescent signal, yet when bound to MGA the photoemission increases more than 2000-fold[39,40]. However, fluorescence can only occur if the RNA MGA folds into its authentic 3D conformation. Previous attempts to achieve fluorescence using 2'-F modified RNA bases resulted in little to no fluorescence [26]. Therefore, for RNA MGA to remain a useful tool within a cellular environment, it must be placed into a container that will protect the RNA from a degrading environment. This is a common problem among many small RNAs and small molecule drugs with therapeutic utility. Using 2'-F modified RNA to construct the prism's frame (2'-fluoro uridine (2'-F-U) and 2'-fluoro cytosine (2'-F-C)), which are known to display resistance to a degrading environment [41], it was hypothesized that the RNA MGA will be protected when positioned inside the 2'-F modified nanocage.

Figure 8A:
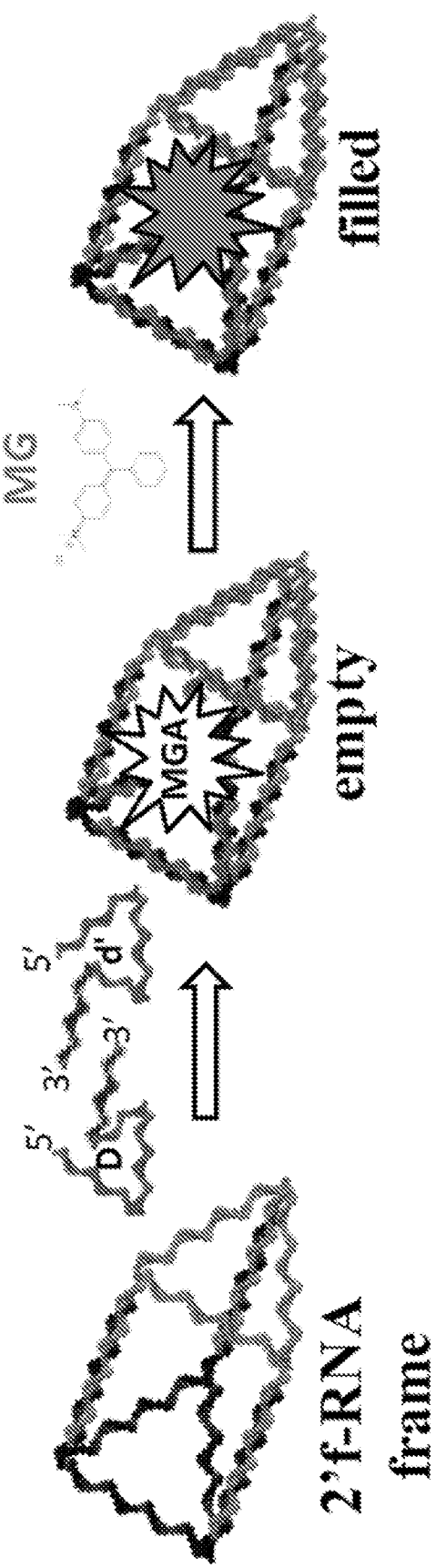
FIGS. 8A-8E demonstrate encapsulation of the RNA MGA and results of a fluorescence assay.

As a proof-of-principle, the MGA RNA sequence was employed by embedding it within the "D" and "d" strands at their 3' ends. The schematic encapsulation design is summarized in FIG. 8A. Throughout this Example, reference is made to the stable RNA complex formed by six 2'-F modified RNA strands without D or d' strands as a "frame". It was interesting to find that this complex is highly stable with apparent melting temperature (TM) of 74° C., with the assembly efficiency being Mg2+ dependent.

Using SwissPDB Viewer, the complex structure of the RNA nanocage with encapsulated MGA was first modeled by positioning the 3D structure of the MGA inside the inner cavity formed by the Nanoprism. This allowed for estimation of the distance constraint in base pairs required to mount the RNA MGA (extracted from PDB ID: 1F1T [24]) into the inner cavity of the prism. The complexation of the RNA MGA within the nanocage was evaluated on native PAGE. The apparent gel shift of the band localized in lane 4 (2'-F-RNA frame with MGA) compared to lane 1 (2'-F-RNA frame only) shows complexation of the MGA sequences with the frame structure detected by total RNA stain with Ethidium Bromide (EB). Staining of the same gel in the presence of MG dye resulted in strong fluorescence emission from the distinct band on lane 4, indicating correct folding of the RNA MGA. Additional control experiments were performed based on migration properties of the closed (compact) and open (relaxed) 3D RNA complexes as it is generally accepted that more compact RNA structures migrate faster in comparison to relaxed RNA conformations. To fabricate the open 3D prism conformation, the interaction of one of the complementary sticky ends linking two RNA triangle together were intentionally disrupted though sequence design. Comparing migration of the open RNA prism to the closed version revealed slight differences in migration distance. This indicates that the prism is closed and that the MGA was located, presumably, within the inner cavity of the nanocage. Data obtained from the mobility shift assay alone do not provide a concrete conclusion whether the RNA MGA formed inside of the closed cage; additional data supporting this assumption comes from RNase T1 cleavage experiments as described below.

RNase T1 Protection Assay Confirmed the Encapsulation of the MG RNA Aptamer by the Nanocage.

Encapsulation of an RNA module inside the negatively charged RNA nanoprism is challenging due to the repulsion forces caused by the negatively charged phosphodiester backbone of both the inner cavity of the RNA cage and the RNA MGA. Development of a method to overcome this challenge would be exceptionally beneficial as the activity of functional RNA modules could be retained by protecting them from enzymatic degradation in vivo. To further confirm that the RNA MGA was localized inside the cavity of the nanocage, the RNA complex was treated with endonuclease RNase T1, which specifically cleaves unpaired guanosine (Gs) nucleotide[42]. While the single stranded Gs are absent from the 2'-F-RNA prismoidal construct, there are several ss Gs present in the RNA MGA itself that are essential for MG binding. Thus, it was hypothesized that RNase T1 will cleave the exposed Gs of the MGA sequence resulting in the loss of fluorescence. However, if the cage were to restrict RNase T1 access to the MG aptamer within the nanoprism, fluorescence emission would be retained or decay at a slower rate.

Figure 8B:
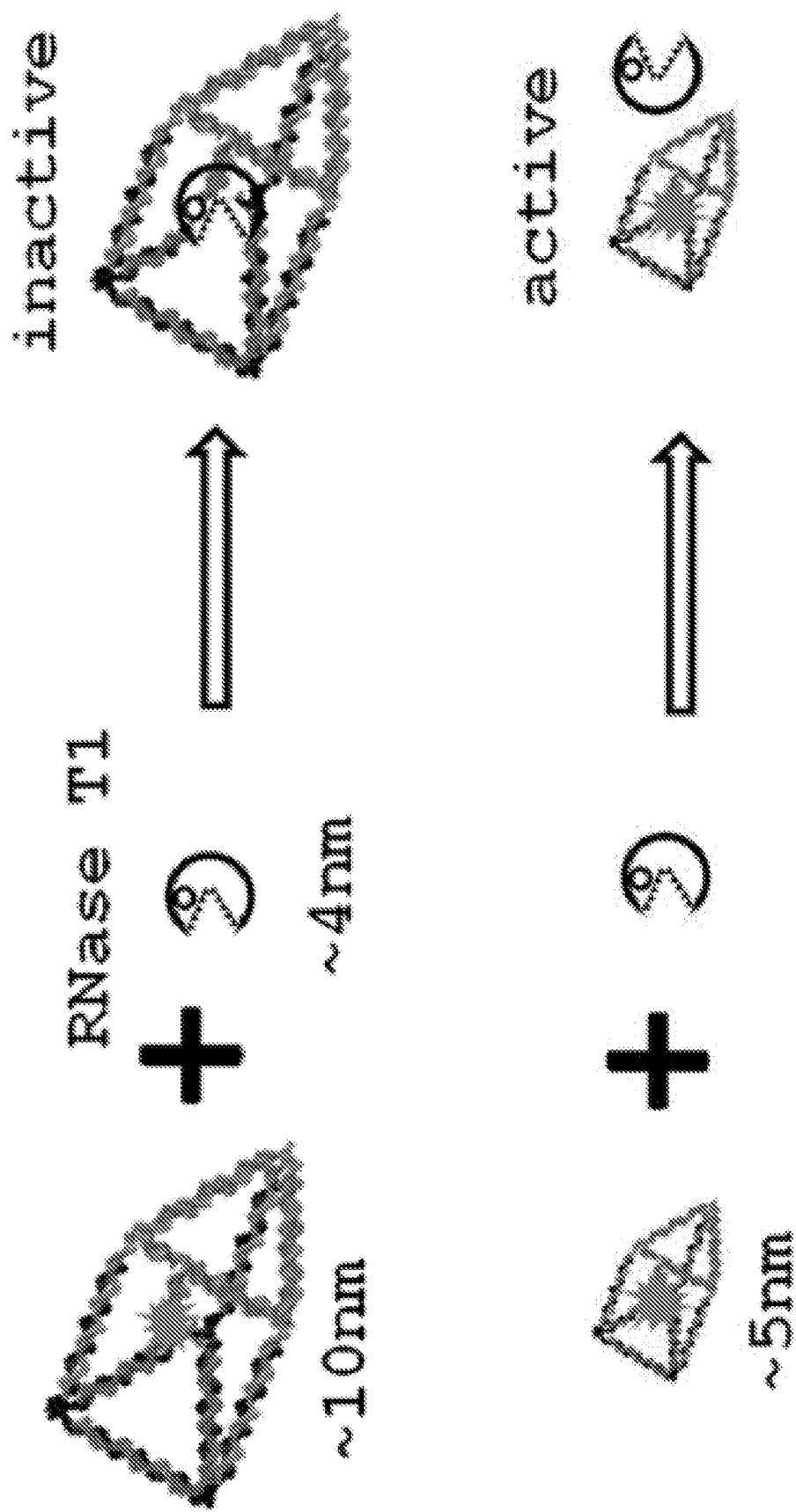
Figure 8C:
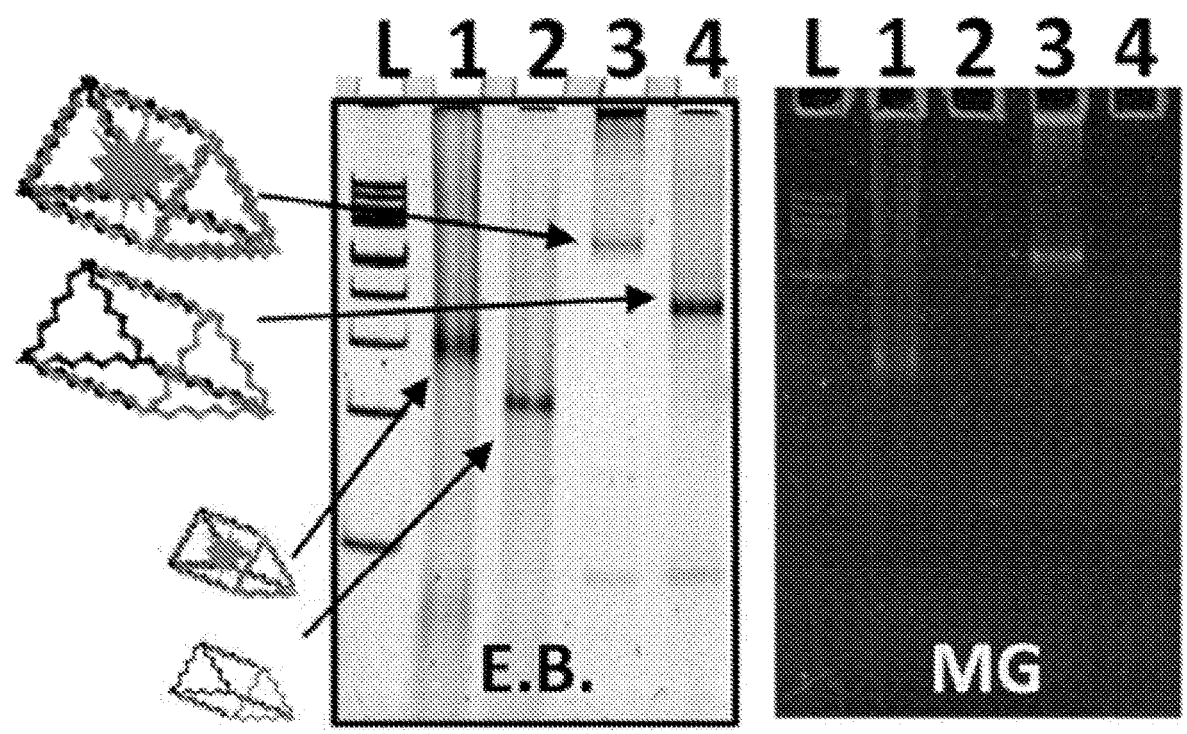
Figure 8D:
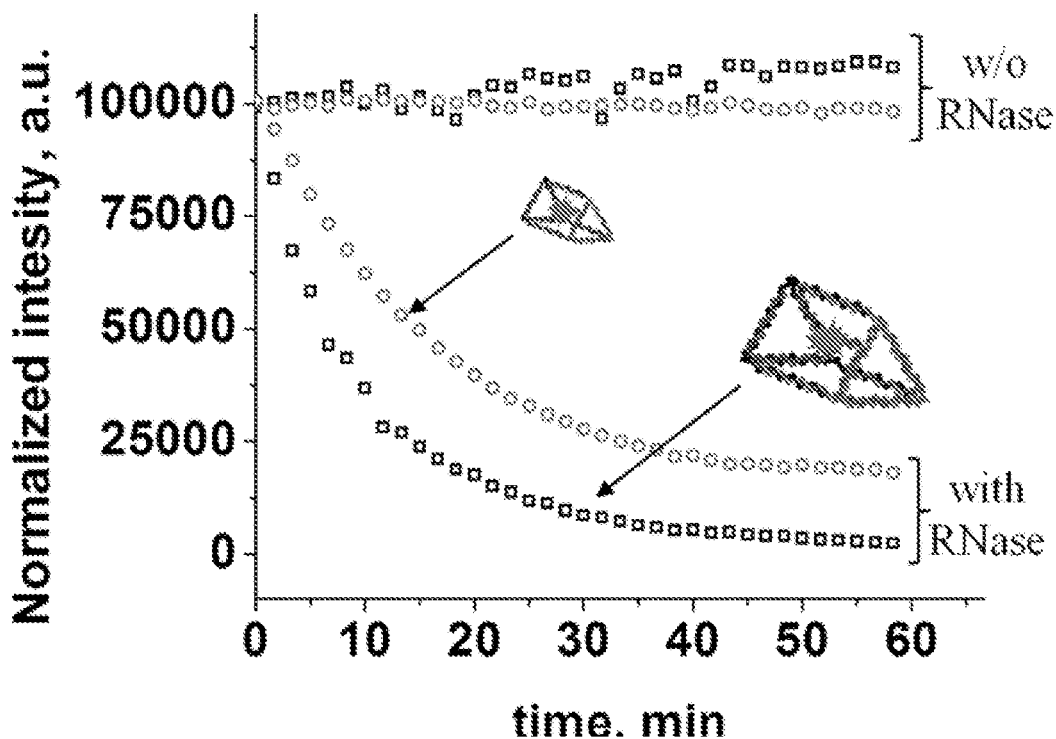
Figure 8E:
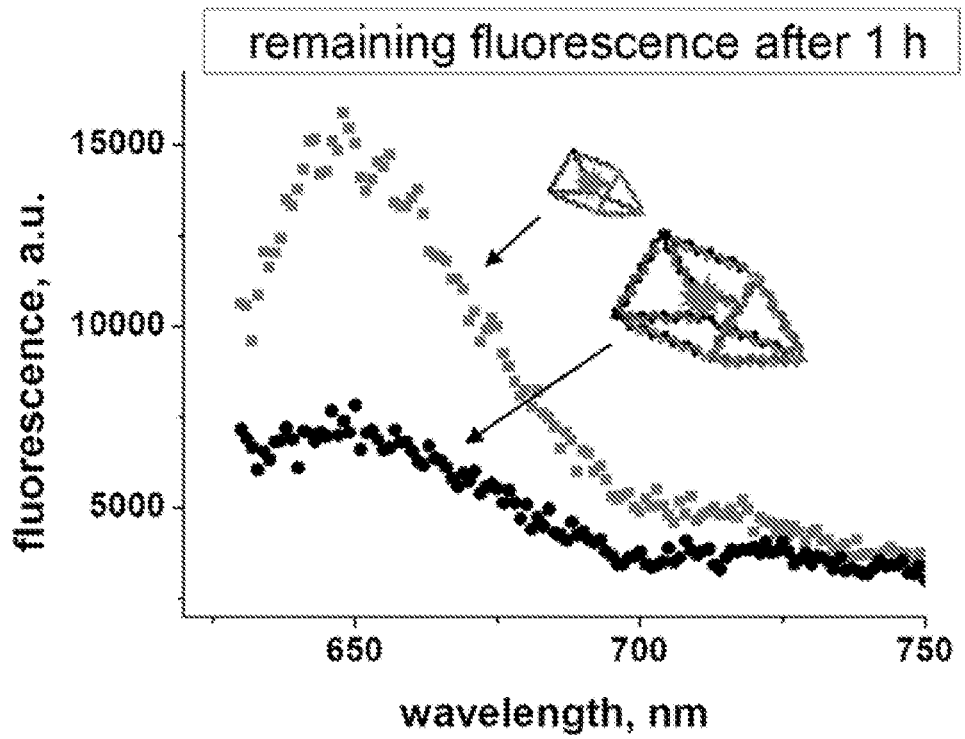
Figure 8F:
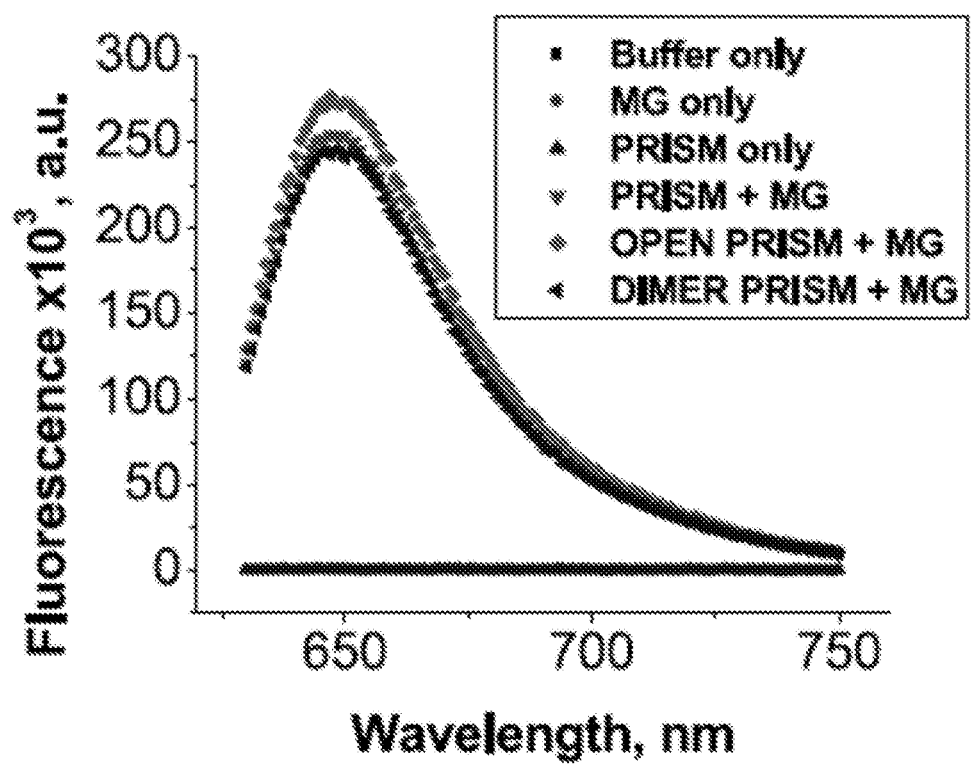
FIG. 8F shows a graph demonstrating the fluorescence properties of the same RNA complexes in solution.
Figure 9A:
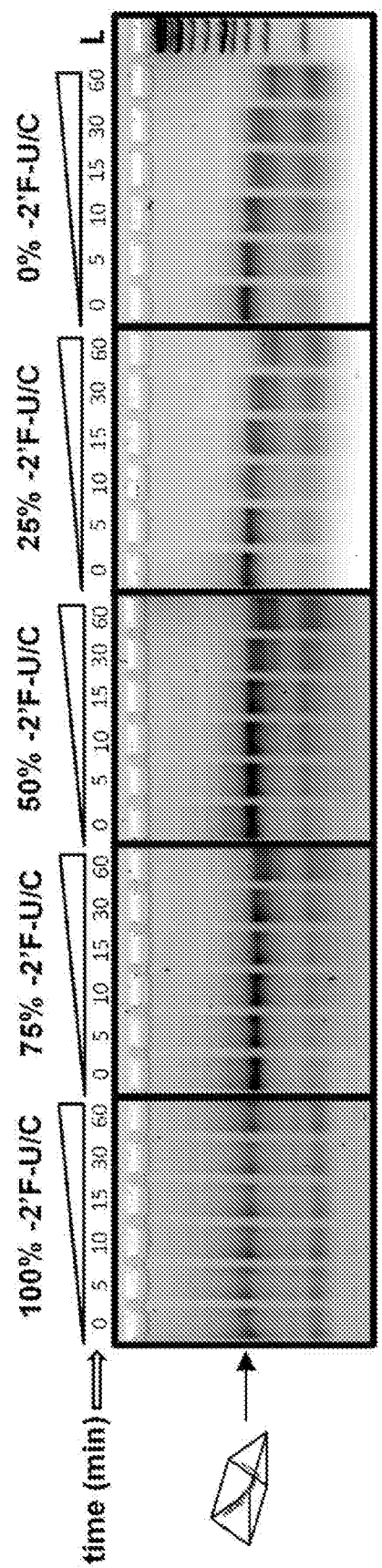
FIGS. 9A-9B demonstrates a tuning degradation profile of nanoprism in fetal bovine serum.
Figure 9B:
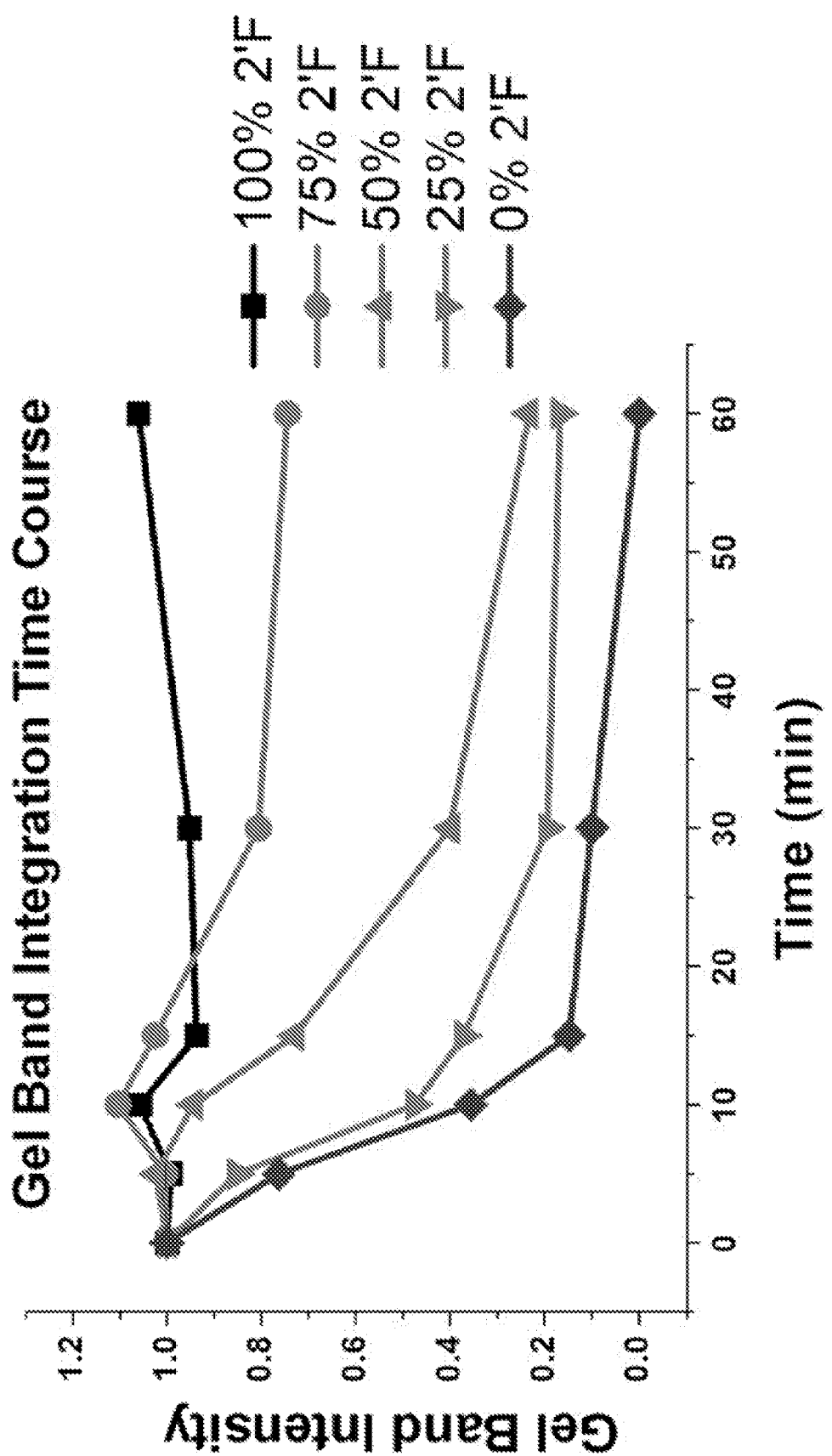
Figure 10A:
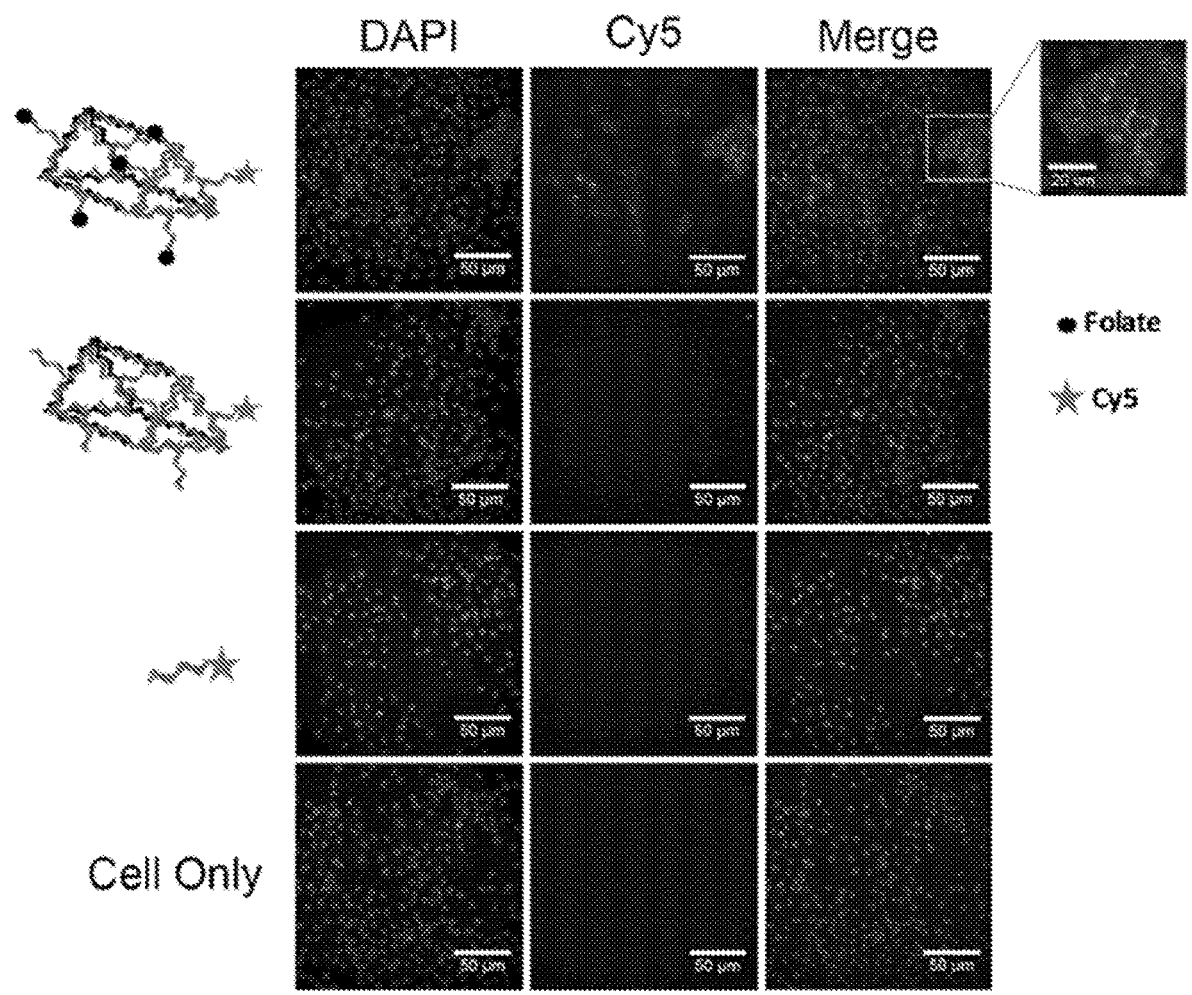
FIGS. 10A-10B demonstrates the results of an evaluation of the RNA triangle prism to carry functional moieties.
Figure 10B:
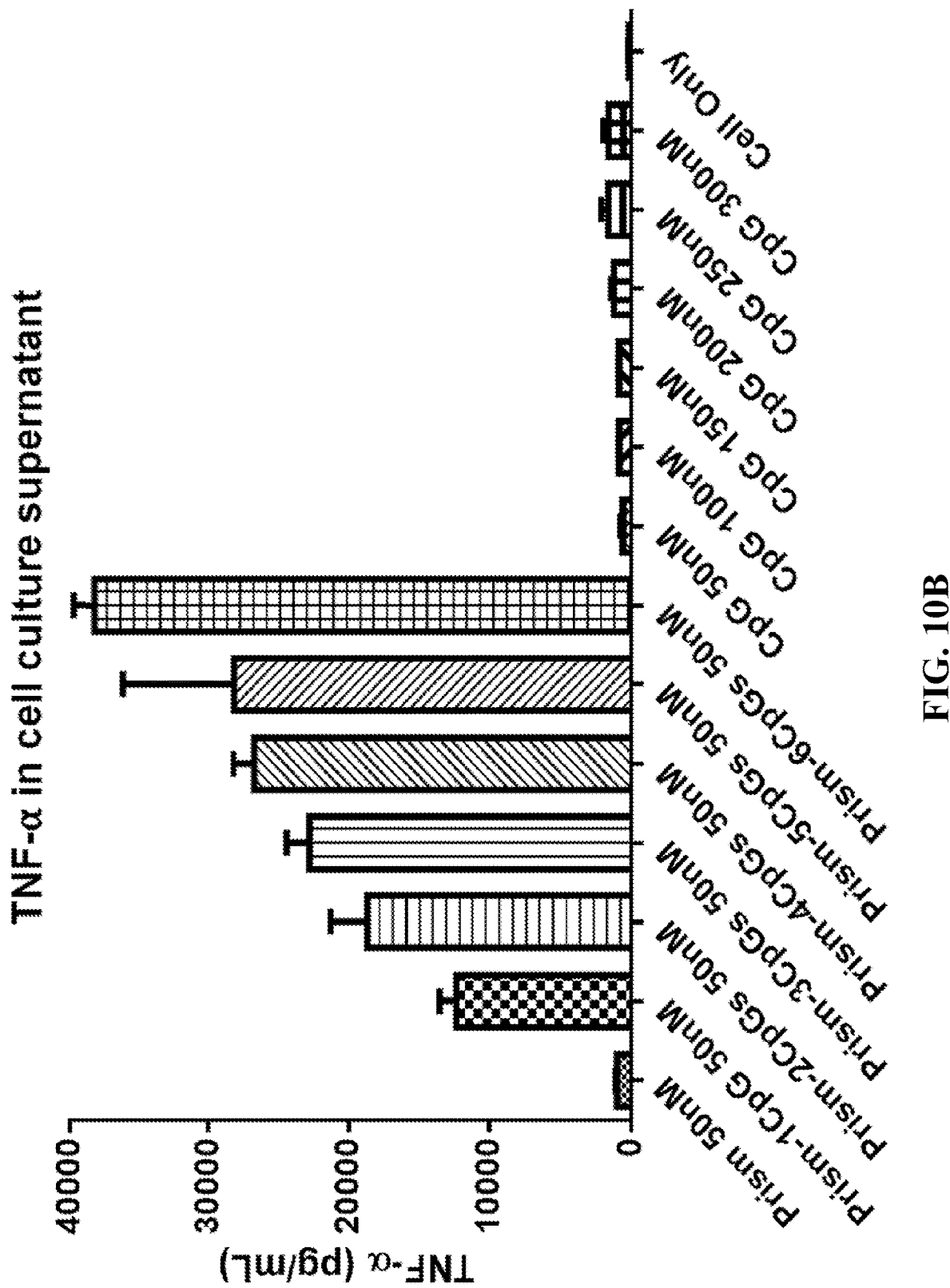
Figure 11A:
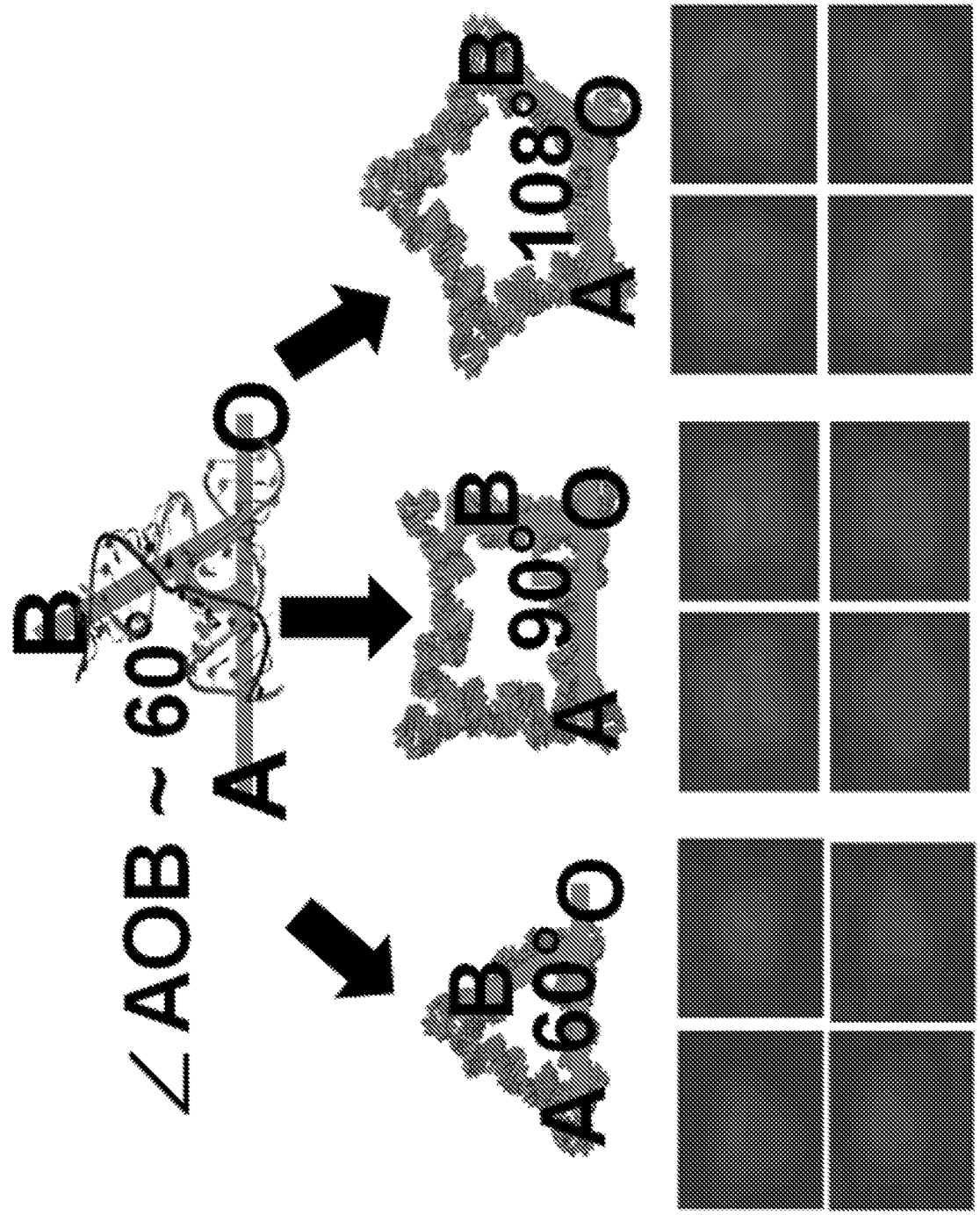
FIGS. 11A-11D demonstrate construction of 3D RNA nanocages for targeted delivery of therapeutics to tumors.
Figure 11B:
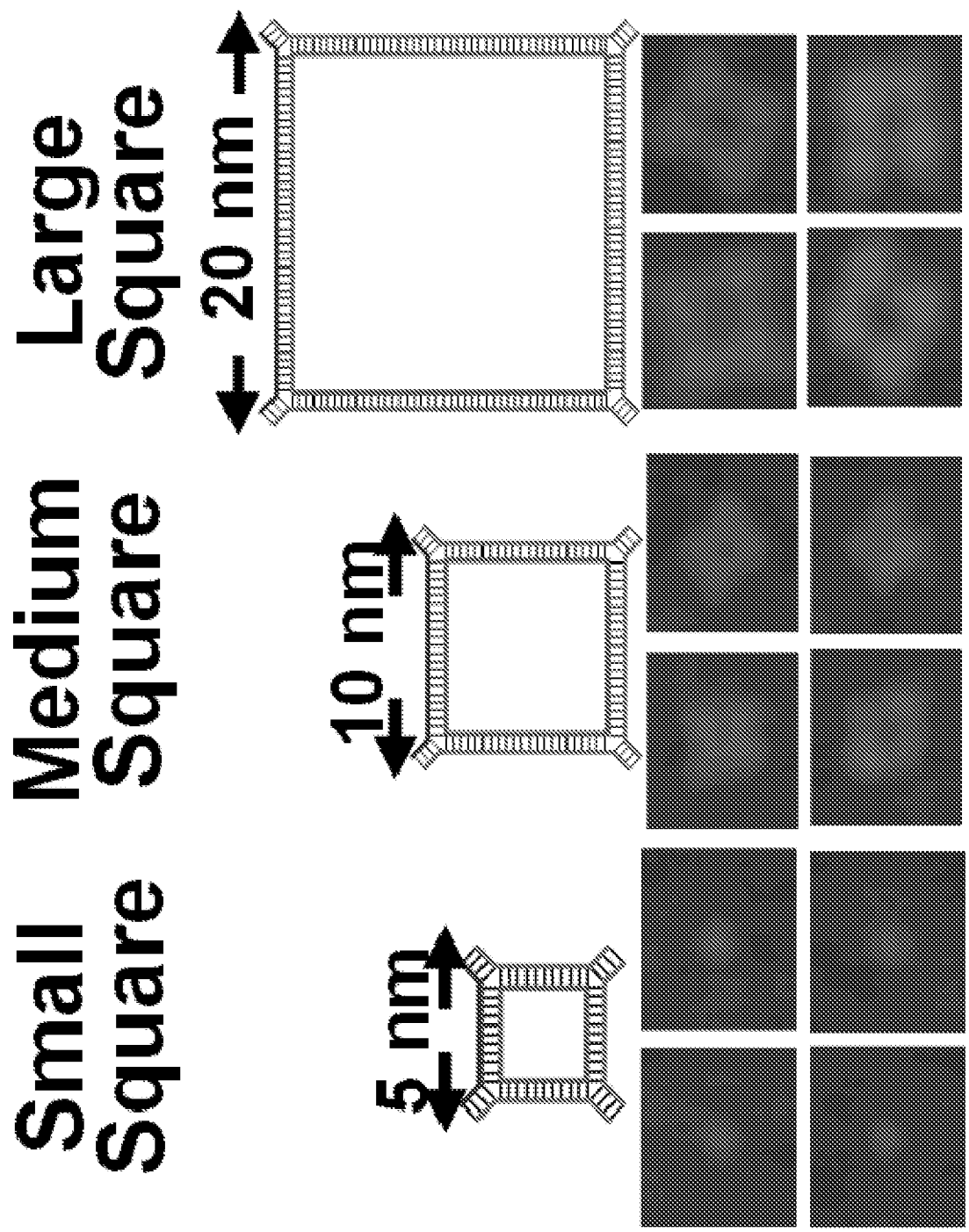
Figure 11C:
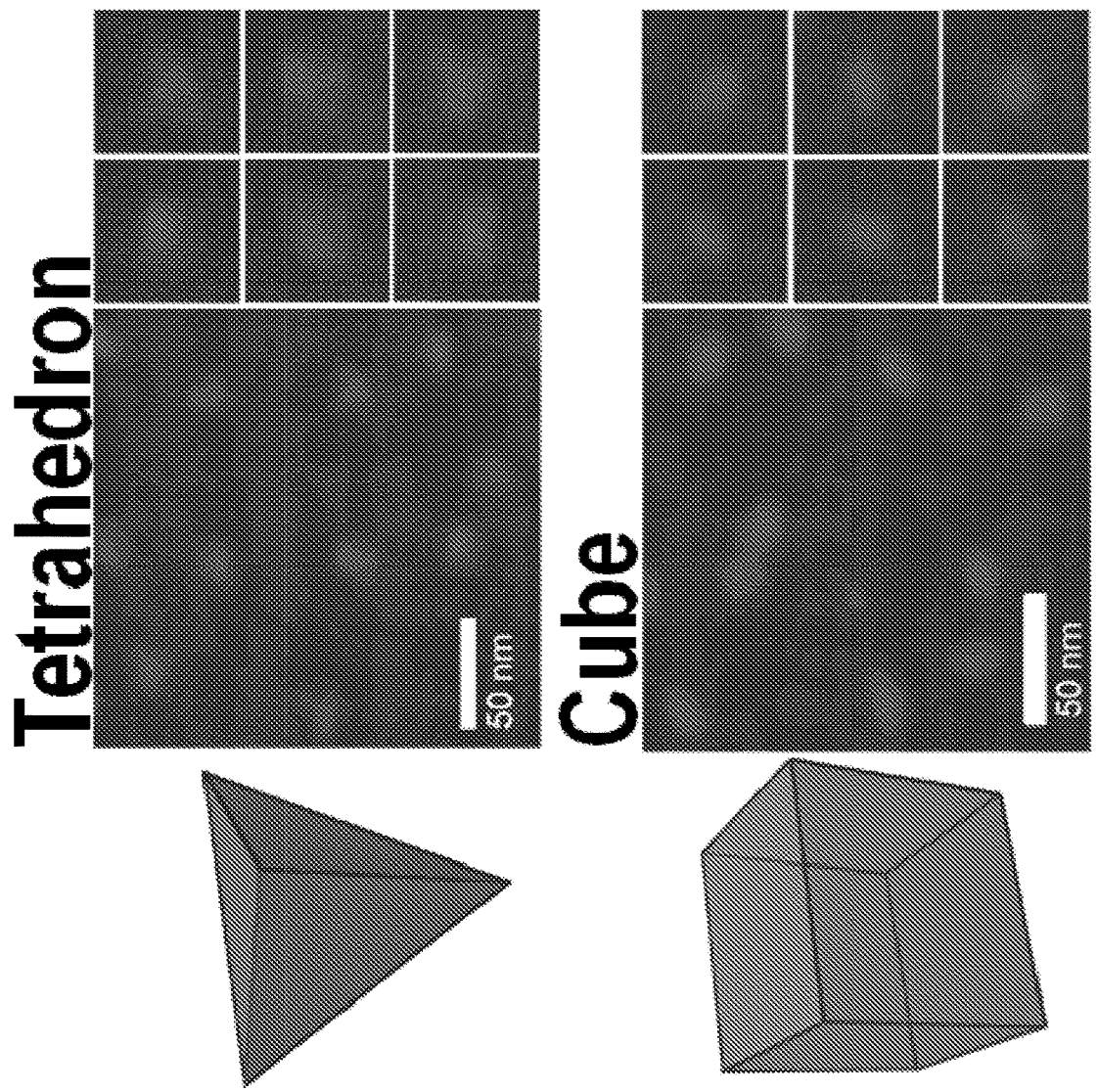
Figure 11D:
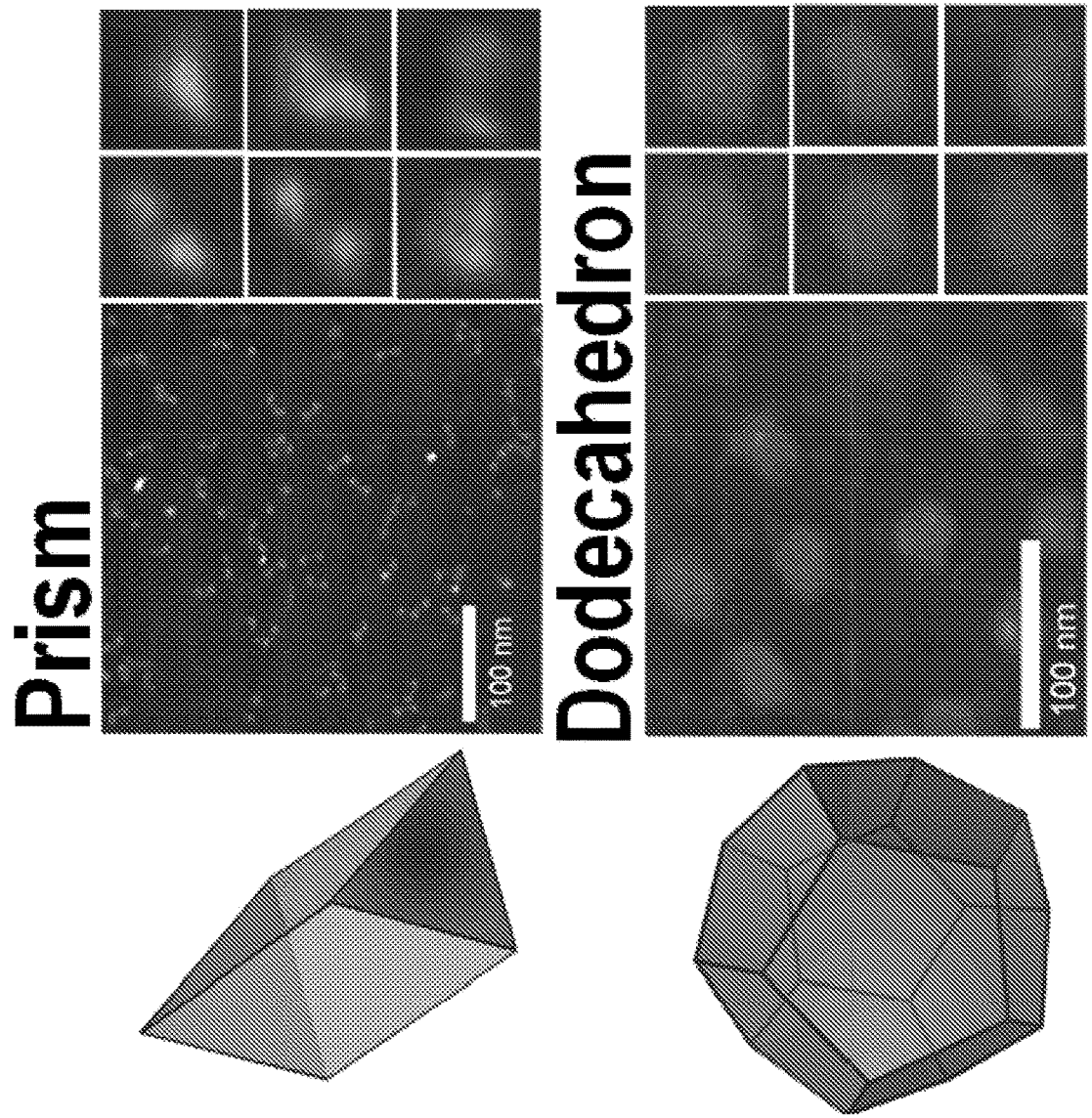

According to the modeled 3D structure of the prism, the estimated average dimensions of the inner cavity of the prism could accommodate a spherical object of about 6 nm. The average size of the RNase T1 structure was measured (PDB ID: 1YGW) to be 3.7 nm in diameter [43] allowing RNase T1 to easily access the inner cavity and quench the fluorescence of the MGA. To address this obstacle, a nanoprism having a smaller cavity size of 3 nm was designed by decreasing the length of the RNA prism helical regions by one half. The schematic design of the experiment is summarized in FIG. 8B. The smaller prism is expected to insulate the MGA from RNase T1 cleavage, thus extending fluorescence activity The assembly of the small prism is highly efficient, and RNA MGA is functional according to native PAGE analysis (FIG. 8C, lanes 1 and 2). Next, time-dependent MG fluorescence decay was carried out in the presence of RNase T1 to test the activity of the MGA embedded inside the large and small nanoprisms. FIG. 8D shows the fluorescence exponential decay profiles of the large (squares) and small (circles) nanoprisms. The calculated lifetimes ($\tau$) were found to be 445.5 sec and 781.4 sec for the large and small nanoprisms respectively. The small prism displayed a half-life almost double that of the large prism, suggesting that RNase T1 has limited access to MGA encapsulated inside of the small nanoprism. Complete protection against RNase T1 has not been observed presumably due to the dynamic nature of the interacting linker arms of two triangles. This is also supported by AFM images where significant fractions of prisms are in an open state, which allows RNase T1 to digest the MGA. Notably, fluorescence emission of the small prism was still observed after 1 hour of incubation with RNase T1 while fluorescence in the large prism was negligible (FIG. 8E). Additional control experiments were performed using a variety of other RNA control complexes containing RNA MGA. The calculated values of T are summarized in Table 1. Mean lifetime comparison of the small RNA prism to the controls demonstrates that no control construct has greater $\tau$ than the small prism. Thus, the RNase T1 cleavage assay indicates the successful encapsulation of MGA encapsulated in both the small and large nanocages. More importantly, we have shown that by tuning the size of the inner cavity, fluorescence half-life can be significantly increased. This is synonymous with increasing the release time of a drug that can be potentially used an in vivo system.

TABLE 1

Fluorescence life times of different RNA constructs

| Nanoparticle type and structure | Triangle prism | Control 1 | Control 2 | Control 3 | Small prism |
|---|---|---|---|---|---|
| Life time $\tau$, sec[a] | 445.5 ± 50.0 | 352.3 ± 47.8 | 273.2 ± 39.3 | 386.5 ± 45.6 | 781.4 ± 43.0 |

[a]The standard error of the mean obtained from at least three independent experiments Encapsulation of Oligonucleotide-Drug Conjugates Inside the Nanocage Taking advantage of the programmability of the D and d' prism strands, next demonstrated was the encapsulation of single stranded oligodeoxynucleotides (ssODN) containing functional moieties such as fluorescence reporters and drugs. To this end, one long ssRNA was designed to connect D and d' strands through a 22 nt linker. The resulting RNA sequence is referred as a "core" RNA strand. While the 5'- and 3'-ends of the core RNA strand interact with the triangular edges of the prism, its single stranded middle region is designed to localize inside the nanocage. The portion of the core strand inside the prism was utilized for encapsulation of either ssDNA or ssRNA carrying different functional groups via base pair hybridizations. Hence, it is anticipated that the encapsulation of the functional moieties will prevent them from enzymatic degradation and increase their cellular lifetime. Alternatively, this principle can be applied as a safety mechanism. For instance, carrying highly toxic compounds that should be released only upon reaching its target.

Due to the programmable nature of the RNA prism, the size of the nano-container can be adjusted by simply increasing or decreasing the sides of the prism by complete helical turns as shown previously [41,44]. This is advantageous as the capacity of the RNA nano-container can be controlled enabling encapsulation of diverse size biomolecules or inorganic nanoparticles, as well as increase the payload of a single nano-container for increased detection sensitivity and increased efficacy in the treatment of disease. Moreover, from a medical point of view, size alternation of the nanoprism imparts differences in toxicity, cellular binding and internalization, renal clearance, physicochemical features, as well as pharmacokinetics and pharmacodynamics profiles. As such, the prismoidal nano-container provides a unique system to further exploit these factors.

Figure 20A:
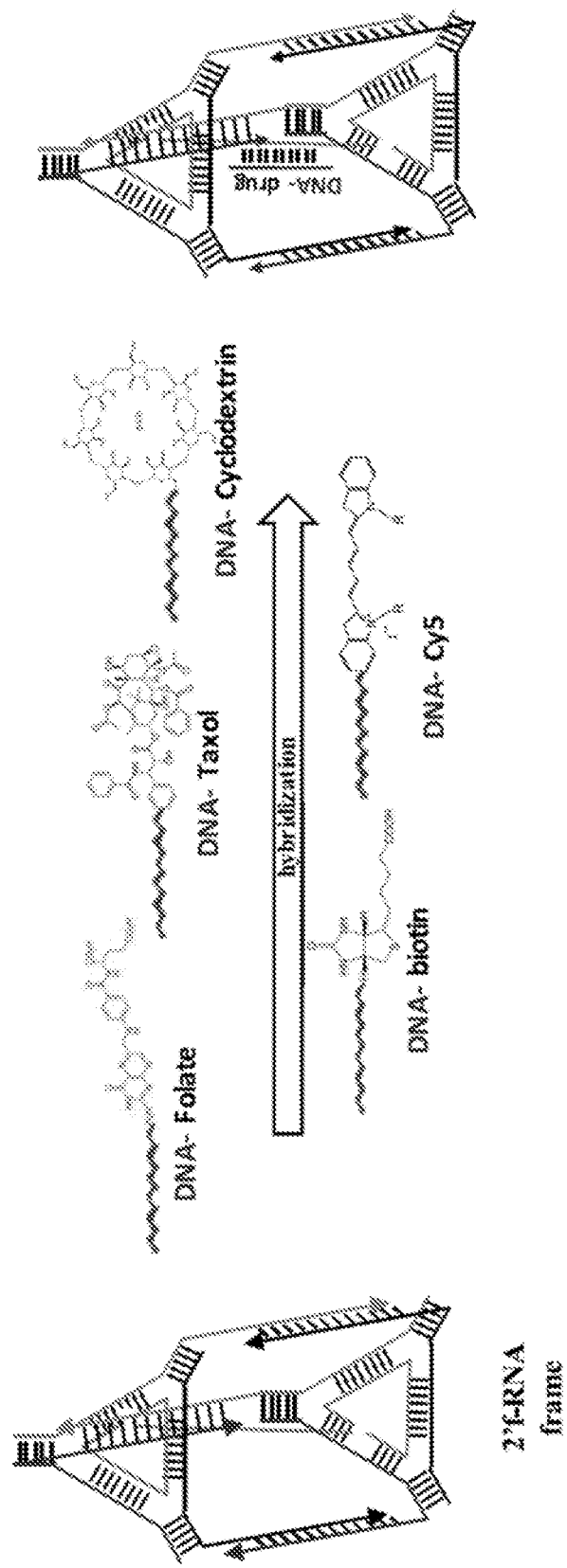
FIGS. 20A-20B can demonstrate encapsulation of various DNA-drug conjugates by the RNA 3D nanocages.
Figure 20B:
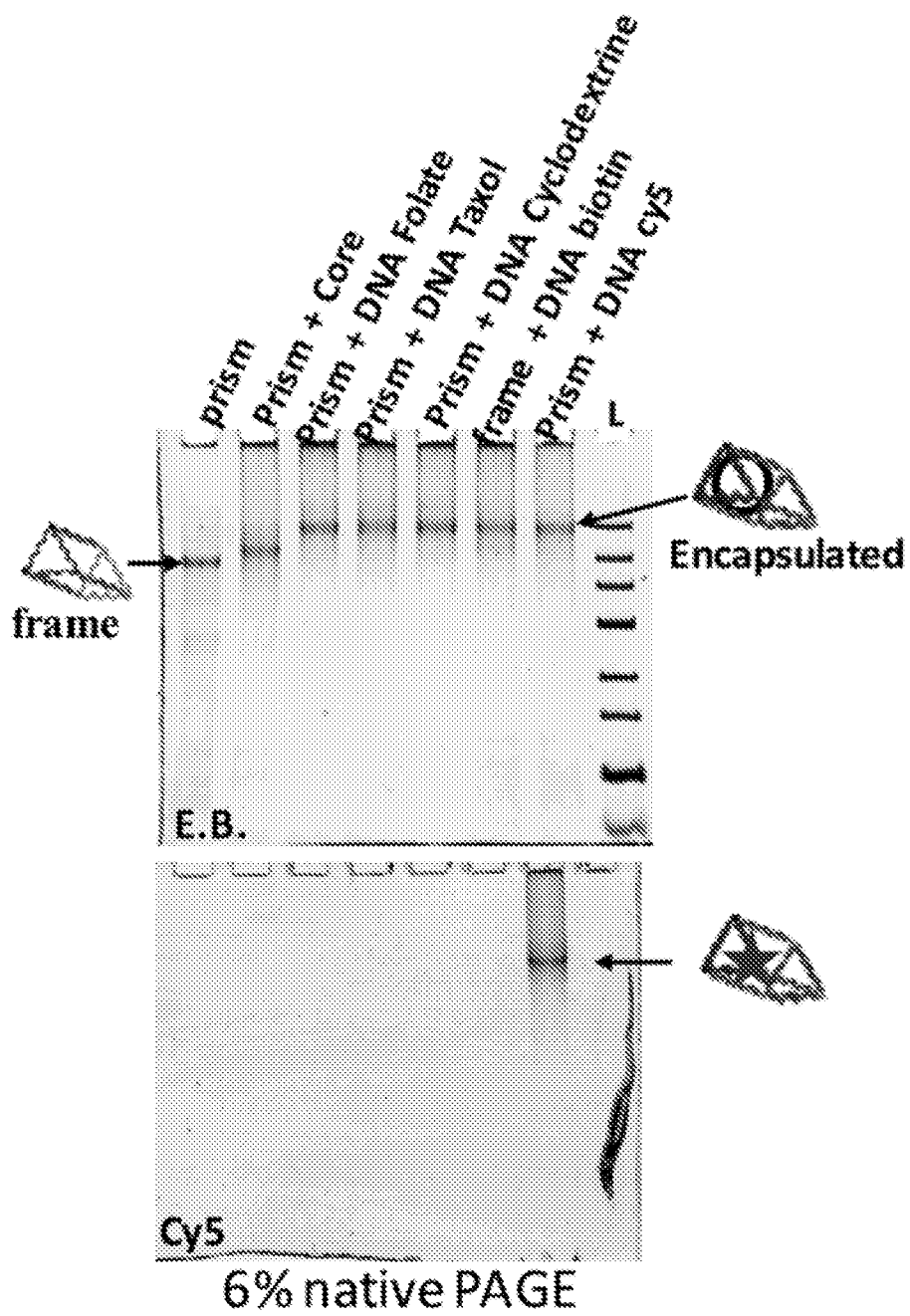

The design scheme is illustrated in FIG. 20A. The principle behind chemical drug encapsulation relies on the conjugation of a drug at the 3'/5'-end or at both ends of DNA/RNA oligonucleotides, followed by hybridization of this conjugate inside the cavity of the RNA nanoprism. To demonstrate this in practice, short DNA sequences (22nt) labeled at the 5'-end with different chemicals including folic acid (FA), cyclodextrin, taxol, Cy5 fluorophore, and biotin were used. To verify the formation of the RNA nanoparticle with the conjugated DNA sequence, prism strands and corresponding DNA oligonucleotides were assembled in one-pot by mixing at equimolar concentrations, followed by native PAGE analysis. PAGE analysis results are demonstrated in FIG. 20B. There were distinct bands corresponding to the frame structure and frame containing the core RNA sequence (lanes #1 and 2 on the native PAGE shown in FIG. 20B). The additional lanes correspond to loaded nanocage with the 22nt DNA containing a variety of small molecules. Based on the slower rate and almost identical distance of all five loaded cargoes as compared to the bands in lanes 1 and 2, we can conclude that the conjugated ssDNA were successfully hybridized inside the nanocage structure. Additionally, co-migration of Cy5 and EB signal of Cy5 loaded nanocage indicates correct assembly.

Figure 20C:
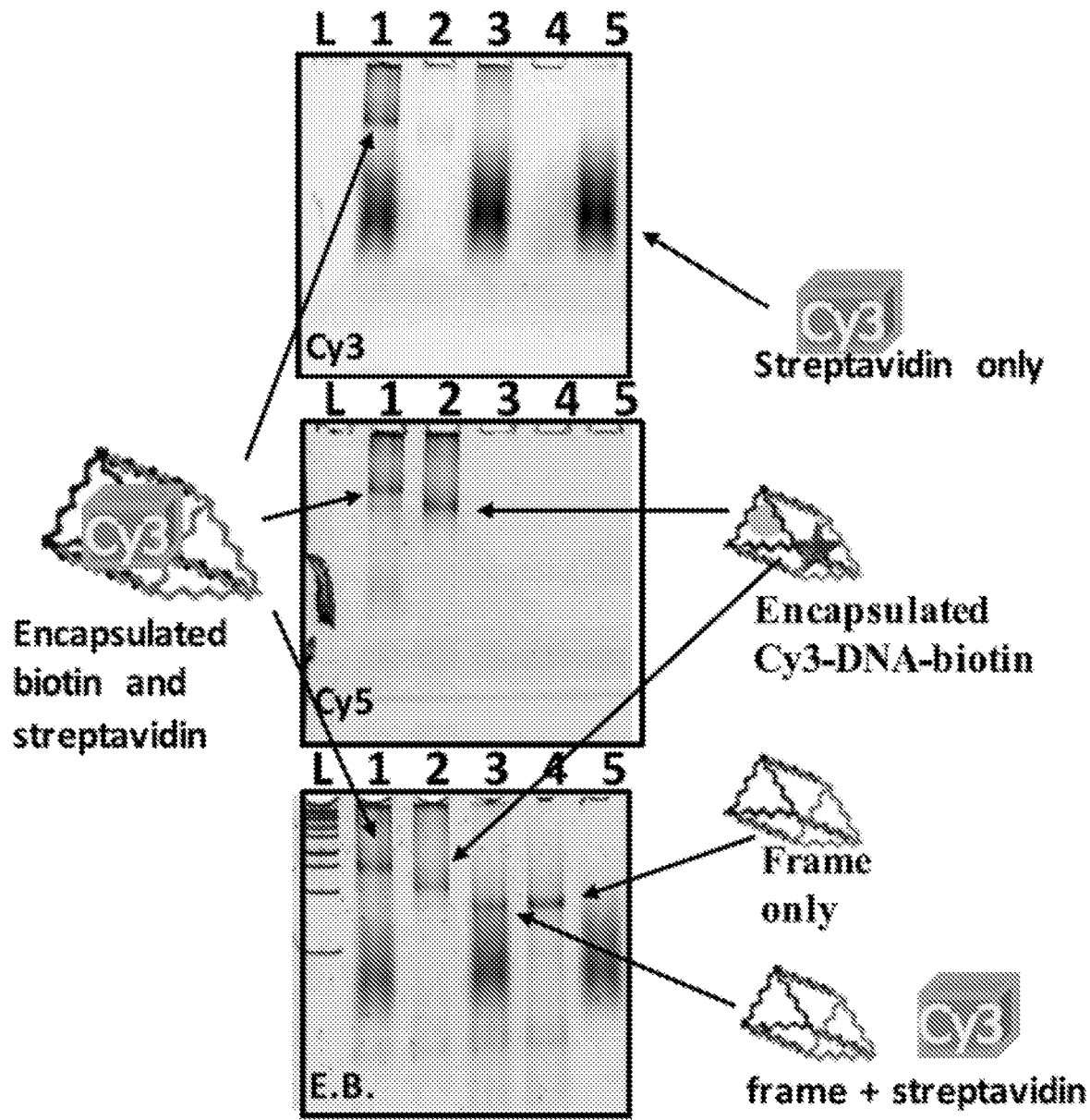
FIG. 20C shows the representative results from an electro mobility shift assay and fluorescence localization experiments conducted on native 6% PAGE. The final encapsulated complex on Lane 1 obtained by incubation of encapsulated Cy5-DNA-biotin in the presence of saturated amount of Cy3-streptavidin. Lane "L" corresponds to the DNA ladder (Thermo Scientific O'GeneRuler 1 kb).

To demonstrate incorporation and function of the DNA-biotin conjugate within the RNA 3D cage, biotin-streptavidin binding was utilized[45]. The results are demonstrate in FIG. 20C. To separately visualize the biotin-nanoprism and the streptavidin, the DNA-biotin conjugate was tagged with Cy5 and the streptavidin with Cy3. The ensuing gel shift assay demonstrated complexation between the encapsulated biotin and streptavidin as the complex migrates much slower than the biotin-nanoprism or streptavidin alone. Colocalization of EB (RNA), Cy3 (streptavidin), and Cy5 (DNAbiotin)

signals in the distinct band in lane 1 reveals the functional properties of the encapsulated molecule. Although PAGE results cannot directly confirm whether the functionalities were located inside the nanocage, results based on computer modeling and fluorescence functional assays are a strong indication of the encapsulation mechanism. Utilizing the programmability of RNA D and d' strands as well as modularity of the ssDNA-drug conjugates we were able to demonstrate feasibility of the encapsulation approach, in addition to RNA MGA aptamer encapsulation, for caging of small molecules.

Varying RNA Chemical Modifications Allows Control Over Nanoprism Serum Stability and Drug Release One potential advantage of RNA 3D nanocontainers is the ability to safely deliver and release encapsulated drugs in a fine-tunable fashion. Development of controlled release is extremely challenging yet highly desirable in RNA nanotechnology [1]. To release the encapsulated drug(s), one approach is to use the help of naturally occurring nucleases to break down RNA 3D nanoscaffold. It was the hypothesis that changing the percentage of 2-'F nucleotides in the nanoprism scaffold would result in diverse degradation profiles. To change the amount of 2'-F nucleotides in the nanoprisms, the ratio of 2'-F cytidine phosphate (CTP) and uridine phosphate (UTP) nucleotides to unmodified cytidine phosphate uridine phosphate were adjusted during in vitro transcription reactions to 4:0, 3:1, 2:2, 1:3, and 0:4, respectively. After transcription and purification, five different nanoprisms were assembled with 2'-F-C/U modifications of approximately 100%, 75%, 50%, 25%, and 0%. The degradation profiles of each nanoprism were observed over the course of one hour in 2% fetal bovine serum (FBS) solution at a final concentration of 200 nM and analyzed on 3% agarose gel (FIG. 4A). Gel band intensity was integrated using ImageJ software and intensity at each time point was compared to initial gel band intensity for each individual nanoprism (FIG. 4B). As shown by the time course plot, decreasing the percentage of 2'-F nucleotides increases the digestion rate of the nanoprism scaffold. This approach shows feasibility of controlled drug release by degradation of the partially 2'-F modified nano-container, which can be fine-tuned to the scale of minutes.

In Vitro Cell Binding Studies Revealed High Binding Affinity to Cancer Cells by RNA Nanocage Carrying ssDNA-Cy5.

The ability of the RNA nano-container to successfully bind and deliver drugs or reporter molecules into cancer cells would tremendously benefit the advancement of nanomedicine. To investigate whether the RNA nanocage can serve as a container to deliver small molecules, the 2'-F RNA frame structure was decorated with 5 copies of DNA oligonucleotide-folate conjugates and 1 copy of DNA-Cy5, as shown in FIG. 5A. Folate-containing nanoconstructs are known to have a strong affinity to cancer cells of epithelial origin as these types of cancer cells overexpress folate-binding protein receptors [46]. After incubation of the folate functionalized RNA nanoprism with KB cells, strong binding of the RNA complex with the cells was observed (FIG. 5A) in comparison to control complex having the same RNA 3D nanostructure but lacking folate molecules. This result demonstrates applicability of the 3D RNA system for detection and delivery of the reporter molecules.

The 3D RNA Triangular Nanoprism Possess Elevated Immunostimulatory Activity In Vitro.

CpG oligodeoxynucleotide (ODN) is a short synthetic DNA sequence containing unmethylated C and G nucleotides that has recently gained attention in immunology as it has shown to be useful as a vaccine adjuvant or immunotherapy reagent[37,47,48]. It was of particular importance to further investigate whether the unique 3D conformation of the RNA triangular nanoprism can be used to enhance the immunomodulation effect in vitro. Six CpG oligonucleotides were incorporated onto the 2'-F-RNA frame construct. The immunostimulatory efficacy of the nanoprism was evaluated by measuring the release of cytokines TNF-α after addition to mouse macrophage-like RAW264.7 cells (FIG. 5B), as previously described [49,50]. The results demonstrate that upon increasing the number of CpG induced a stronger immune response, observed by measuring the level of the induction of TNF-α. The results suggest that the cytokine released by the CpG prism complex significantly increases the immunostimulatory activity compared to CpG alone (FIG. 5B). Interestingly, the same observation was obtained by previous studies using RNA polygonal nanoconstructs [37], as with more CpG per nanoparticle a higher level of host immune response can be triggered. This data combined with cell binding studies demonstrates that the 3D RNA nanoprism can be readily utilized in cell studies to effectively carry functional moieties. T Experimental Section RNA Sequence Design and 3D Modeling RNA sequences were optimized using RNA 2D folding software Mfold prior to synthesis. Computer models of the RNA prism were assembled from two previously constructed RNA triangles [12]. The vertices of the triangles were assembled by overlapping helical domains of the triangular "arms" to position them at the correct angle and distance using the 'autofit' tool in Swiss-PDB Viewer (www.spdbv.vital-it.ch) and manual adjustment. The detailed procedure for the triangle design can be found in our previous reports [12]. Each triangle vertex contains a 21 nt ssRNA tethered to the 3'-end using a poly-uracil (poly-U) linker. The poly-U is inserted to provide a hinge allowing for the flexibility of the ssRNA when hybridized with its complementary sequence of another triangle. The resulting 21 bp RNA duplexes were chosen to have similar lowest free-energy secondary structures (calculated $\Delta G=-39.0\pm2.0$ kcal/mol). The sequence of the RNA MGA module was extracted from the PDB databank (www.pdb.org), PDB ID: 1F1T [24].

RNA Synthesis, Purification and Assembly

Templates for RNA transcription were prepared by standard protocols described in detail elsewhere[51]. Briefly, PCR was used to prepare transcription templates using PCR reaction kit (Promega Corporation, GoTaq® FlexiDNA Polymerase) for the amplification of DNA primers (IDT). Following purification of DNA templates on spin columns (QIAGEN), the RNA strands or 2'-F-U/C modified RNA strands were transcribed using home-made T7 RNA polymerase. The RNA was precipitated with cold ethanol, then the pellets dried and resuspended in ddH$_2$O. Homogeneity of individual RNA strands is checked by denaturing 10% PAGE. For assembly assays, equimolar RNA strands (0.5 μM each) were mixed in 1×TMS (40 mM TRIS-HCl pH=8.0, 100 mM NaCl and 10 mM MgCl2) buffer. The RNA mixture was heated to 80° C. for 5 min and slowly cooled to 4° C. at the rate of 2° C./min in a PCR thermocycler. RNA assembly products were checked on native 6% or 7% PAGE (29:1 acrylamide: bis-acrylamide ratio) in 1×TBM (89 mM TRIS-Borate pH=8.0, 5 mM MgCl$_2$) running buffer. All native PAGE experiments were run at 4° C. at constant 90 V for 2 hours. Gels were stained in Ethidium Bromide buffer for total RNA strand visualization or in MG binding buffer (20 μM MG dye, 10 mM HEPES pH=7.4, 100 mM KCl, 5 mM $MgCl_2$) for detection of MG aptamer signal as previously reported[37].

Cryo-Electron Microscopy

2 µl of RNA triangular prism nanoparticle solution (1 mg/ml) was applied onto a glow-discharged 200-mesh R1.2/1.3 Quantifoil grid. The grids were blotted for 3 s and rapidly frozen in liquid ethane using a Vitrobot Mark IV (FEI). Then the girds were transferred to JEM2200FS cryo-electron microscope (JEOL) operated at 200 kV with incolumn filter for screening. Micrographs of 10 nm RNA prism were recorded with a direct detection device (DDD) (DE-20 4 k×5 k camera, Direct Electron, LP) operating in movie mode at a recording rate of 25 raw frames per second at 25,000× microscope magnification (corresponding to a calibrated sampling of 2.51 Å per pixel) and a dose rate of ~20 electrons per second per Å2 with a total exposure time of 3 s. Micrographs of 5 nm RNA prism were recorded with a 4 k×4 k CCD (Gatan) at 80,000× microscope magnification (corresponding to a calibrated sampling of 1.36 Å per pixel) and a dose rate of ~20 electrons per second per Å2 with a total exposure time of 3 s. A total 52 images of 10 nm RNA prism and 30 images of 5 nm RNA prism were collected with a defocus range of 2-4 µM.

Single Particle Image Processing and 3D Reconstruction

The image processing software package EMAN2 was used for the micrograph evaluation, particle picking, CTF correction, 2-D reference-free class averaging, initial model building and 3-D refinement of the cryo-electron microscopy data. We boxed total 2340 particles for 10 nm RNA prism and 2206 particles for 5 nm RNA prism to generate the 2D class averages for building the initial models. Finally, 1514 particles for the 10 nm RNA prism and 1648 particles for the 5 nm RNA prism were used for final refinement, applying the D3 symmetry. The resolution for the final maps was estimated by the 0.143 criterion of FSC curve without any mask. 25 Å and 22 Å Gauss low-pass filter were applied to the final 3D maps displayed in the Chimera software package.

AFM Images

For all samples, specially modified mica surfaces (APS mica) were used. The APS mica was obtained by incubation of freshly cleaved mica in 167 nM 1-(3-aminopropyl) silatrane following previously reported protocol [52]. The RNA samples were diluted with 1×TMS buffer to a final concentration of 3-5 nM. Then, 5-10 µL was immediately deposited on APS mica. After 2 min incubation on the surface, excess samples were washed with DEPC treated water and dried under a flow of Argon gas. AFM images in air were acquired using MultiMode AFM NanoScope IV system (Veeco/Digital Instruments, Santa Barbara, Calif.) operating in tapping mode. Two types of AFM probes were used for tapping mode imaging in air: (1) regular tapping Mode Silicon Probes (Olympus from Asylum Research, Santa Barbara, Calif.) with a spring constant of about 42 N/m and a resonant frequency between 300 and 320 kHz. (2) Non-contact NSG01 DLC probes (K-Tek Nanotechnology, Wilsonville, Oreg.) with a spring constant of about 5.5 N/m and a resonance frequency between 120 and 150 kHz.

Dynamic Light Scattering

The hydrodynamic diameter of the RNA nanoprisms was determined at a concentration of 10 µM in 50 µL TMS buffer using a Zetasizer nano-ZS (Malvern Instrument, LTD) at 25° C.

Prism_MG Degradation Assay

The function of the MGA within the triangular prism nanoparticles was assayed by mixing the RNA complex at a concentration of 0.1 µM with 1 µM MG dye in 1×TMS buffer. The solutions were allowed to equilibrate at room temperature for 10 minutes. The fluorescence emission spectrum (recorded from 630-750 nm) of the complexes was measured using a fluorospectrophotometer (Horiba Jobin Yvon) with an excitation wavelength positioned at 615 nm. 1 µL of 500 U/µL RNase T1 (Thermo Scientific) was added to 99 µL of the above RNA-MG complex directly in a fluorometer cuvette. Fluorescence at λmax=650 nm was immediately recorded and monitored every 1 sec for a total time of 3600 sec. The time resolved fluorescence life time measurements were performed by the software integrated within the fluorometer. The obtained data were fit using exponential decay function $I(t)=I_0 e^{(-t/\tau)}$, where $I_0$ is the initial intensity (at time zero) and T is the mean life time defined as the time for the intensity to drop by 1/e or to ~37%. All fluorescence decay experiments were conducted in triplicate with indication off for mean standard error (SEM).

In Vitro Binding and Entry of RNA Nanoparticles into Targeted Cells.

KB cells (ATCC) were seeded at $1×10^4$ cells per well into chambered glass coverslips in folate free 1640 medium overnight and treated with 200 nM Cy5 labeled RNA nanoprism complex in the same medium: The samples included: RNA nanoprism carrying 5 DNA-folate conjugates, ii) control RNA nanoprism carrying DNA without folate, and iii) cell only at 37° C. for 4 h followed by washing with pre-cooled PBS. The cells were then fixed with 4% paraformaldehyde for 20 min and incubated with DAPI (Invitrogen) for 24h at room temperature. The cells were then assayed for binding and cell entry using an Olympus FV1000 Confocal Microscope.

Cytokine Secretion from RAW264.7 Cells.

RAW 264.7 cells were cultured overnight in 24-well plates with a cell density of $2.5×10^5$ cells per well. RNA nanoprisms harboring different numbers of CpG ODNs were diluted in Opti-MEM medium (Life Technologies Corporation, Carlsbad, Calif.) and incubated with the cells. The cells containing RNA complex were continually cultured for 8 h at 37° C. in humidified air containing 5% $CO_2$. After the incubation period, the cell culture supernatant was collected and stored at −80° C. until use. The concentration of TNF-α in the supernatant was determined by enzyme-linked immunosorbent assay (ELISA) using Mouse ELISA MAX™ Deluxe sets (BioLegend, Inc., San Diego, Calif.), following protocols provided by the manufacturer.

REFERENCES

[1] P. Guo, Nature Nanotechnology, 2010, 5, 833.
[2] A. Chworos, I. Severcan, A. Y. Koyfman, P. Weinkam, E. Oroudjev, H. G. Hansma, and L. Jaeger, Science, 2004, 306, 2068.
[3] D. Shu, Y. Shu, F. Hague, S. Abdelmawla, and P. Guo, Nature Nanotechnology, 2011, 6, 658.
[4] E. Bindewald, R. Hayes, Y. G. Yingling, W. Kasprzak, and B. A. Shapiro, Nucleic Acids Res., 2008, 36, D392-D397.
[5] N. B. Leontis and E. Westhof, R N A., 2001, 7, 499.
[6] C. Chen, C. Zhang, and P. Guo, R N A, 1999, 5, 805.
[7] Nagarajan Pattabiraman, Hugo M. Martinez, and Bruce A. Shapiro, Journal of Bimolecular Structure & Dynamics, 2002, 20, 397.
[8] P. Guo, C. Zhang, C. Chen, M. Trottier, and K. Garver, Mol. Cell., 1998, 2, 149.
[9] C. Chen, S. Sheng, Z. Shao, and P. Guo, J Biol Chem, 2000, 275(23), 17510.

[10] L. Jaeger and N. B. Leontis, Angew. Chem Int. Ed Engl., 2000, 39, 2521.
[11] E. Westhof, B. Masquida, and L. Jaeger, Folding & Design, 1996, 1, R78-R88.
[12] E. F. Khisamutdinov, D. L. Jasinski, and P. Guo, ACS Nano., 2014, 8, 4771.
[13] D. Shu, W. D. Moll, Z. Deng, C. Mao, and P. Guo, Nano Lett., 2004, 4, 1717.
[14] H. Li, T. Lee, T. Dziubla, F. Pi, S. Guo, J. Xu, C. Li, F. Hague, X. Liang, and P. Guo, Nano Today, 2015, 10, 631.
[15] I. Severcan, C. Geary, A. Chworos, N. Voss, E. Jacovetty, and L. Jaeger, Nat. Chem., 2010, 2, 772.
[16] K. A. Afonin, E. Bindewald, A. J. Yaghoubian, N. Voss, E. Jacovetty, B. A. Shapiro, and L. Jaeger, Nat. Nanotechnol., 2010, 5, 676.
[17] C. Hao, X. Li, C. Tian, W. Jiang, G. Wang, and C. Mao, Nat. Commun., 2014, 5, 3890.
[18] J. W. Yu, Z. Y. Liu, W. Jiang, G. S. Wang, and C. D. Mao, Nature Communications, 2015, 6, 5724.
[19] C. M. Erben, R. P. Goodman, and A. J. Turberfield, Angewandte Chemie-International Edition, 2006, 45, 7414.
[20] S. Juul, F. Iacovelli, M. Falconi, S. L. Kragh, B. Christensen, R. Frohlich, O. Franch, E. L. Kristoffersen, M. Stougaard, K. W. Leong, Y. P. Ho, E. S. Sorensen, V. Birkedal, A. Desideri, and B. R. Knudsen, ACS Nano, 2013, 7, 9724.
[21] P. K. Lo, P. Karam, F. A. Aldaye, C. K. McLaughlin, G. D. Hamblin, G. Cosa, and H. F. Sleiman, Nature Chemistry, 2010, 2, 319.
[22] C. Zhang, X. Li, C. Tian, G. M. Yu, Y. L. Li, W. Jiang, and C. D. Mao, ACS Nano, 2014, 8, 1130.
[23] T. G. W. Edwardson, K. M. M. Carneiro, C. K. McLaughlin, C. J. Serpell, and H. F. Sleiman, Nature Chemistry, 2013, 5, 868.
[24] C. Baugh, D. Grate, and C. Wilson, J. Mol. Biol., 2000, 301, 117.
[25] D. H. Nguyen, S. C. Defina, W. H. Fink, and T. Dieckmann, J. Am. Chem. Soc., 2002, 124, 15081.
[26] R. Reif, F. Hague, and P. Guo, Nucleic Acid Ther., 2013, 22(6), 428.
[27] F. Hague, D. Shu, Y. Shu, L. Shlyakhtenko, P. Rychahou, M. Evers, and P. Guo, Nano Today, 2012, 7, 245.
[28] W. W. Grabow, P. Zakrevsky, K. A. Afonin, A. Chworos, B. A. Shapiro, and L. Jaeger, Nano Lett., 2011, 11, 878.
[29] W. Xu and Y. Lu, Anal. Chem., 2010, 82, 574.
[30] Y. Shu, D. Shu, Z. Diao, G. Shen, and P. Guo, IEEE/NIH Life Science Systems and Applications Workshop, 2009, 9.
[31] H. Zhang, J. A. Endrizzi, Y. Shu, F. Hague, C. Sauter, L. S. Shlyakhtenko, Y. Lyubchenko, P. Guo, and Y. I. Chi, R N A, 2013, 19, 1226.
[32] F. Hague, S. Wang, C. Stites, L. Chen, C. Wang, and P. Guo, Biomaterials, 2015, 53, 744.
[33] Y. Shu, M. Cinier, S. R. Fox, N. Ben-Johnathan, and P. Guo, Molecular Therapy, 2011, 19, 1304.
[34] N. Guex and M. C. Peitsch, Electrophoresis, 1997, 18, 2714.
[35] R. Veneziano, S. Ratanalert, K. Zhang, F. Zhang, H. Yan, W. Chiu, and M. Bathe, Science, 2016, 352, 1534.
[36] Y. Shu, F. Hague, D. Shu, W. Li, Z. Zhu, M. Kotb, Y. Lyubchenko, and P. Guo, RNA, 2013, 19, 766.
[37] E. Khisamutdinov, H. Li, D. Jasinski, J. Chen, J. Fu, and P. Guo, Nucleic Acids Res., 2014, 42, 9996.
[38] D. Shu, E. Khisamutdinov, L. Zhang, and P. Guo, Nucleic Acids Res., 2013, 42, e10.
[39] D. M. Kolpashchikov, J. Am. Chem. Soc., 2005, 127, 12442.
[40] J. R. Babendure, S. R. Adams, and R. Y. Tsien, J. Am. Chem. Soc., 2003, 125, 14716.
[41] D. Jasinski, E. F. Khisamutdinov, Y. L. Lyubchenko, and P. Guo, ACS Nano, 2014, 8, 7620.
[42] M. Ikehara, E. Ohtsuka, T. Tokunaga, S. Nishikawa, S. Uesugi, T. Tanaka, Y. Aoyama, S. Kikyodani, K. Fujimoto, K. Yanase, K. Fuchimura, and H. Morioka, Proceedings of the National Academy of Sciences of the United States of America, 1986, 83, 4695.
[43] S. Pfeiffer, Y. KarimiNejad, and H. Ruterjans, J Mol Biol, 1997, 266, 400.
[44] H. Li, K. Zhang, F. Pi, S. Guo, L. Shlyakhtenko, W. Chiu, D. Shu, and P. Guo, Adv. Mater., 2016, Accepted. In press.
[45] N. M. Green and E. J. Toms, Biochem. J., 1973, 133, 687.
[46] C. P. Leamon and P. S. Low, Drug Discovery Today, 2001, 6, 44.
[47] G. Hartmann, R. D. Weeratna, Z. K. Ballas, P. Payette, S. Blackwell, I. Suparto, W. L. Rasmussen, M. Waldschmidt, D. Sajuthi, R. H. Purcell, H. L. Davis, and A. M. Krieg, J. Immunol, 2000, 164, 1617.
[48] G. J. Weiner, H. M. Liu, J. E. Wooldridge, C. E. Dahle, and A. M. Krieg, Proceedings of the National Academy of Sciences of the United States of America, 1997, 94, 10833.
[49] P. M. Winter, A. M. Morawski, S. D. Caruthers, R. W. Fuhrhop, H. Zhang, T. A. Williams, J. S. Allen, E. K. Lacy, J. D. Robertson, G. M. Lanza, and S. A. Wickline, Circulation, 2003, 108, 2270.
[50] E. K. Lim, B. Kim, Y. Choi, Y. Ro, E. J. Cho, J. H. Lee, S. H. Ryu, J. S. Suh, S. Haam, and Y. M. Huh, J Biomed. Mater. Res A, 2013, 102(1), 49.
[51] Y. Shu, D. Shu, F. Hague, and P. Guo, Nat Protoc., 2013, 8, 1635.
[52] Y. L. Lyubchenko, A. A. Gall, L. S. Shlyakhtenko, R. E. Harrington, B. L. Jacobs, P. I. Oden, and S. M. Lindsay, J Biomol Struct Dyn, 1992, 10, 589

Example 3: Construct Programmable 3D RNA Nanocages to Deliver High Doses of Multiple Chemotherapeutics Drugs Specifically to the Tumor Micro-Environment Several passive targeting lipid and polymer nanoparticles have been pursued for encapsulating chemotherapeutic payloads[1-3]. Two are FDA approved (Abraxane4 and Doxil5), and a few are in clinical trials[6-9]. DNA 3D polygons have been built using organic linkers[10-13] and origami method [14,15] to encapsulate proteins and functional molecules16-20. RNA cages have also been reported[21,22].

Many drugs do not reach the tumors, are rapidly cleared from blood and exhibit significant side effects by accumulating in healthy organs. Lipid/polymer nanoparticles can increase the circulation time, improved PK/PD and tumor retention, and reduced side effects[23,24]. However, challenges remain[23,24]: (1) Lack of targeting modules for enhancing intracellular delivery and targeting stem cell populations[25-28]. (2) Particle heterogeneity and aggregation. (3) DNA origami using kilobase long ssDNA as scaffold with short staple strands are relatively large (>100 nm), which increases risks of being engulfed by Kupffer cells and macrophages. (4) Require tedious multi-step drug loading.

The 3WJ can serve as building blocks to construct ultrastable 3D nanocages with precise control of size, shape and stoichiometry[29-31] (FIG. 11). RNA nanocage assembly is stabilized by canonical and non-canonical base paring, or base stacking and tertiary interactions[32]. RNA nanocages can be readily functionalized with targeting aptamers as ligands or conjugated with pro-drugs into certain portion of the RNA building block that can be placed within the nanocage or be used as the frame. Due to high affinity of the three fragments in 3WJ assembly and the unusually high thermostability, presence of certain targeting and therapeutic cargoes will not disrupt the folding property of the container [33-35]. RNA nanocages can assemble in organic or aqueous solvent without changing intrinsic drug properties. RNA nanocages (20-50 nm) will reach tumor vasculature via EPR effects and remain in tumor microenvironment with minimal non-specific accumulation in healthy organs, similar to our other RNA architectures of size<50 nm.33,36-42. By adjusting the ratio of the stable (2'-F U and C) and unstable (normal) nucleotides, timely controlled drug release is possible.

Lung cancer by far has the highest incidence and mortality[43]. Non-small Cell Lung Cancer (NSCLC) accounts for >85% of all cases with a dismal 5-year survival rate[43]. Research on NSCLC has made progress, but its response rate and survival improvement have been slow and improvements are needed[44].

Construction and Functionalization of 3D RNA Nanocages

A computational strategy was developed to engineer programmable 3D RNA nanocages (FIG. 11) (prisms, tetrahedrons, cubes, and dodecahedrons). The precise control of polygon size and shape was demonstrated by tuning the 3WJ angle[29]. RNA nanocages use rigid double helices to serve as edges connected by elastic pRNA-3WJ at each vertices. The size of the nanocages can be easily controlled (20-50 nm) by varying the length of the edge sequences. The entire complex self-assembles from a set of rationally designed RNA strands in one step with very high yield. The 3WJ motif at the vertices can harbor targeting modules without disrupting nanocage assembly.

Imaging markers: One strand is end-labeled with Alexa647, as described previously[33,36,37]. Upon mixing the labeled with other strands in equimolar ratio, the nanocage will assemble efficiently (FIG. 11).

Figure 12A:
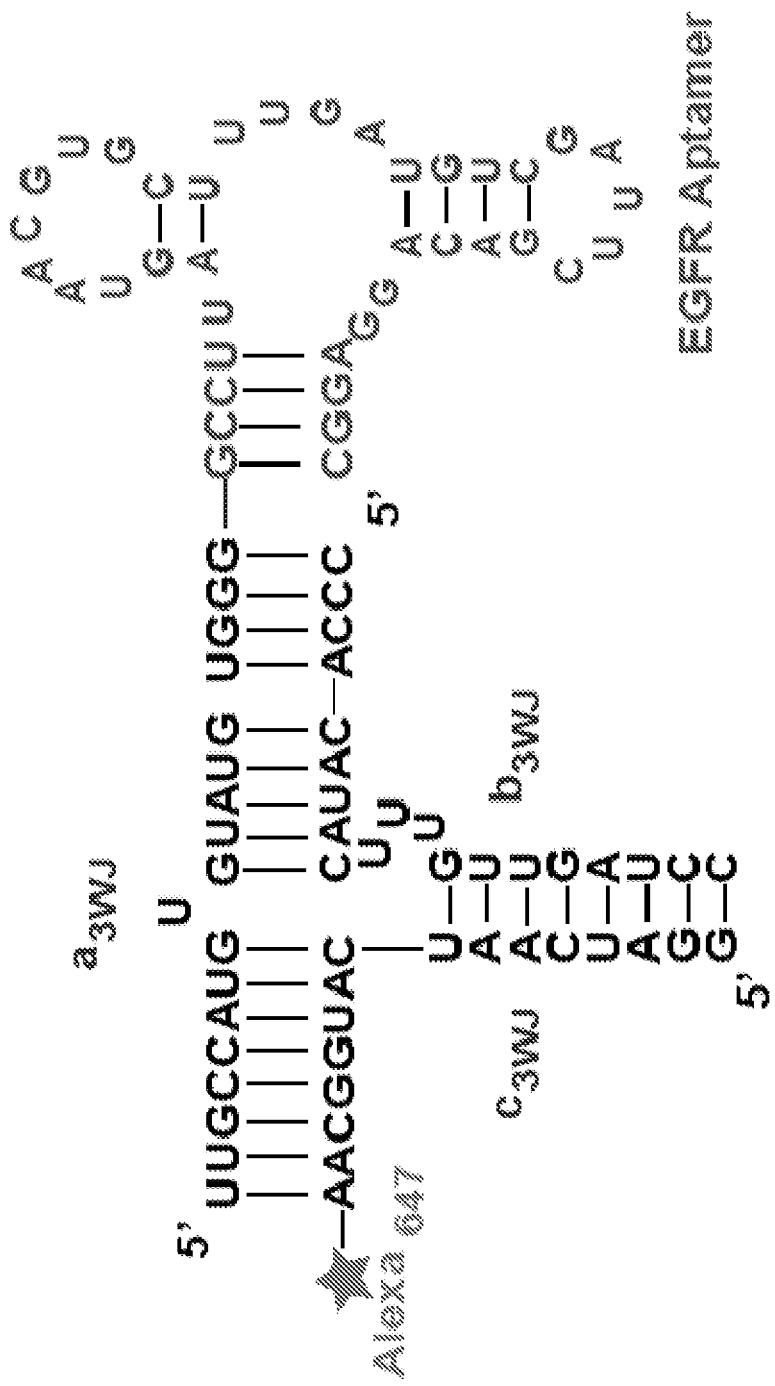
FIGS. 12A-12B show (FIG. 12A) construction of pRNA-3WJ_EGFR-aptamer nanoparticles and (FIG. 12B) a panel of confocal images showing specific binding and entry into A549 lung cancer cells. a3WJ/EGFR aptamer (SEQ ID NO:6); b3WJ (SEQ ID NO:7); c3WJ (SEQ ID NO:8).
Figure 12B:
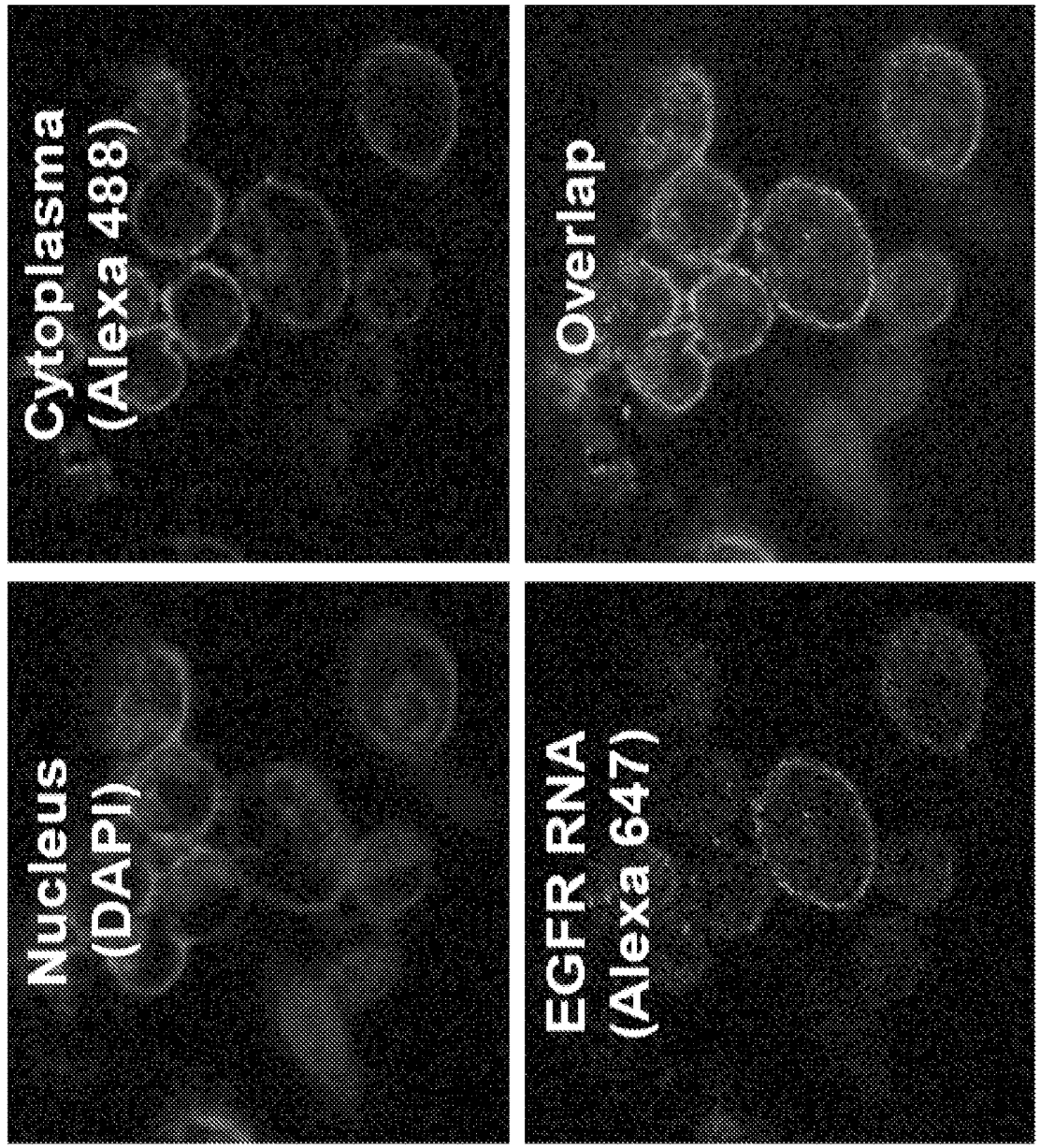

Targeting RNA aptamers: EGFR (HER1/ErbB1) receptors are highly prevalent in both primary tumors and metastatic NSCLC, making them attractive for targeted therapies [83-85]. RNA aptamers[86-89] targeting EFFR receptors have been used resulting in strong binding to lung cancer cells in vitro (FIG. 12) and breast cancer cells in vivo. The RNA nanocages are evaluated with lung tumor derived cell lines (ex. HCC4017, H2087, A549, HCC15). The goal is to use aptamers for internalizing RNA constructs into NSCLC cells via receptor-mediated endocytosis, instead of inhibiting the EGFR signaling pathway, which have been clinically disappointing[90,91].

Figure 13A:
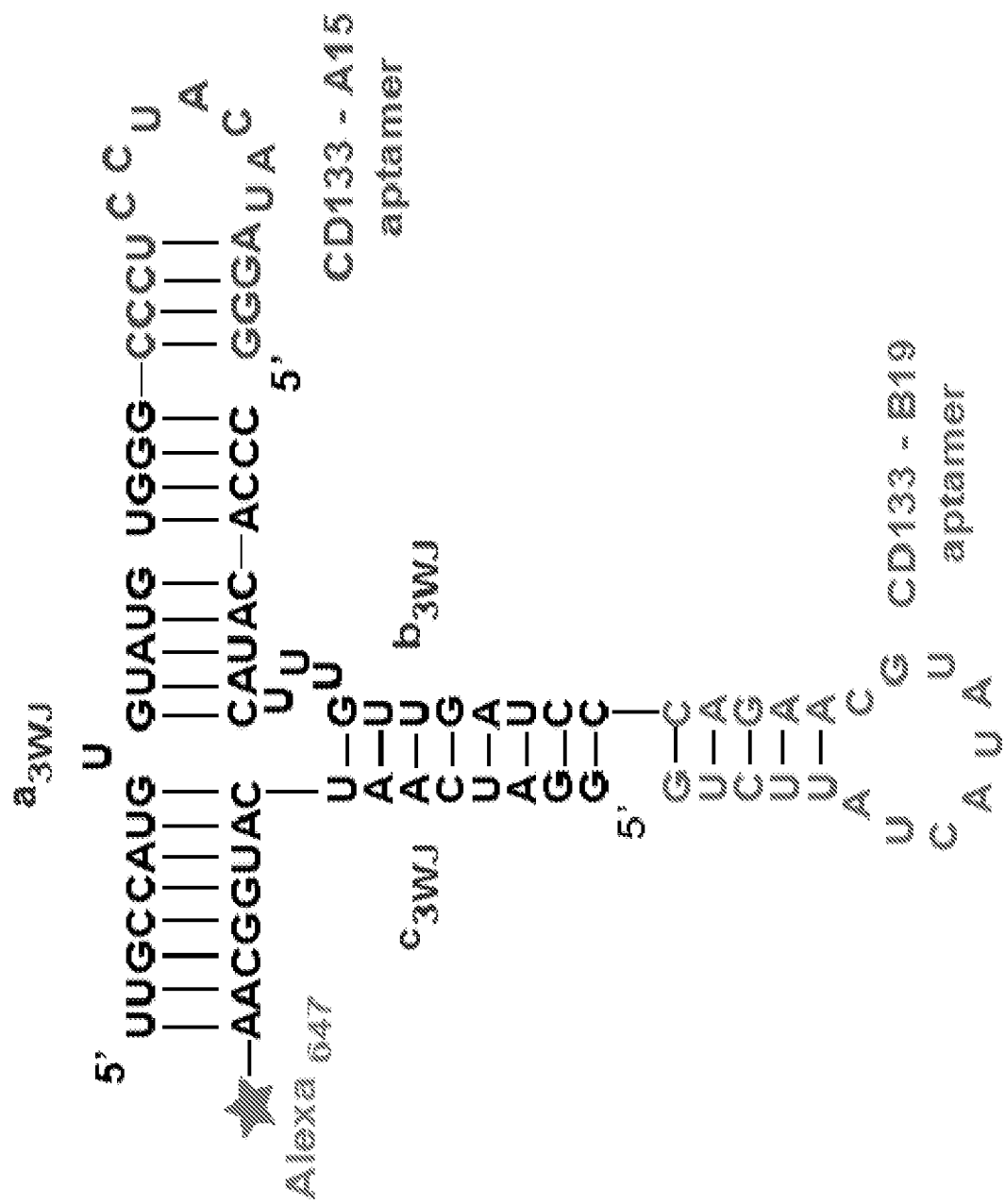
FIGS. 13A-13B show (FIG. 13A) construction of bivalent pRNA-3WJ_CD133-aptamer nanoparticles and (FIG. 13B) a panel of confocal images showing specific binding and entry into breast cancer stem cells. a3WJ/CD133 aptamer (SEQ ID NO:9); b3WJ/CD133 aptamer (SEQ ID NO:10); c3WJ (SEQ ID NO:8).
Figure 13B:
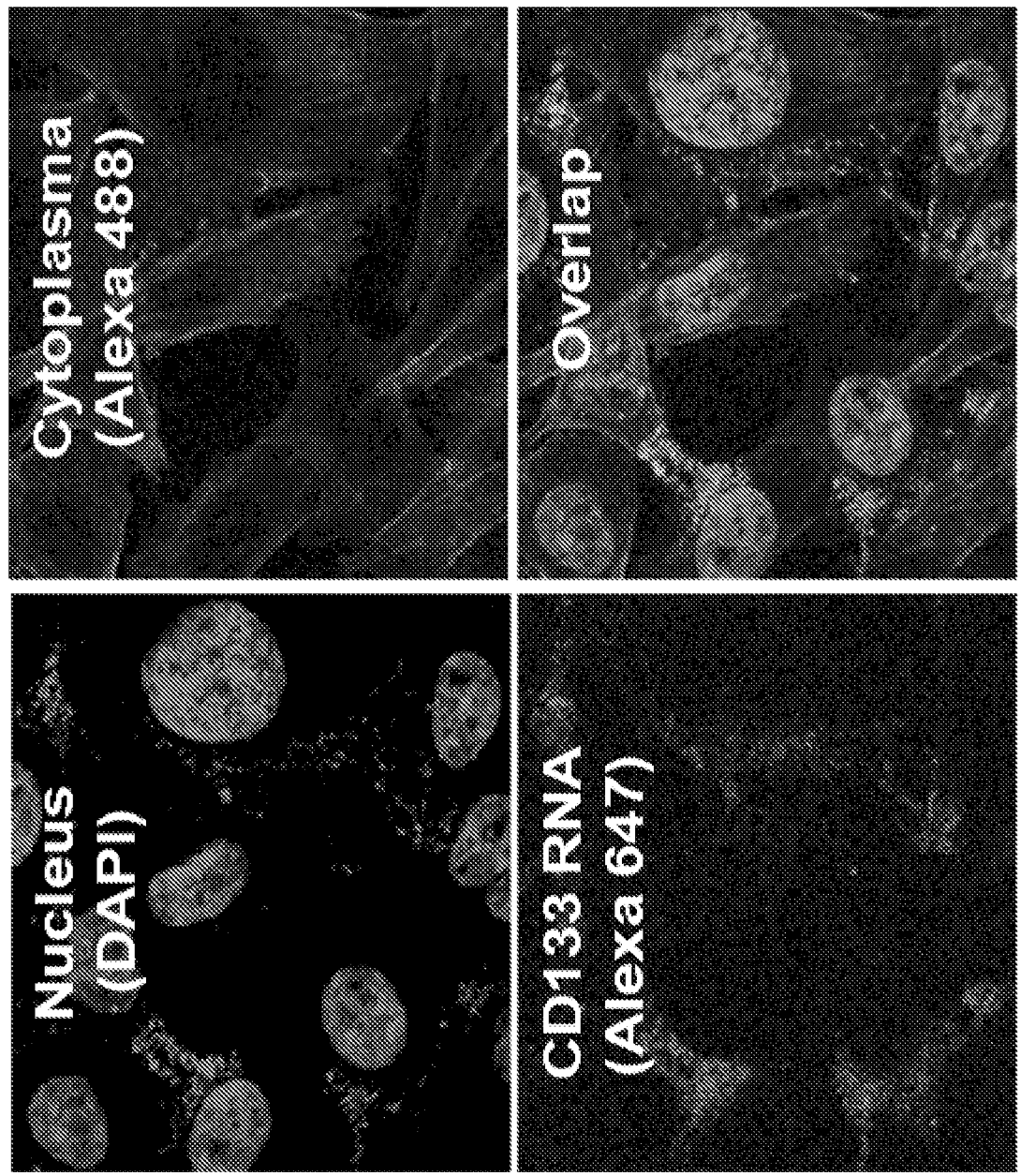

Target NSCLC stem cells: Rare stem cells present within the bulk cancer cells play a major role in cancer initiation, progression, resistance, and recurrence[92,93]. There is specific binding and entry of CD133 targeting RNA aptamers [94] into breast cancer stem cells (FIG. 13). CD133 is attractive for targeting NSCLC stem cells, since they are upregulated under hypoxic conditions; resistant to radiation due to activation of DNA damage proteins; and resistant to chemotherapy due to increased Akt/PKB and Bcl-2 cell survival response[95].

Alternative approaches: (1) 2'-F bivalent Y-RNA NP to target EpCAM receptors highly expressed on primary and metastatic NSCLC cells, including stem cells[84,96]; (2) Folate to target folate receptors overexpressed in epithelial solid NSCLC tumors. Multiple folates are used to significantly enhance in vivo binding avidity and therapeutic delivery efficacy, as shown by dendrimers[97].

Encapsulation of chemotherapeutic drugs: several clinically approved NSCLC drugs, such as (1) Methotrexate (anti-metabolite)[98,99]; (2) Paclitaxel (mitotic inhibitor) [100-102]; (3) Cisplatin (alkylating agent)[103,104]; (4) Crizotinib (kinase inhibitor)[104,105]; and (5) Topotecan (topoisomerase inhibitor)[106,107] are encapsulate. Given the heterogeneity of NSCLC, drug combinations are used to target multiple pathways simultaneously.

RNA molecules are stable in both aqueous and organic solvents, and therefore suitable for encapsulating even poorly soluble drugs. Drugs are simply mixed in the annealing buffer (aqueous or organic solvent) during RNA nanocage assembly process. As the nanocages assemble, drugs are encapsulated in one step. The procedure is simple and highly efficient compared to traditional lipid/polymer drug loading techniques[108]. To demonstrate encapsulation, ~1 nm nanogold (Nanoprobes) are used and then the RNA nanocages are imaged by TEM. Spectroscopic and kinetic studies[18] are carried out to quantitatively evaluate the release of the nanogolds from the RNA nanocages. The approach is to vary the number and location of 2'-F nucleotides in the RNA sequences and trigger drug release upon degradation (12-36 hr time frame) of the RNA cages. For evaluating the release of encapsulated drugs, an isocratic HPLC assay[109] is developed and other methods used, such as continuous flow and dialysis commonly used for polymer and lipid nanoparticles[108].

As an alternative, acid-labile bond and 'click-chemistry' approach is used to conjugate pro-drugs at certain locations of the RNA building block which can be placed within the nanocage or be used as the frame, so leakiness of the cage, if any, is not an issue.

In Vivo Evaluation of RNA Nanocages Harboring RNA Aptamer and Chemotherapeutic Drug Three NSCLC mouse models[53,110-113] are evaluated using clinically relevant patient derived samples (available at University of Kentucky Markey Cancer Center): (1) subcutaneous xenografts; (2) orthotopic xenografts (via intra-thoracic injection); and (3) spontaneous (from orthotropic tumors) and experimental (via intravenous injection) metastasis. Lung cancer metastasizes in the bone, brain, liver, and lungs; all of which can be targeted using RNA nanoparticles. Since bone metastasis is challenging to model in vivo 1[14], periosteal injection of tumor cells directly adjacent to a long bone[115,116] (FIG. 6G) is examined. RNA nanocages encapsulating single or multiple drugs are systemically injected and assays are conducted for tumor cytotoxic effects along with evaluation of pharmacological and toxicity profiles with controls.

Approaches are also developed for spatiotemporal release of encapsulated drugs by opening the RNA nanocages in response to endogenous signals, such as after aptamer-receptor binding or in response to tumor hypoxic conditions.

REFERENCES

1. Rivera E. Liposomal anthracyclines in metastatic breast cancer: clinical update. Oncologist. 2003; 8 Suppl 2:3-9
2. Duncan R. The dawning era of polymer therapeutics. Nat Rev. Drug Discov. 2003 May; 2(5):347-60
3. Green J J, Chiu E, Leshchiner E S, Shi J, Langer R, Anderson D G. Electrostatic ligand coatings of nanoparticles enable ligand-specific gene delivery to human primary cells. Nano Lett. 2007 April; 7(4):874-9
4. Gradishar W J. Albumin-bound paclitaxel: a next-generation taxane. Expert Opin. Pharmacother. 2006 June; 7(8):1041-53
5. Barenholz Y. Doxil®—the first FDA-approved nanodrug: lessons learned. J Control Release 2012 Jun. 10; 160(2):117-34
6. Babu A, Templeton A K, Munshi A, Ramesh R. Nanodrug Delivery Systems: A Promising Technology for Detection, Diagnosis, and Treatment of Cancer. AAPS. PharmSciTech. 2014 June; 15(3):709-21
7. Batist G, Barton J, Chaikin P, Swenson C, Welles L. Myocet (liposome-encapsulated doxorubicin citrate): a new approach in breast cancer therapy. Expert Opin.Pharmacother. 2002 December; 3(12):1739-51
8. Andreopoulou E, Gaiotti D, Kim E, Downey A, Mirchandani D, Hamilton A, Jacobs A, Curtin J, Muggia F. Pegylated liposomal doxorubicin HCL (PLD; Caelyx/Doxil): experience with long-term maintenance in responding patients with recurrent epithelial ovarian cancer. Ann.Oncol. 2007 April; 18(4):716-21
9. Harries M, Ellis P, Harper P. Nanoparticle albumin-bound paclitaxel for metastatic breast cancer. Journal of Clinical Oncology 2005 Nov. 1; 23(31):7768-71
10. Aldaye F A, Palmer A L, Sleiman H F. Assembling materials with DNA as the guide. Science 2008; 321:1795-9
11. Lo P K, Metera K L, Sleiman H F. Self-assembly of three-dimensional DNA nanostructures and potential biological applications. Current Opinion in Chemical Biology 2010 October; 14(5):597-607
12. McLaughlin C K, Hamblin G D, Aldaye F A, Yang H, Sleiman H F. A facile, modular and high yield method to assemble three-dimensional DNA structures. Chemical Communications 2011; 47(31):8925-7
13. Yang H, Metera K L, Sleiman H F. DNA modified with metal complexes: Applications in the construction of higher order metal-DNA nanostructures. Coordination Chemistry Reviews 2010 October; 254(19-20):2403-15
14. Andersen E S, Dong M, Nielsen M M, Jahn K, Subramani R, Mamdouh W, Golas M M, Sander B, Stark H, Oliveira C L, et al. Self-assembly of a nanoscale DNA box with a controllable lid. Nature 2009 May 7; 459(7243):73-6
15. Douglas S M, Dietz H, Liedl T, Hogberg B, Graf F, Shih W M. Self-assembly of DNA into nanoscale three-dimensional shapes. Nature 2009 May 21; 459(7245):414-8
16. Erben C M, Goodman R P, Turberfield A J. Single-molecule protein encapsulation in a rigid DNA cage. Angewandte Chemie-International Edition 2006; 45(44):7414-7
17. Juul S, Iacovelli F, Falconi M, Kragh S L, Christensen B, Frohlich R, Franch O, Kristoffersen E L, Stougaard M, Leong K W, et al. Temperature-Controlled Encapsulation and Release of an Active Enzyme in the Cavity of a Self-Assembled DNA Nanocage. ACS Nano 2013 November; 7(11):9724-34
18. Lo P K, Karam P, Aldaye F A, McLaughlin C K, Hamblin G D, Cosa G, Sleiman H F. Loading and selective release of cargo in DNA nanotubes with longitudinal variation. Nature Chemistry 2010 April; 2(4):319-28
19. Banerjee A, Bhatia D, Saminathan A, Chakraborty S, Kar S, Krishnan Y. Controlled Release of Encapsulated Cargo from a DNA Icosahedron using a Chemical Trigger. Angewandte Chemie-International Edition 2013; 52(27):6854-7
20. Torelli E, Marini M, Palmano S, Piantanida L, Polano C, Scarpellini A, Lazzarino M, Firrao G. A DNA Origami Nanorobot Controlled by Nucleic Acid Hybridization. Small 2014 Jul. 23; 10(14):2918-26
21. Afonin K A, Bindewald E, Yaghoubian A J, Voss N, Jacovetty E, Shapiro B A, Jaeger L. In vitro assembly of cubic RNA-based scaffolds designed in silico. Nat. Nanotechnol. 2010 September; 5(9):676-82. PMCID: PMC2934861
22. Severcan I, Geary C, Chworos A, Voss N, Jacovetty E, Jaeger L. A polyhedron made of tRNAs. Nature Chemistry 2010 September; 2(9):772-9
23. Grodzinski P, Torchilin V, (Editors). Advanced Drug Delivery Reviews: Cancer Nanotechnology. Volume 66 ed. Elsevier; 2014.1-116 p.
24. Grodzinski P, Farrell D. Future opportunities in cancer nanotechnology—NCI strategic workshop report. Cancer Res. 2014 Mar. 1; 74(5):1307-10
25. Mamot C, Ritschard R, Kung W, Park J W, Herrmann R, Rochlitz C F. EGFR-targeted immunoliposomes derived from the monoclonal antibody EMD72000 mediate specific and efficient drug delivery to a variety of colorectal cancer cells. Journal of Drug Targeting 2006 May; 14(4):215-23
26. Mamot C, Drummond D C, Noble C O, Kallab V, Guo Z X, Hong K L, Kirpotin D B, Park J W. Epidermal growth factor receptor-targeted immunoliposomes significantly enhance the efficacy of multiple anticancer drugs in vivo. Cancer Research 2005 Dec. 15; 65(24):11631-8
27. Mamot C, Drummond D C, Greiser U, Hong K, Kirpotin D B, Marks J D, Park J W. Epidermal growth factor receptor (EGFR)-targeted immunoliposomes mediate specific and efficient drug delivery to EGFR- and EGFRvIII-overexpressing tumor cells. Cancer Research 2003 Jun. 15; 63(12):3154-61
28. Park J W, Hong K, Kirpotin D B, Colbern G, Shalaby R, Baselga J, Shao Y, Nielsen U B, Marks J D, Moore D, et al. Anti-HER2 Immunoliposomes: Enhanced Efficacy Attributable to Targeted Delivery. Clinical Cancer Research 2002 Apr. 1; 8(4):1172-81
29. Khisamutdinov E, Li H, Jasinski D, Chen J, Fu J, Guo P. Enhancing immunomodulation on innate immunity by shape transition among RNA triangle, square, and pentagon nanovehicles. Nucleic Acids Res. 2014; 42:9996-10004
30. Jasinski D, Khisamutdinov E F, Lyubchenko Y L, Guo P. Physicochemically Tunable Poly-Functionalized RNA Square Architecture with Fluorogenic and Ribozymatic Properties. ACS Nano 2014 Jun. 27; 8:7620-9
31. Khisamutdinov E F, Jasinski D L, Guo P. RNA as a boiling-resistant anionic polymer material to build robust structures with defined shape and stoichiometry. ACS Nano. 2014 Apr. 3; 8:4771-81. PMCID:PMC4046798
32. Guo P. The emerging field of RNA nanotechnology. Nature Nanotechnology 2010 December; 5(12):833-42. PMCID:PMC3149862
33. Shu D, Shu Y, Haque F, Abdelmawla S, Guo P. Thermodynamically stable RNA three-way junctions for constructing multifuntional nanoparticles for delivery of therapeutics. Nature Nanotechnology 2011; 6:658-67. PMCID:PMC3189281
34. Liu J, Guo S, Cinier M, Shlyakhtenko L S, Shu Y, Chen C, Shen G, Guo P. Fabrication of stable and RNase- 35. Shu D, Khisamutdinov E, Zhang L, Guo P. Programmable folding of fusion RNA complex driven by the 3WJ motif of phi29 motor pRNA. Nucleic Acids Res. 2013 Sep. 1; 42:e10. PMCID:PMC3902900
36. Haque F, Shu D, Shu Y, Shlyakhtenko L, Rychahou P, Evers M, Guo P. Ultrastable synergistic tetravalent RNA nanoparticles for targeting to cancers. Nano Today 2012; 7:245-57. PMCID:PMC3458310
37. Shu Y, Haque F, Shu D, Li W, Zhu Z, Kotb M, Lyubchenko Y, Guo P. Fabrication of 14 Different RNA Nanoparticles for Specific Tumor Targeting without Accumulation in Normal Organs. RNA 2013; 19:766-77. PMCID:PMC3683911
38. Abdelmawla S, Guo S, Zhang L, Pulukuri S, Patankar P, Conley P, Trebley J, Guo P, Li Q X. Pharmacological characterization of chemically synthesized monomeric pRNA nanoparticles for systemic delivery. Molecular Therapy 2011; 19:1312-22. PMCID:PMC3129564
39. Shu D, Li H, Shu Y, Xiong G, Carson W E, Haque F, Xu R, Guo P. Systemic delivery of anti-miRNA for suppression of triple negative breast cancer utilizing RNA nanotechnology. ACS Nano 2015; 9:9731-40
40. Rychahou P, Haque F, Shu Y, Zaytseva Y, Weiss H L, Lee E Y, Mustain W, Valentino J, Guo P, Evers B M. Delivery of RNA nanoparticles into colorectal cancer metastases following systemic administration. ACS Nano 2015 Feb. 24; 9(2):1108-16. PMCID:NIHMS685217
41. Lee T J, Haque F, Shu D, Yoo J Y, Li H, Yokel R A, Horbinski C, Kim T H, Kim S-H, Nakano I, et al. RNA nanoparticles as a vector for targeted siRNA delivery into glioblastoma mouse model. Oncotarget 2015; 6:14766-76. PMCID:PMC4558114
42. Cui D, Zhang C, Liu B, Shu Y, Du T, Shu D, Wang K, Dai F, Liu Y, Li C, et al. Regression of gastric cancer by systemic injection of RNA nanoparticles carrying both ligand and siRNA. Scientific reports 2015; 5:10726. PMCID:PMC4490273
43. Herbst R S, Heymach J V, Lippman S M. Lung cancer. N.Engl.J Med. 2008 Sep. 25; 359(13):1367-80
44. Farmer G. Targeted lung cancer therapies. Nat Rev.Drug Discov. 2004 July; 3(7):547-8
45. Kim H S, Mendiratta S, Kim J, Pecot C V, Larsen J E, Zubovych I, Seo B Y, Kim J, Eskiocak B, Chung H, et al. Systematic identification of molecular subtype-selective vulnerabilities in non-small-cell lung cancer. Cell 2013 Oct. 24; 155(3):552-66. PMCID:PMC3836195
46. Whitehurst A W, Bodemann B O, Cardenas J, Ferguson D, Girard L, Peyton M, Minna J D, Michnoff C, Hao W, Roth M G, et al. Synthetic lethal screen identification of chemosensitizer loci in cancer cells. Nature 2007 Apr. 12; 446(7137):815-9
47. Cancer Target Discovery and Development Network, Schreiber S L, Shamji A F, Clemons P A, Hon C, Koehler A N, Munoz B, Palmer M, Stern A M, Wagner B K, et al. Towards patient-based cancer therapeutics. Nat Biotechnol. 2010 September; 28(9):904-6. PMCID:PMC2939009
48. Tang H, Xiao G, Behrens C, Schiller J, Allen J, Chow C W, Suraokar M, Corvalan A, Mao J, White M A, et al. A 12-gene set predicts survival benefits from adjuvant chemotherapy in non-small cell lung cancer patients. Clin. Cancer Res 2013 Mar. 15; 19(6):1577-86. PMCID: PMC3619002
49. Sunaga N, Miyajima K, Suzuki M, Sato M, White M A, Ramirez R D, Shay J W, Gazdar A F, Minna J D. Different roles for caveolin-1 in the development of non-small cell lung cancer versus small cell lung cancer. Cancer Res 2004 Jun. 15; 64(12):4277-85
50. Fan TWM, Lane A N, Higashi R M, Farag M A, Gao H, Bousamra M, Miller D M. Altered regulation of metabolic pathways in human lung cancer discerned by C-13 stable isotope-resolved metabolomics (SIRM). MOLECULAR CANCER 2009 Jun. 26; 8:41
51. Xie H, Hanai J I, Ren J G, Kats L, Burgess K, Bhargava P, Signoretti S, Billiard J, Duffy K J, Grant A, et al. Targeting Lactate Dehydrogenase-A Inhibits Tumorigenesis and Tumor Progression in Mouse Models of Lung Cancer and Impacts Tumor-Initiating Cells. Cell Metabolism 2014 May 6; 19(5):795-809
52. Shareef M M, Cui N, Burikhanov R, Gupta S, Satishkumar S, Shajahan S, Mohiuddin M, Rangnekar V M, Ahmed M M. Role of tumor necrosis factor-alpha and TRAIL in high-dose radiation-induced bystander signaling in lung adenocarcinoma. Cancer Research 2007 Dec. 15; 67(24):11811-20
53. Wei Q O, Jiang H, Xiao Z, Baker A, Young M R, Veenstra T D, Colburn N H. Sulfiredoxin-Peroxiredoxin I V axis promotes human lung cancer progression through modulation of specific phosphokinase signaling. Proc. Natl. Acad. Sci. U.S.A 2011 Apr. 26; 108(17):7004-9
54. Jiang H, Wu L, Mishra M, Chawsheen H A, Wei Q. Expression of peroxiredoxin 1 and 4 promotes human lung cancer malignancy. Am. J Cancer Res 2014; 4(5): 445-60. PMCID:PMC4163610
55. Wei Q, Jiang H, Baker A, Dodge L K, Gerard M, Young M R, Toledano M B, Colburn N H. Loss of sulfiredoxin renders mice resistant to azoxymethane/dextran sulfate sodium-induced colon carcinogenesis. Carcinogenesis 2013 June; 34(6):1403-10. PMCID:PMC3670259
56. Chen D H, Baker M L, Hryc C F, DiMaio F, Jakana J, Wu W, Dougherty M, Haase-Pettingell C, Schmid M F, Jiang W, et al. Structural basis for scaffolding-mediated assembly and maturation of a dsDNA virus. Proc. Natl. Acad. Sci. U.S.A 2011 Jan. 25; 108(4):1355-60. PMCID: PMC3029737
57. Afonin K A, Viard M, Koyfman A Y, Martins A N, Kasprzak W K, Panigaj M, Desai R, Santhanam A, Grabow W W, Jaeger L, et al. Multifunctional RNA nanoparticles. Nano Lett. 2014 Oct. 8; 14(10):5662-71. PMCID:PMC4189619
58. Zhou Z H, Dougherty M, Jakana J, He J, Rixon F J, Chiu W. Seeing the herpesvirus capsid at 8.5 A. Science 2000 May 5; 288(5467):877-80
59. Prasad B V, Rothnagel R, Zeng C Q, Jakana J, Lawton J A, Chiu W, Estes M K. Visualization of ordered genomic RNA and localization of transcriptional complexes in rotavirus. Nature 1996 Aug. 1; 382(6590):471-3
60. Sheng J, Li L, Engelhart A E, Gan J H, Wang J W, Szostak J W. Structural insights into the effects of 2 '-5' linkages on the RNA duplex. Proc. Natl. Acad. Sci. U.S.A 2014 Feb. 25; 111(8):3050-5
61. Sheng J, Gan J H, Soares A S, Salon J, Huang Z. Structural insights of non-canonical U center dot U pair and Hoogsteen interaction probed with Se atom. Nucleic Acids Res. 2013 December; 41(22):10476-87
62. Sheng J, Zhang W, Hassan AEA, Gan J H, Soares A S, Geng S, Ren Y, Huang Z. Hydrogen bond formation between the naturally modified nucleobase and phosphate backbone. Nucleic Acids Res. 2012 September; 40(16): 8111-8
63. Sheng J, Hassan A E A, Zhang W, Zhou J F, Xu B Q, Soares A S, Huang Z. Synthesis, structure and imaging of 64. Sheng J, Jiang J S, Salon J, Huang Z. Synthesis of a 2'-Se-thymidine phosphoramidite and its incorporation into oligonucleotides for crystal structure study. Organic Letters 2007 Mar. 1; 9(5):749-52
65. Lyubchenko Y L, Shlyakhtenko L S, Ando T. Imaging of nucleic acids with atomic force microscopy. Methods 2011 Feb. 15; 54:274-83
66. Shlyakhtenko L S, Lushnikov A Y, Miyagi A, Li M, Harris R S, Lyubchenko Y L. Nanoscale structure and dynamics of ABOBEC3G complexes with single-stranded DNA. Biochemistry 2012 Aug. 14; 51(32):6432-40. PMCID:PMC3448016
67. Lane A N, Chaires J B, Gray R D, Trent J O. Stability and kinetics of G-quadruplex structures. Nucleic Acids Res. 2008 October; 36(17):5482-515
68. Dailey M M, Miller M C, Bates P J, Lane A N, Trent J O. Resolution and characterization of the structural polymorphism of a single quadruplex-forming sequence. Nucleic Acids Res. 2010 August; 38(14):4877-88
69. Miller M C, Buscaglia R, Chaires J B, Lane A N, Trent J O. Hydration Is a Major Determinant of the G-Quadruplex Stability and Conformation of the Human Telomere 3' Sequence of d(AG(3)(TTAG(3))(3)). J. Am. Chem. Soc. 2010 Dec. 8; 132(48):17105-7
70. Richards C I, Luong K, Srinivasan R, Turner S W, Dougherty D A, Korlach J, Lester H A. Live-cell imaging of single receptor composition using zero-mode waveguide nanostructures. Nano Lett. 2012 Jul. 11; 12(7):3690-4. PMCID:PMC3397148
71. Das S K, Liu Y Y, Yeom S, Kim D Y, Richards C I. Single-Particle Fluorescence Intensity Fluctuations of Carbon Nanodots. Nano Letters 2014 February; 14(2):620-5
72. Richards C I, Hsiang J C, Khalil A M, Hull N P, Dickson R M. FRET-Enabled Optical Modulation for High Sensitivity Fluorescence Imaging. J. Am. Chem. Soc. 2010 May 12; 132(18):6318-23
73. Zhang H, Endrizzi J A, Shu Y, Haque F, Sauter C, Shlyakhtenko L S, Lyubchenko Y, Guo P, Chi Yl. Crystal Structure of 3WJ Core Revealing Divalent Ion-promoted Thermostability and Assembly of the Phi29 Hexameric Motor pRNA. RNA 2013 Aug. 20; 19:1226-37. PMCID:PMC3753930
74. Zhang H, Shu D, Huang F, Guo P. Instrumentation and metrology for single RNA counting in biological complexes or nanoparticles by a single molecule dual-view system. RNA 2007; 13:1793-802. PMCID:PMC1986819
75. Zhang H, Guo P. Single molecule photobleaching (SMPB) technology for counting of RNA, DNA, protein and other molecules in nanoparticles and biological complexes by TIRF instrumentation. Methods 2014 Jan. 15; 67:169-76
76. Shu D, Zhang H, Petrenko R, Meller J, Guo P. Dual-channel single-molecule fluorescence resonance energy transfer to establish distance parameters for RNA nanoparticles. ACS Nano 2010 Nov. 23; 4(11):6843-53. PMCID:PMC2990273
77. Shu D, Zhang H, Jin J, Guo P. Counting of six pRNAs of phi29 DNA-packaging motor with customized single molecule dual-view system. EMBO J. 2007; 26:527-37. PMCID:PMC1783441
78. Tan Z J, Chen S J. Salt dependence of nucleic acid hairpin stability. Biophys J 2008 July; 95(2):738-52. PMCID:PMC2440479
79. Chen S J. RNA folding: conformational statistics, folding kinetics, and ion electrostatics. Annu.Rev.Biophys. 2008; 37:197-214. PMCID:PMC2473866
80. Zhao P, Zhang W B, Chen S J. Predicting secondary structural folding kinetics for nucleic acids. Biophys.J. 2010 Apr. 21; 98(8):1617-25. PMCID:PMC2856163
81. Tan Z J, Chen Si. Predicting ion binding properties for RNA tertiary structures. Biophys.J. 2010 Sep. 8; 99(5):1565-76. PMCID:PMC2931721
82. Reif R, Haque F, Guo P. Fluorogenic RNA Nanoparticles for Monitoring RNA Folding and Degradation in Real Time in Living Cells. Nucleic Acid Ther. 2013; 22(6):428-37. PMCID:PMC3507523
83. Hynes N E, Lane H A. ERBB receptors and cancer: the complexity of targeted inhibitors. Nat Rev.Cancer 2005 May; 5(5):341-54
84. Pantel K, Brakenhoff R H, Brandt B. Detection, clinical relevance and specific biological properties of disseminating tumour cells. Nat Rev.Cancer 2008 May; 8(5):329-40
85. Yarden Y, Sliwkowski M X. Untangling the ErbB signalling network. Nature Reviews Molecular Cell Biology 2001 February; 2(2):127-37
86. Esposito C L, Passaro D, Longobardo I, Condorelli G, Marotta P, Affuso A, de F, V, Cerchia L. A neutralizing RNA aptamer against EGFR causes selective apoptotic cell death. PLoS.One. 2011; 6:e24071. PMCID:PMC3167817
87. Thiel K W, Hernandez L I, Dassie J P, Thiel W H, Liu X, Stockdale K R, Rothman A M, Hernandez F J, McNamara J O, Giangrande P H. Delivery of chemo-sensitizing siRNAs to HER2+-breast cancer cells using RNA aptamers. Nucleic Acids Res. 2012 Jul. 1; 40:6319-37. PMCID:PMC3401474
88. Kim M Y, Jeong S. In vitro selection of RNA aptamer and specific targeting of ErbB2 in breast cancer cells. Nucleic Acid Ther. 2011 June; 21:173-8
89. Chen C H, Chernis G A, Hoang V Q, Landgraf R. Inhibition of heregulin signaling by an aptamer that preferentially binds to the oligomeric form of human epidermal growth factor receptor-3. Proc Natl Acad Sci USA 3 A.D. August 5; 100:9226-31
90. Rich J N, Reardon D A, Peery T, Dowell J M, Quinn J A, Penne K L, Wikstrand C J, Van Duyn L B, Dancey J E, McLendon R E, et al. Phase II trial of gefitinib in recurrent glioblastoma. J.Clin.Oncol. 2004 Jan. 1; 22(1):133-42
91. Brandes A A, Franceschi E, Tosoni A, Hegi M E, Stupp R. Epidermal growth factor receptor inhibitors in neuro-oncology: hopes and disappointments. Clin.Cancer Res. 2008 Feb. 15; 14(4):957-60
92. Gupta P B, Chaffer C L, Weinberg R A. Cancer stem cells: mirage or reality? Nat. Med. 2009 September; 15(9):1010-2
93. Clarke M F, Fuller M. Stem cells and cancer: two faces of eve. Cell 2006 Mar. 24; 124(6):1111-5
94. Shigdar S, Qiao L, Zhou S F, Xiang D, Wang T, Li Y, Lim L Y, Kong L, Li L, Duan W. RNA aptamers targeting cancer stem cell marker CD133. Cancer Lett. 2013 Mar. 1; 330(1):84-95
95. Bidlingmaier S, Zhu X, Liu B. The utility and limitations of glycosylated human CD133 epitopes in defining cancer stem cells. J. Mol. Med. (Berl) 2008 September; 86(9):1025-32. PMCID:PMC2585385

96. Shigdar S, Lin J, Yu Y, Pastuovic M, Wei M, Duan W. RNA aptamer against a cancer stem cell marker epithelial cell adhesion molecule. Cancer Sci. 2011 Feb. 1; 102: 991-8
97. Hong S, Leroueil P R, Majoros I J, Orr B G, Baker J R, Holl M M B. The binding avidity of a nanoparticle-based multivalent targeted drug delivery platform. Chem.& Biol. 2007 January; 14(1):107-15
98. Selawry O, Krant M, Scotto J, Kazam E, Schneiderman M, Olson K, Shnider B, Edmonson J, Holland J, Taylor S, III. Methotrexate compared with placebo in lung cancer. Cancer 1977 July; 40(1):4-8
99. Buccheri G, Ferrigno D, Rosso A. A phase II study of methotrexate, doxorubicin, cyclophosphamide, and lomustine chemotherapy and lonidamine in advanced non-small cell lung cancer. Cancer 1993 Sep. 1; 72(5): 1564-72
100. Laurie S A, Solomon B J, Seymour L, Ellis P M, Goss G D, Shepherd F A, Boyer M J, Arnold A M, Clingan P, Laberge F, et al. Randomised, double-blind trial of carboplatin and paclitaxel with daily oral cediranib or placebo in patients with advanced non-small cell lung cancer: NCIC Clinical Trials Group study BR29. Eur.J.Cancer 2014 March; 50(4):706-12
101. Oshita F, Saito H, Murakami S, Kondo T, Yamada K. Phase II study of paclitaxel and irinotecan with intercalated gefitinib in patients with advanced non-small-cell lung cancer. Am.J.Clin.Oncol. 2010 February; 33(1):66-9
102. Hirose T, Sugiyama T, Kusumoto S, Shirai T, Nakashima M, Yamaoka T, Okuda K, Ogura K, Ohnishi T, Ohmori T, et al. Phase II study of the combination of nedaplatin and weekly paclitaxel in patients with advanced non-small cell lung cancer. Anticancer Res. 2009 May; 29(5):1733-8
103. Boni C, Savoldi L, Bisagni G, Ceci G, Crino L, De L, V, Di C F, Lasagni L, Manenti A L, Moretti G, et al. Bolus versus 5-day continuous infusion of cisplatin with mitomycin and vindesine in the treatment of advanced non-small cell lung cancer (NSCLC): a phase III prospective randomised trial of the Italian Oncology Group for Clinical Research (GOIRC). Eur. J. Cancer 1998 November; 34(12):1974-6
104. Arrieta O, Gonzalez-De la Rosa C H, rechaga-Ocampo E, Villanueva-Rodriguez G, Ceron-Lizarraga T L, Martinez-Barrera L, Vazquez-Manriquez M E, Rios-Trejo M A, varez-Avitia M A, Hernandez-Pedro N, et al. Randomized phase II trial of All-trans-retinoic acid with chemotherapy based on paclitaxel and cisplatin as first-line treatment in patients with advanced non-small-cell lung cancer. J. Clin. Oncol. 2010 Jul. 20; 28(21):3463-71
105. Frampton J E. Crizotinib: a review of its use in the treatment of anaplastic lymphoma kinase-positive, advanced non-small cell lung cancer. Drugs 2013 December; 73(18):2031-51
106. Jones S, Thompson D, Barton J, Patton J, Shipley D, Greco F A, Spigel D, Infante J, Burris H A, III. A randomized phase II trial of oral topotecan versus docetaxel in the second-line treatment of non-small-cell lung cancer. Clin. Lung Cancer 2008 May; 9(3):154-9
107. White S C, Cheeseman S, Thatcher N, Anderson H, Carrington B, Hearn S, Ross G, Ranson M. Phase II study of oral topotecan in advanced non-small cell lung cancer. Clin. Cancer Res 2000 March; 6(3):868-73
108. D'Souza S S, Deluca P P. Methods to assess in vitro drug release from injectable polymeric particulate systems. Pharm. Res. 2006 March; 23(3):460-74
109. Milane L, Duan Z F, Amiji M. Pharmacokinetics and biodistribution of lonidamine/paclitaxel loaded, EGFR-targeted nanoparticles in an orthotopic animal model of multi-drug resistant breast cancer. Nanomedicine-Nanotechnology Biology and Medicine 2011 August; 7(4):435-44
110. Mordant P, Loriot Y, Lahon B, Castier Y, Leseche G, Soria J C, Vozenin M C, Decraene C, Deutsch E. Bioluminescent Orthotopic Mouse Models of Human Localized Non-Small Cell Lung Cancer: Feasibility and Identification of Circulating Tumour Cells. PLoS ONE 2011 Oct. 11; 6(10)
111. Onn A, Isobe T, Itasaka S, Wu W, O'Reilly M S, Ki H W, Fidler I J, Herbst R S. Development of an orthotopic model to study the biology and therapy of primary human lung cancer in nude mice. Clin.Cancer Res 2003 Nov. 15; 9(15):5532-9
112. Liu J, Blackhall F, Seiden-Long I, Jurisica I, Navab R, Liu N, Radulovich N, Wigle D, Sultan M, Hu J, et al. Modeling of lung cancer by an orthotopically growing H460S M variant cell line reveals novel candidate genes for systemic metastasis. Oncogene 2004 Aug. 19; 23(37): 6316-24
113. Rapp U R, Korn C, Ceteci F, Karreman C, Luetkenhaus K, Serafin V, Zanucco E, Castro I, Potapenko T. Myc Is a Metastasis Gene for Non-Small-Cell Lung Cancer. PLoS ONE 2009 Jun. 24; 4(6)
114. Weilbaecher K N, Guise T A, McCauley L K. Cancer to bone: a fatal attraction. Nat Rev. Cancer 2011 June; 11(6):411-25. PMCID:PMC3666847
115. Kim I S, Baek S H. Mouse models for breast cancer metastasis. Biochem.Biophys Res Commun. 2010 Apr. 9; 394(3):443-7
116. Francia G, Cruz-Munoz W, Man S, Xu P, Kerbel R S. Mouse models of advanced spontaneous metastasis for experimental therapeutics. Nat Rev.Cancer 2011 February; 11(2):135-41
117. Shi J, Wang Y, Zeng L, Wu Y, Deng J, Zhang Q, Lin Y, Li J, Kang T, Tao M, et al. Disrupting the interaction of BRD4 with diacetylated Twist suppresses tumorigenesis in basal-like breast cancer. Cancer Cell 2014 Feb. 10; 25(2):210-25. PMCID:PMC4004960
118. Wu Y, Wang Y, Yang X H, Kang T, Zhao Y, Wang C, Evers B M, Zhou B P. The deubiquitinase USP28 stabilizes LSD I and confers stem-cell-like traits to breast cancer cells. Cell Rep. 2013 Oct. 17; 5(1):224-36. PMCID:PMC4004762
119. Xiong G, Wang C, Evers B M, Zhou B P, Xu R. RORalpha suppresses breast tumor invasion by inducing SEMA3F expression. Cancer Res 2012 Apr. 1; 72(7): 1728-39. PMCID:PMC3319846
120. Xu X, Yu T, Shi J, Chen X, Zhang W, Lin T, Liu Z, Wang Y, Zeng Z, Wang C, et al. Thymine DNA glycosylase is a positive regulator of Wnt signaling in colorectal cancer. J Biol Chem. 2014 Mar. 28; 289(13):8881-90. PMCID:PMC3979391
121. Hensley P J, Desiniotis A, Wang C, Stromberg A, Chen C S, Kyprianou N. Novel pharmacologic targeting of tight junctions and focal adhesions in prostate cancer cells. PLoS ONE 2014; 9(1):e86238. PMCID:PMC3908921
122. Chen L, Voronovich Z, Clark K, Hands I, Mannas J, Walsh M, Nikiforova M N, Durbin E B, Weiss H, Horbinski C. Predicting the likelihood of an isocitrate dehydrogenase 1 or 2 mutation in diagnoses of infiltrative glioma. Neuro Oncol. 2014 May 23; 16:1478-83

Example 4: Fabrication of RNA Nanocages Capable of Photo-Controlled Release of Cargo RNA pyramid design, preparation and self-assembly: Synthetic DNA molecules were purchased from IDT DNA (www.idtdna.com) and amplified using primers containing the T7 RNA polymerase promoter sequence. All RNA strands were prepared by in vitro transcription of amplified DNA templates followed by purification using 8 M urea, 8% denaturing polyacrylamide gel electrophoresis (PAGE).

Equimolar concentration of five strands (1 µM) were mixed in 1× Tris buffer (100 mM NaCl, 50 mM Tris, pH 8.0) for bottom-up self-assembly of RNA pentahedron. The "one-pot" assembly was achieved by heating the strands at 85° C. for 5 minutes and slowly cooling down (over 45 minutes) to 4° C. using on an Eppendorf Mastercycle thermocycler. Then the assembled nanoparticles were analyzed on Native PAGE (described below).

Characterization of the self-assembled RNA pyramid nanoparticle: All constructs were assembled as described above, and 6× loading dye (80% sucrose, 0.01% bromophenol blue, 0.01% xylene cyanol) was mixed with each RNA sample before loading on the non-denaturing gels. All native gels were run in 1×TBM (89 mM Tris, 200 mM boric acid, and 2.5 mM MgCl2) buffer at 4° C., 90 V. Ethidium bromide (EB) solution was used for gel stain. Typhoon FLA 7000 (GE Healthcare) was used to image the stained gels.

Dynamic light scattering (DLS) was utilized to measure the apparent hydrodynamic size and zeta potential of RNA pyramid (100-200 nM in 1× Tris buffer at 25° C.) using Zetasizer nano-ZS (Malvern Instrument, LTD) as described previously. The laser wavelength used in this measurement is 633 nm. Three independent measurements were carried out to obtain the data.

Cryo-EM imaging: 2 µl of RNA pyramid nanoparticles solution (0.3 mg/ml) was applied onto a glow-discharged 200-mesh R1.2/1.3 Quantifoil grid. The grids were blotted for 1.5 s and rapidly frozen in liquid ethane using a Vitrobot Mark IV (FEI). Then the girds were transferred to JEM2200FS cryo-electron microscope (JEOL) operated at 200 kV with in-column energy filter with a slit of 20 eV for screening. Micrographs of the RNA pyramid nanoparticles were recorded on a 4 k×4 k CCD camera (Gatan) at 80,000× microscope magnification (corresponding to a calibrated sampling of 1.36 Å per pixel) and a dose rate of ~30 electrons electrons/sec/A2 with a total exposure time of 1.5 s. A total 27 images were collected with a defocus range of 2-4 µm.

Single particle image processing and 3D reconstruction: The image processing software package EMAN2.1, was used for the micrograph evaluation, particle picking, contrast transfer function correction, 2-D reference-free class averaging, initial model building and 3-D refinement of the cryo-EM data. We boxed a total of 1522 particles to generate the 2D class averages for building the initial models. At last, 1103 particles were used for final refinement, applying the c4 symmetry. The resolution for the final maps were estimated by the 0.143 criterion of FSC curve without any mask. A 25 Å Gauss low-pass filter was applied to the final 3D maps displayed in the Chimera software package.

Malachite green and spinach aptamer fluorescence measurement: Fluorescence emission of fluorogenic nanoparticles was detected using native 6% PAGE as previously described. 5 µM MG and 5 µM DFHBI dyes were simultaneously used to stain the gels. Then the gels were scanned on Typhoon FLA 7000 for the MG fluorescence emission at 473 nm and DFHBI fluorescence emission with an excitation at 473 nm. After obtaining images scanned at different wavelengths, the gels were stained with EB for imaging.

For fluorescence measurement in solution, multifunctional RNA pyramid harboring MG and spinach aptamer in 1× Tris buffer was incubated with 2 µM MG and 2 µM DFHBI (Lucerna, Inc.) at room temperature for 30 min. pRNA-3WJ with MG and spinach aptamer served as a positive control and RNA pyramid without functionalization served as a negative control. Fluorescence spectrum was recorded at 615 nm excitation (625-750 nm scanning for emission) for MG dye and 450 nm excitation (465-750 nm scanning for emission) for DFHBI dye using a fluorospectrophotometer (Horiba Jobin Yvon).

HBV ribozyme catalytic activity assay: HBV ribozyme-mediated cleavage of substrate was performed similarly to previously reported procedures. Briefly, the HBV genomic RNA substrate was 5'-Cy5 labeled by the Mirus Cy5 labeling kit followed by incubation with multifunctional RNA pyramid at the molar ratio of 4:1 at 37° C. for 1 h. Multifunctional RNA pyramid without HBV ribozyme was used as a negative control and pRNA-3WJ harboring HBV ribozyme served as a positive control. UREA PAGE was used to analyze the cleaved fragment and the gels were scanned under Cy5 channel using Typhoon fluorescent imaging system.

Streptavidin (STV) aptamer binding assay: STV agarose beads (Thermo Scientific) was conditioned using binding buffer (PBS buffer with 10 mM $Mg^{2+}$). Multifunctional RNA pyramid was incubated with STV agarose beads at room temperature for 30 min. Then spun down the beads at 500×g for 1 min and collected the supernatant. 50 µl of binding buffer was used to wash the beads and the fractions were collected. In the elution step, 5 mM biotin in binding buffer was added into the mixture and the fractions were collected for three times. Nanodrop was used to measure the UV absorption at 260 nm of all the fractions. Then the fractions were analyzed by native 6% PAGE. pRNA-3WJ harboring STV aptamer was used as a negative control.

ATP aptamer binding assay: Strand 1 with MG aptamer and strand 5 with ATP aptamer were $^{32}P$ labeled at 5'-end phosphate using PerkinElmer [$\gamma$-$^{32}P$]-ATP by Shrimp alkaline phosphatase (rSAP, New England Biolabs Inc.) and T4 polynucleotide kinase (T4 PNK, New England Biolabs Inc.). C-8 ATP-immobilized agarose resin (Sigma-aldrich) was soaked in DEPC water and ATP binding buffer (300 mM NaCl, 20 mM Tris, pH 7.6, 5 mM $MgCl_2$) before incubation with RNA. Then multifunctional RNA pyramid nanoparticles were incubated with the resin at room temperature for 30 min followed by washing three times using binding buffer. The resin was suspended in scintillation liquid for radioactivity measurement using scintillation counter (Packard 1900TR liquid scintillation analyzer).

Results

Figure 14A:
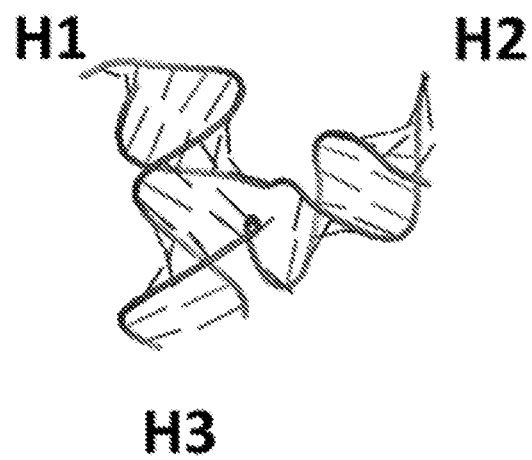
FIGS. 14A-14F demonstrate the design and characterization of RNA Nanocages that can be capable of photocontrolled release of cargo.
Figure 14B:
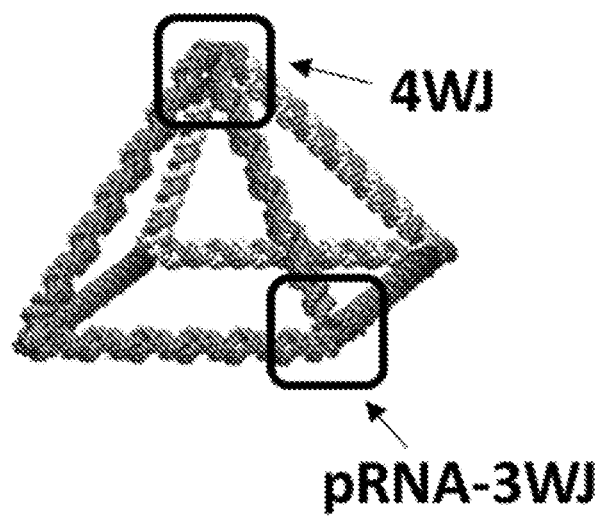
Figure 14C:
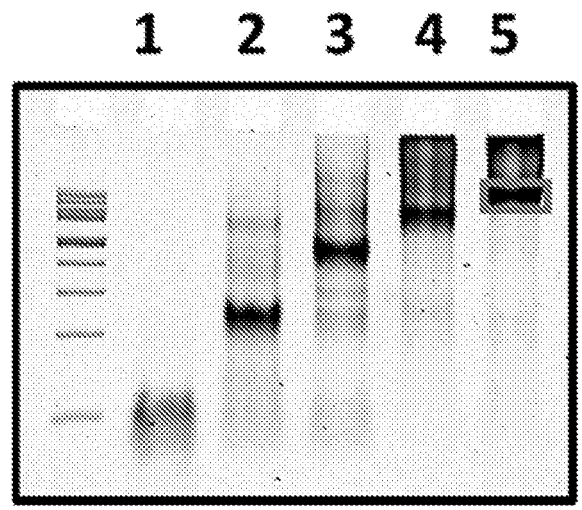
Figure 14D:
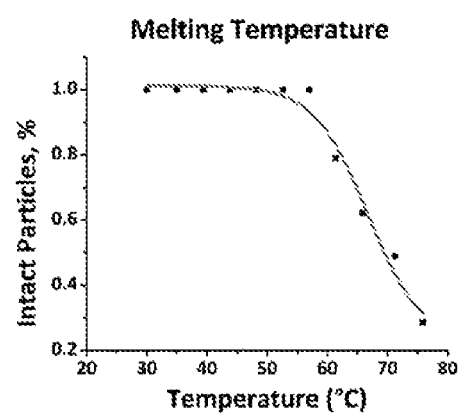
Figure 14E:
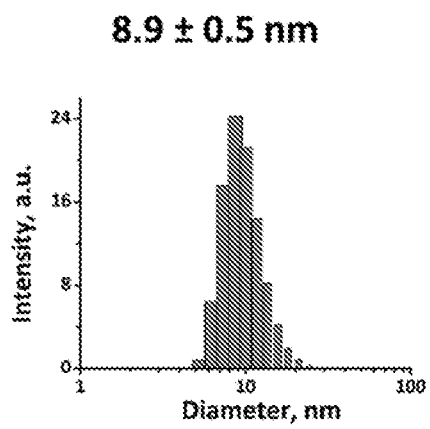
Figure 14F:
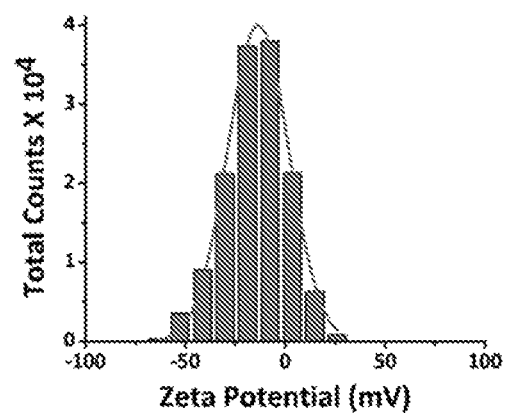

FIGS. 14A-14F demonstrate the design and characterization of RNA Nanocages that can be capable of photocontrolled release of cargo. FIG. 14A shows a crystal structure of the 3WJ of pRNA composed of three strands. FIG. 14B shows a three dimensional structure of pyramid-shaped RNA nanocage with four 3WJs at the bottom and one four-way junction at the vertex. FIG. 14C shows a representative native PAGE assembly gel showing the step-wise assembly of RNA pyramid. FIG. 14D shows a melting temperature profile of RNA pyramid nanoparticles characterized by TGGE. FIG. 14E demonstrates the size of the RNA pentahedron determined by dynamic light scattering (DLS). FIG. 14F demonstrates the zeta potential of the RNA pyramid.

Figure 15A:
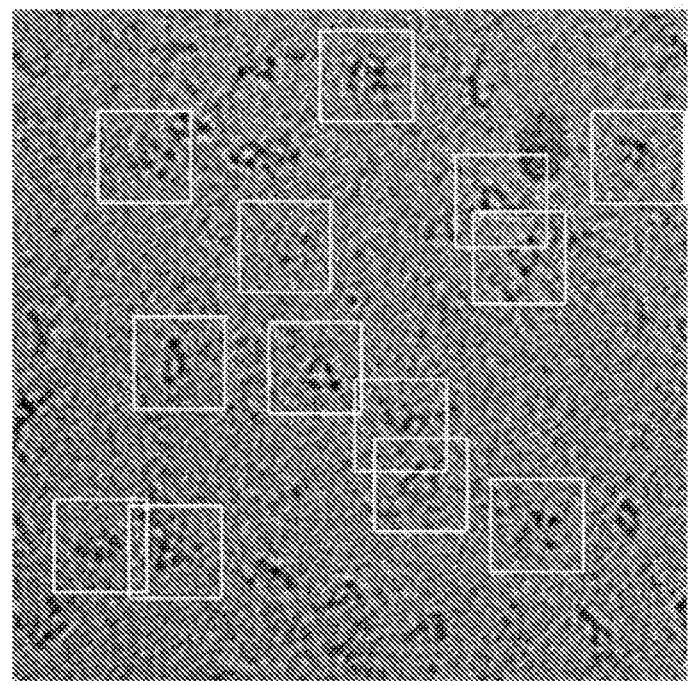
FIGS. 15A-15C demonstrate the results of a CryoEM analysis of RNA pyramid.
Figure 15B:
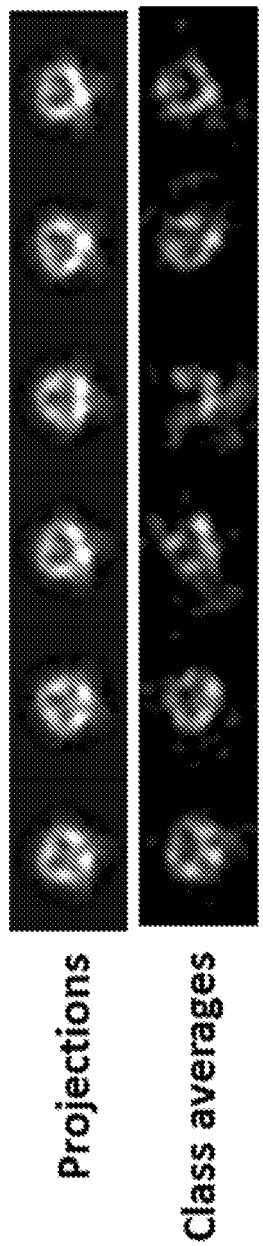
Figure 15B:
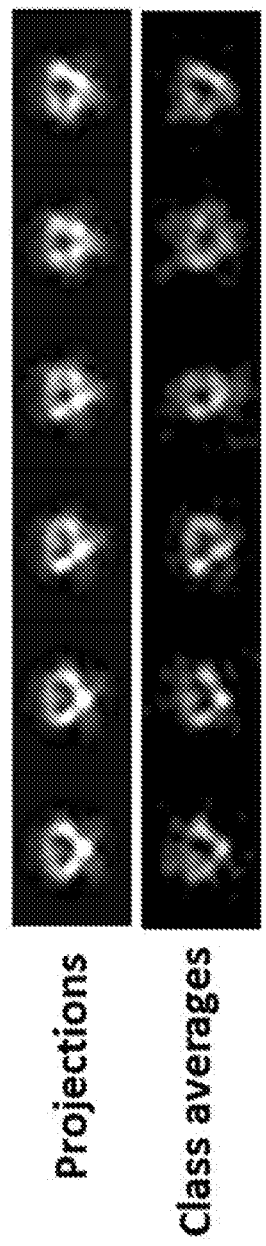
Figure 15C:
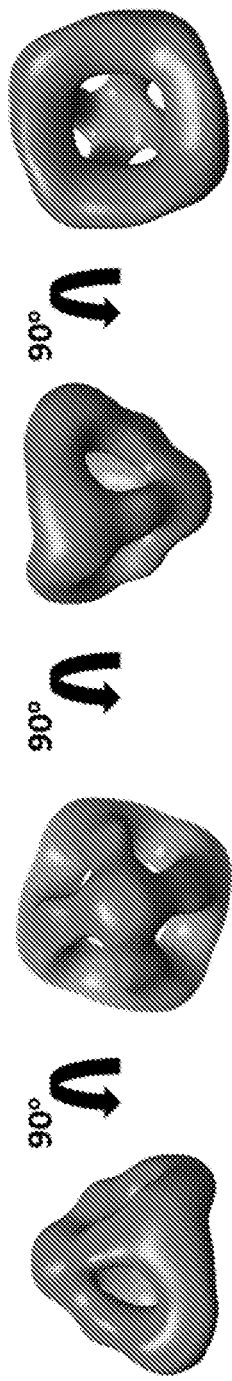

FIGS. 15A-15C demonstrate the results of a CryoEM analysis of RNA pyramid. FIG. 15A shows a raw cryoEM (cryogenic electron microscopy) image. White boxes indicate individual RNA pyramid. FIG. 15B demonstrates a comparison between individual raw particles and computer-generated two-dimensional projections of the 3D model in similar orientations. FIG. 15C shows four views of the pentahedron model reconstructed from cryoEM images.

Figure 16:
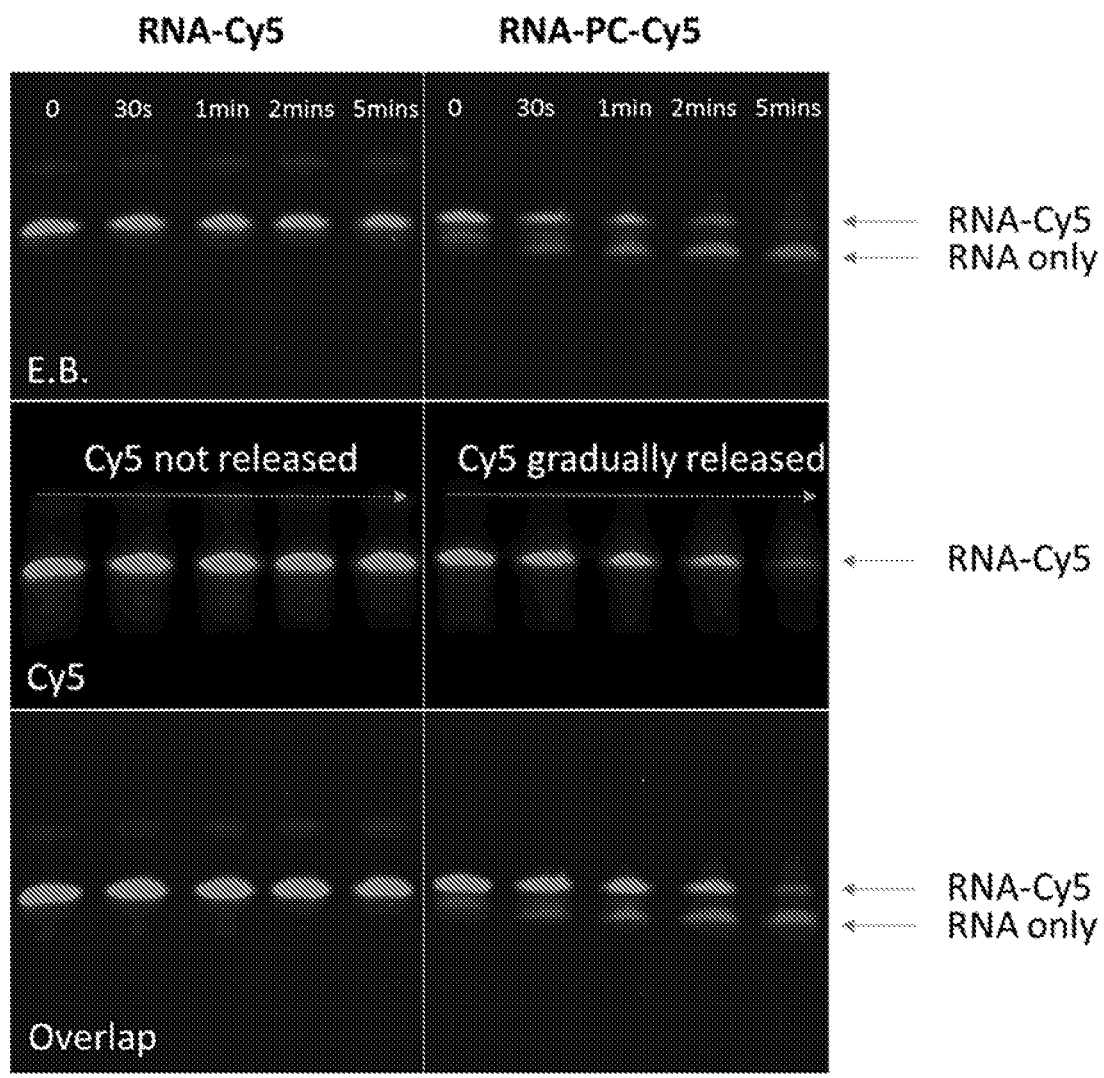
FIG. 16 shows a panel of images demonstrating the photo-controlled release of Cy5 on RNA strands. In the left panel, RNA strand conjugated with Cy5 without photocleavable spacer did not show Cy5 release under UV irradiation while its counterpart with a photocleavable spacer, in the right panel, showed fast release of Cy5 within 5 mins.

FIG. 16 shows a panel of images demonstrating the photo-controlled release of Cy5 on RNA strands. In the left panel, RNA strand conjugated with Cy5 without photocleavable spacer did not show Cy5 release under UV irradiation while its counterpart with a photocleavable spacer, in the right panel, showed fast release of Cy5 within 5 mins.

Figure 17:
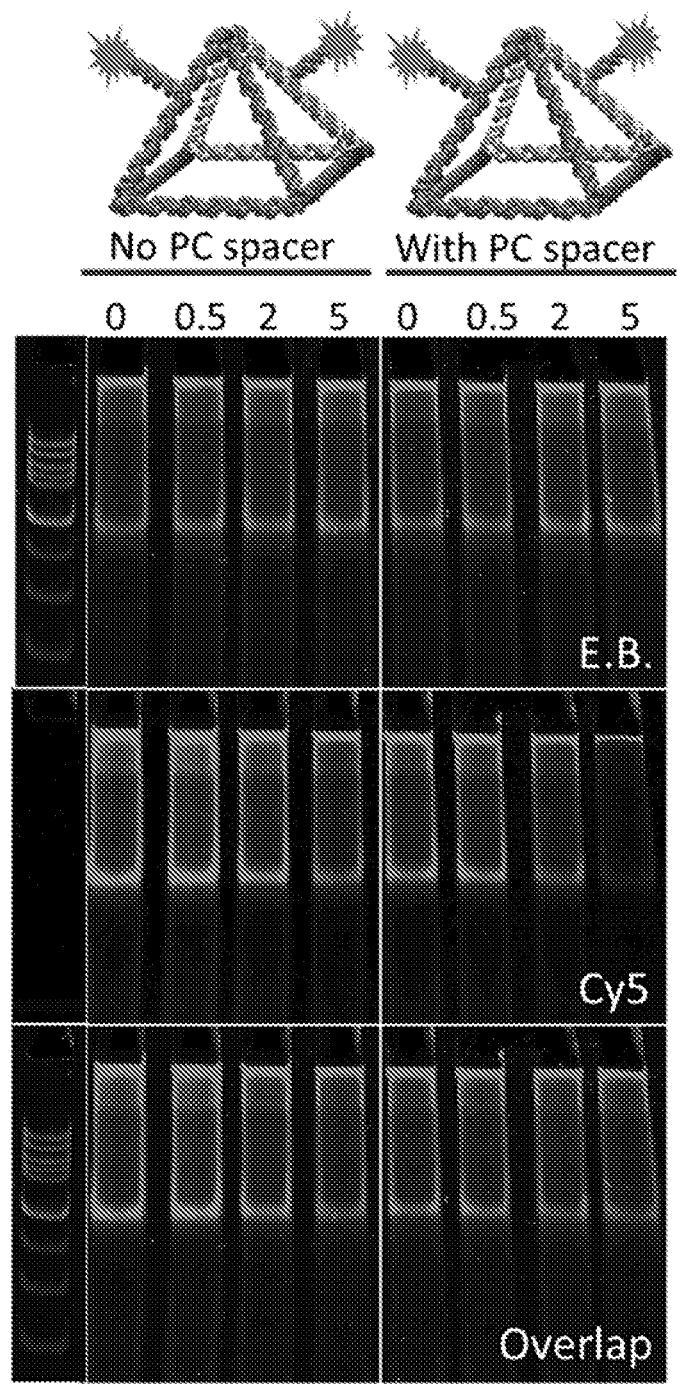
FIG. 17 shows a panel of images demonstrating the photo-controlled release of Cy5 on a RNA nanocage.

FIG. 17 shows a panel of images demonstrating the photo-controlled release of Cy5 on a RNA nanocage.

Figure 18A:
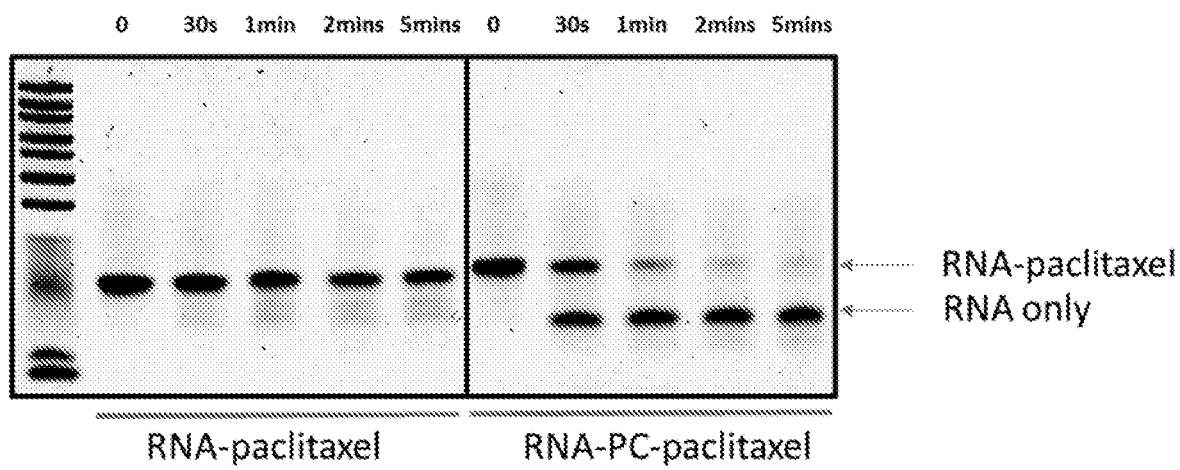
FIGS. 18A and 18B show images of a gels demonstrating the fabrication of RNA nanocages conjugated with paclitaxel or Cy5 with or without a photoclevable (PC) spacer.
Figure 18B:
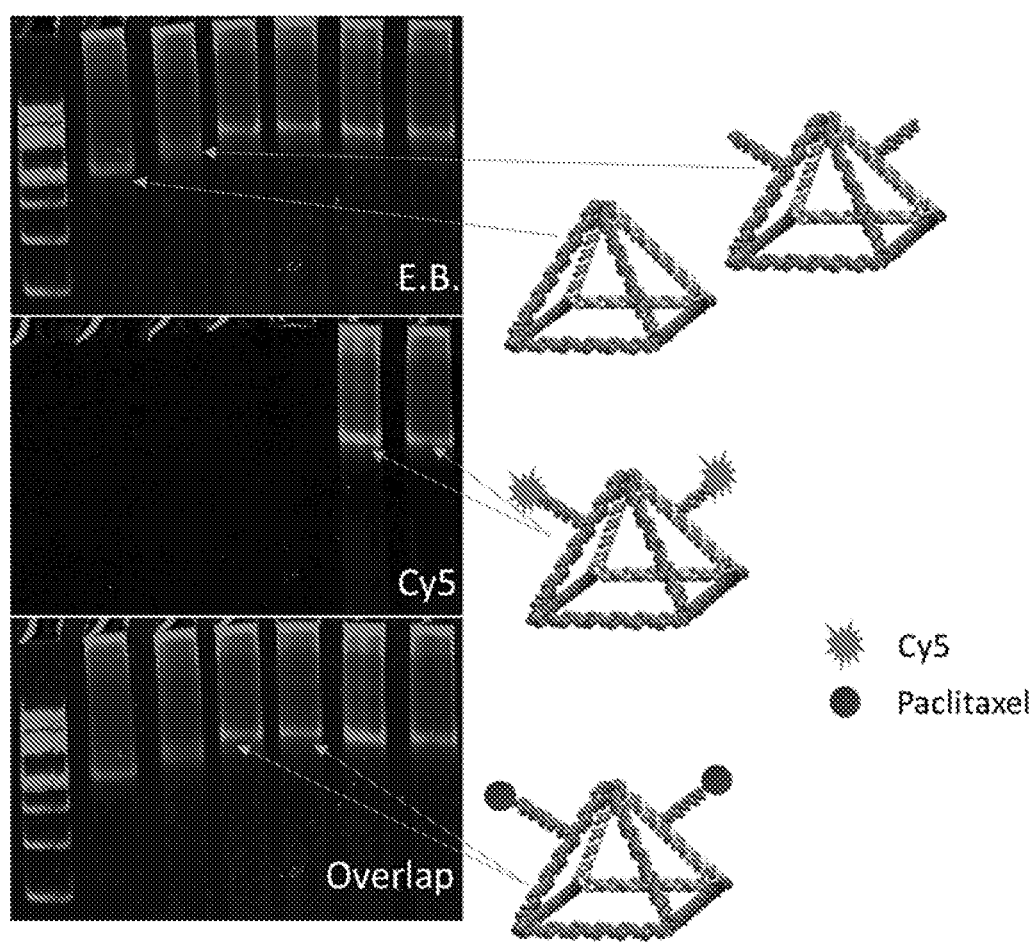

FIGS. 18A and 18B show images of a gels demonstrating the fabrication of RNA nanocages conjugated with paclitaxel or Cy5 with or without a photoclevable (PC) spacer.

Figure 19:
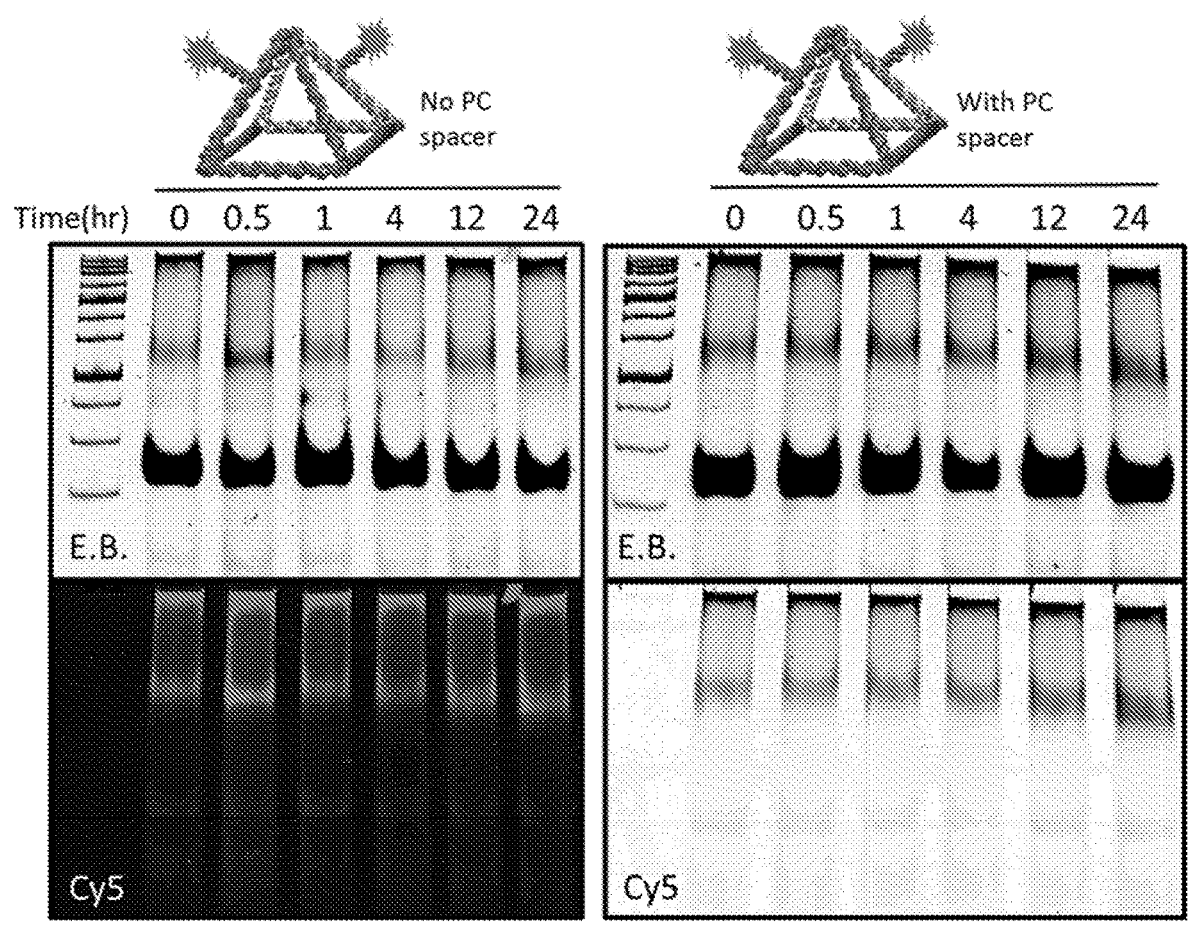
FIG. 19A show representative gel images that demonstrate the serum stability of RNA nanocages that are capable of photo-controlled release of cargo (FIG. 19).

FIG. 19 shows representative gel images that demonstrate the serum stability of RNA nanocages that are capable of photo-controlled release of cargo (FIG. 19).

What is claimed is:

1. A three-dimensional cage molecule, wherein the cage molecule comprises at least three pRNA three-way junction (pRNA-3WJ) strands that are configured to self-assemble into the three dimensional cage molecule, wherein the three dimensional cage molecule has an inner cavity, wherein a cargo compound is attached to one of the at least three pRNA-3J RNA strands by a linker, wherein the three-dimensional cage molecule is configured to encapsulate the cargo molecule inside the cavity of the three dimensional cage molecule during self-assembly.

2. The three-dimensional cage molecule of claim 1, wherein the three-dimensional cage molecule is in the shape of a tetrahedron.

3. The three-dimensional cage molecule of claim 1, comprising at least four pRNA-3WJ strands and at least one four-way junction (4WJ) strands.

4. The three-dimensional cage molecule of claim 1, wherein the three-dimensional cage molecule further comprises at least one functional moiety.

5. The three-dimensional cage molecule of claim 4, wherein the functional moiety is a therapeutic moiety or a diagnostic moiety.

6. The three-dimensional cage molecule of claim 4, wherein the functional moiety is an RNA aptamer, a ribozyme, siRNA, or protein-binding RNA aptamer.

7. The three-dimensional cage molecule of claim 4, wherein the three-dimensional cage molecule comprises at least two functional moieties.

8. The three-dimensional cage molecule of claim 7, wherein the at least two functional moieties are the same.

9. The three-dimensional cage molecule of claim 7, wherein at least two of the functional moieties are different.

10. The three-dimensional cage molecule of claim 1, wherein the three-dimensional cage molecule is scalable.

11. The three-dimensional cage molecule of claim 1, wherein the linker is a cleavable linker.

12. The three-dimensional cage molecule of claim 11, wherein the cleavable linker is a photo-cleavable linker.

13. The three-dimensional cage molecule of claim 1, wherein at least one ribonucleotide of an RNA strand in the three-dimensional molecule is 2'F modified.

14. A composition comprising the three-dimensional cage molecule of claim 1.

15. The composition of claim 1, further comprising a pharmaceutically acceptable excipient, carrier, or diluent.

16. The composition of claim 15 wherein the pharmaceutical composition is formulated for the treatment of a disease.

17. A method of altering the expression of a target gene in a cell comprising contacting the cell with a therapeutically effective amount of the composition of claim 16.

18. A method of treating disease in a subject, comprising administering to the subject the pharmaceutical composition of claim 14.

19. The three-dimensional cage molecule of claim 1, wherein the pRNA-3WJ RNA strands comprise the nucleic acid sequences SEQ ID NO:2, SEQ ID NO:3, SEQ ID NO:4, and SEQ ID NO:5;
   SEQ ID NO:11, SEQ ID NO:12, SEQ ID NO:13, and SEQ ID NO:14;
   SEQ ID NO:15, SEQ ID NO:16, SEQ ID NO:17, and SEQ ID NO:18; or SEQ ID NO:20, SEQ ID NO:21, SEQ ID NO:22, and SEQ ID NO:23;

20. The three-dimensional cage molecule of claim 1, wherein the cargo molecule is a small molecule.

* * * * *